(12) United States Patent
Roberts, II et al.

(10) Patent No.: US 8,822,542 B2
(45) Date of Patent: *Sep. 2, 2014

(54) ISOKETAL SCAVENGERS AND MITIGATION OF DISORDERS INVOLVING OXIDATIVE INJURY

(75) Inventors: L. Jackson Roberts, II, Gallatin, TN (US); Jeffrey R. Balser, Brentwood, TN (US); Sean S. Davies, Nashville, TN (US); Venkataraman Amarnath, Nashville, TN (US); Prakash C. Viswanathan, Chesapeake, VA (US)

(73) Assignee: Vanderbilt University, Nashville, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/395,464

(22) Filed: Feb. 27, 2009

(65) Prior Publication Data

US 2012/0157501 A1 Jun. 21, 2012

Related U.S. Application Data

(63) Continuation-in-part of application No. 11/254,846, filed on Oct. 20, 2005, now Pat. No. 7,705,054.

(60) Provisional application No. 61/031,882, filed on Feb. 27, 2008.

(51) Int. Cl.
*A01N 33/02* (2006.01)
*A61K 31/13* (2006.01)

(52) U.S. Cl.
USPC ......................................... 514/649; 514/669

(58) Field of Classification Search
None
See application file for complete search history.

(56) References Cited

U.S. PATENT DOCUMENTS

| | | | |
|---|---|---|---|
| 7,175,828 B2 | 2/2007 | Findeis et al. | |
| 2005/0031651 A1 | 2/2005 | Gervais et al. | |
| 2007/0149485 A1 | 6/2007 | Friesen | |
| 2008/0227776 A1 | 9/2008 | Oates et al. | |

FOREIGN PATENT DOCUMENTS

| | | |
|---|---|---|
| WO | 00/21516 A2 | 4/2000 |
| WO | 2005/072295 A2 | 8/2005 |

OTHER PUBLICATIONS

Kedar NP. "Can we prevent Parkinson's and Alzheimer's disease?" Journal of Postgraduate Medicine, 2003, vol. 49, Issue 3, pp. 236-245.*
Kannan et al. Effect of Vitamin B6 on Oxygen Radicals, Mitochondrial Membrane Potential, and Lipid Peroxidation in H2O2-Treated U927 Monocytes. Free Radical Biology & Medicine, vol. 36, No. 4, pp. 423-428, 2004.*
Head, E. "Oxidative Damage and Cognitive Dysfunction: Antioxidant Treatments to Promote Healthy Brain Aging". Neurochem Res (2009) 34: 670-678.*
Balser, J.R. 1999. Sodium "channelopathies" and sudden death: must you be so sensitive? Circ Res 85:872-874.
Bernoud-Hubac, et al., 2nd (2001) Formation of highly reactive gamma-ketoaldehydes (neuroketals) as products of the neuroprostane pathway. J Biol Chem 276, 30964-30970.
Boutaud, et al. (1999) Characterization of the lysyl adducts formed from prostaglandin H2 via the levuglandin pathway. Biochemistry 38, 9389-9396.
Brame, et al., 2nd (1999) Identification of extremely reactive gamma-ketoaldehydes (isolevuglandins) as products of the isoprostane pathway and characterization of their lysyl protein adducts. J Biol Chem 274, 13139-13146.
Davies et al., Pyridoxamine analogs scavenge lipid-derived gamma-ketoaldehydes and protect against H2O2-mediated cytotoxicity, Biochemistry. Dec. 26, 2006; vol. 45(51): pp. 15756-15767, p. 1, paragraph 1 to p. 2, para 2; p. 9, para 3; Fig 1, Fig 5.
Davies, et al., 2nd (2002) Effects of reactive gamma-ketoaldehydes formed by the isoprostane pathway (isoketals) and cyclooxygenase pathway ((levuglandins) on proteasome function. Faseb J 16, 715-717.
Fessel, J.P., et al. 2nd. 2002. Discovery of lipid peroxidation products formed in vivo with a substituted tetrahydrofuran ring (isofurans) that are favored by increased oxygen tension. Proc Natl Acad Sci 99:16713-16718.
Montine, et al., (1999) Cerebrospinal fluid F2-isoprostanes are elevated in Huntington's disease. Neurology 52, 1104-1105.
Montine, et al., (1999) Increased CSF F2-isoprostane concentration in probable AD. Neurology 52, 562-565.
Montine, et al., (1998) Cerebrospinal fluid F2-isoprostane levels are increased in Alzheimer's disease. Ann. Neurol. 44, 410-413.
Morrow, et al., A series of prostaglandin F2-like compounds are produced in vivo in humans by a non-cyclooxygenase, free radical-catalyzed mechanism. Proc Natl Acad Sci USA, 2ns (1990) 87, 9383-9387.
Morrow, et al., Comparison of formation of D2/E2-isoprostanes and F2-isoprostanes in vitro and in vivo-effects of oxygen tension and glutahione. Arch Biochem Biophys (1998), 353, 160-171.
Morrow, et al., 2nd (1996). Nonenzymatic free radical-catalyzed generation of thromboxane-like compounds (isothromboxanes) in vivo. J Biol Chem 271, 23185-23190.
Morrow, et al., 2nd (1994). Free radical-induced generation of isoprostanes in vivo. Evidence for the formation of D-ring and E-ring isoprostanes. J. Biol Chem 269, 4317-4326.
Morrow, J.D., et al., (1998). Mass spectrometric quantification of F2-Isoprostanes in biological fluids and tissues as a measure of oxidant stress. Methods Enzymol. 300, 3-12.
Ong, B.H., et al., (2000). A structural rearrangement in the sodium channel pore linked to slow inactivation and use dependence. J. Gen Physlol 116:653-662.

(Continued)

*Primary Examiner* — Renee Claytor
(74) *Attorney, Agent, or Firm* — Stites & Harbison PLLC; Richard S. Myers, Jr.

(57) ABSTRACT

A method of treating and/or preventing oxidative damage, comprising administering an effective IsoK/NeuroK adduct formation suppressing amount of a phenolic amine compound and/or pyridoxamine or pyridoxamine analog, including embodiments where the phenolic compound is at least one of a pyridoxamine, salicylamine, tyrosine compound or an analog thereof.

8 Claims, 26 Drawing Sheets

(56) References Cited

OTHER PUBLICATIONS

Pratico, D., et al., (2000). Increased 8, 12-iso-iPF2alpha-VI in Alzheimer's disease: correlation of a noninvasive index of lipid peroxidation with disease severity. Ann Neurol 48, 809-812.

Pu, J. et al., (1998). Lidocaine action on Na+ currents in ventricular myocytes from the epicardial border zone of the infarcted heart. Circ Res 83:431-440.

Reich, et al., (2001). Brain regional quantification of F-ring and D-/E-ring isoprostanes and neuroprostanes in Alzheimer's disease. Am. J. Pathol. 158- 293-297.

Reich, et al., (2000). Formation of novel D-ring and E-ring isoprostane-like compounds (D4/E4- neuroprostanes) in vivo from docosahexaenoic acid. Biochemistry 39, 2376-2383.

Roberts, et al., (1998). Formation of isoprostane-like compounds (neuroprostanes) in vivo from docosahexaenoic acid. J. Biol Chem 273, 13605-13612.

Roberts, L.J., et al., (2001). Measurement of F(2)-isoprostanes unveils profound oxidative stress in aged rats. Biochem Biophys Res Commun 287, 254-256.

Veldkamp, M.W., et al., (2000). Two distinct congenital arrhythmias evoked by a multidysfunctional Na(+) channel. Circ Res 86:E91-E97.

Viswanathan, P.C., et al., (2001). Gating-dependent mechanisms for flecainide action in SCN5A-linked arrhythmia syndromes. Circ 104:1200-1205.

Davies, Sean S. et al., "Treatment With Isoketal Scavenger, Salicylamine, Prevents Loss of Working Memory in Humanized Apoe4 Mice", Free Radical Biology & Medicine, vol. 45, No. Suppl. 1, 2008, pp. S103-S104, XP-002691141.

Maezawa, H. et al., Database Biosis (Online) Biosciences Information Service, Philadelphia, PA, US; 1990, "The Effect of ONO-3144 on Limiting Infarct Size in a Rat Model of Myocardial Infarction and Reperfusion", Dokkyo Journal of Medical Science, vol. 17, No. 2, 1990, pp. 85-92, XP-002691142.

Lefer, A.M. et al., Database Medline (Online) US National Library of Medicine (NLM), Bethesda, MD, US; 1981, "Beneficial actions of a free radical scavenger in traumatic shock and myocardial ischemia", Circulatory Shock 1981, vol. 8, No. 3, 1981, pp. 273-282, XP-002691143.

Boyden, Penelope A. et al., "Potential role of isoketals formed via the isoprostane pathway of lipid peroxidation in ischemic arrhythmias", Journal of Cardiovascular Pharmacology Nov. 2007, vol. 50, No. 5, p. 481, col. 1, paragraph 1, p. 484, col. 2, paragraph 2, p. 485, col. 1, XP-002691144.

Bernoud-Hubac, N. et al., "Low concentrations of reactive y-ketoaldehydes prime thromboxane-dependent human platelet aggregation via p38-MPAK activation", Biochimica and Biophysica ACTA, Molecular and Cell Biology of Lipids, Elsevier, Amstaerdam, NL, vol. 1791, No. 4, Apr. 1, 2009, pp. 307-313, XP-026011351.

Negre-Salvayre A., et al., "Advanced lipid peroxidation end products in oxidative damage to proteins. Potential role in diseases and therapeutic prospects for the inhibitors", British Journal of Pharmacology Jan. 2008, vol. 153, No. 1, Jan. 2008, pp. 6-20, XP-002691145.

\* cited by examiner

ICIS: 8.3.0 SP2 for OSF1

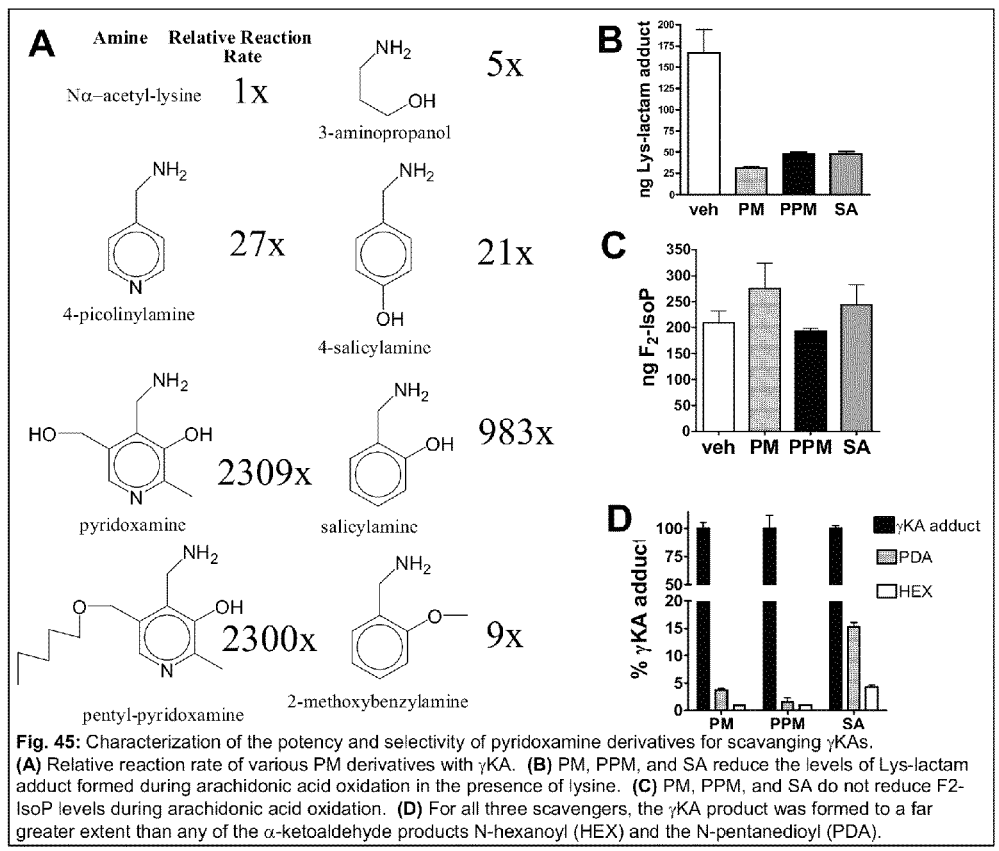

Fig. 45: Characterization of the potency and selectivity of pyridoxamine derivatives for scavanging γKAs. (A) Relative reaction rate of various PM derivatives with γKA. (B) PM, PPM, and SA reduce the levels of Lys-lactam adduct formed during arachidonic acid oxidation in the presence of lysine. (C) PM, PPM, and SA do not reduce F2-IsoP levels during arachidonic acid oxidation. (D) For all three scavengers, the γKA product was formed to a far greater extent than any of the α-ketoaldehyde products N-hexanoyl (HEX) and the N-pentanedioyl (PDA).

Figure 46

Fig. 47: γKA-Lys-lactam adduct tissue concentrations 7 days post MI. n=2-3 mice per group Survival after MI. Treatment with SA was started 3 days prior to coronary ligation.

ISOKETAL SCAVENGERS AND MITIGATION OF DISORDERS INVOLVING OXIDATIVE INJURY

PRIORITY INFORMATION

This application claims priority to U.S. Patent Application Ser. No. 61/031,882, filed Feb. 27, 2008; and is a Continuation-In-Part of U.S. patent application Ser. No. 11/254,846, filed Oct. 20, 2005 now U.S. Pat. No. 7,705,054; the contents of both applications are incorporated herein by reference.

GOVERNMENT SUPPORT

The present invention was made with support from National Institutes of Health Grant Numbers GM42057 and HL79365. The Government may have rights to this invention.

FIELD OF THE INVENTION

The present invention relates generally to the field of treating neurodegenerative and cardiovascular diseases, and more specifically to the field of controlling isoketals and neuroketals.

BACKGROUND AND SUMMARY OF THE INVENTION

The present inventors have discovered a substantial body of evidence for the occurrence of overproduction of free radicals, i.e. oxidative injury or oxidative stress, has been implicated is an increasing number and variety of human diseases. These include neurodegenerative diseases, e.g. Alzheimer's and Parkinson's disease, ventricular fibrillation, atherosclerosis, myocardial infarction and arrhythmias, diabetes, etc., by demonstrating overproduction of isoprostanes (IsoPs) and neuroprostanes (NeuroPs). IsoPs and NeuroPs are prostaglandin-like compounds produced by free radical induced peroxidation of arachidonic acid (AA) and docosahexaenoic acid (DHA), respectively. Isoketals (IsoKs) and neuroketals (NeuroKs) are highly reactive γ-ketoaldehydes produced by the IsoP and NeuroP pathways, respectively. IsoKs and NeuroKs rapidly adduct to lysyl residues of proteins and also Exhibit A unique and remarkable proclivity to crosslink proteins.

The present invention encompasses discoveries from studies both in brains from patients with Alzheimer's disease (AD) and an animal model of age-related dementia relevant to AD, ApoE null mice overexpressing human ApoE4.

Thus, an aspect of the present invention is identification of proteins adducted by IsoKs and NeuroKs in brains from patients with AD and the mouse model of AD dementia. Furthermore, the present invention demonstrates the relationship between onset of behavioral abnormalities and the occurrence of oxidative stress and IsoK/NeuroK adduct formation in the mouse model. Thus, the ability of selected antioxidants to suppress oxidative injury and IsoK/NeuroK adduct formation and improve behavioral abnormalities in these mice is determined.

Additionally, another aspect of the present invention is a novel pharmacologic intervention with IsoK scavengers such as pyridoxamine (PM) and salicylamine (SA), for example, that preferentially intercepts and prevents IsoKs/NeuroKs from adducting to proteins in vitro, to prevent IsoK/NeuroK adduct formation and improve behavioral abnormalities in these mice. In this regard, suppression of oxidative stress in general and specifically suppression of IsoK/NeuroK adduct formation is a valuable strategy to mitigate the progression of neurodegeneration and dementia in neurological diseases associated with oxidative stress, such as AD.

Oxidative stress plays a fundamental role in the pathogenesis of such diseases, which leads to the formation of IsoKs and NeuroKs that adduct to and alter the function of critical cellular proteins. This in turn also impairs proteasomal degradation of adducted proteins and inhibits proteasome function, causing neuronal dysfunction and death resulting in dementia.

Summary of several abbreviations used herein: $F_2$-isoprostane ($F_2$-IsoP), $F_4$-neuroprostane ($F_4$-NeuroP), isoketal (IsoK), neuroketal (NeuroK), 4-hydroxynonenal (HNE), Alzheimer's disease (AD), arachidonic acid (AA), docosahexaenoic acid (DHA), amyloid precursor protein (APP), amyloid beta (Aβ), paired helical filament (PHF), neurofibrillary tangles (NFT), pyridoxamine (PM), salicylamine (SA), apolipoprotein E (ApoE), vascular dementia (VaD), dementia with Lewy bodies (DLB), multisystem atrophy (MSA), transgenic (Tg), homocysteine (HCys), liquid chromatography (LC), electrospray ionization (ESI), mass spectrometry (MS), collisional induced dissociation (CID), cerebrospinal fluid (CSF).

Isoketals are the most reactive products of lipid peroxidation heretofore identified. IsoKs adduct almost instantaneously to protein lysine residues and readily induce protein-protein cross-links. In spite of the remarkable reactivity of IsoKs, the present inventors have identified compounds that effectively intercept (scavenge) IsoKs from adducting to proteins.

The IsoK scavengers of the present invention are compounds of the present invention, such as salicylamine (SA), for example, and analogs thereof. The compounds of the present invention prevent cell death in cells exposed to a lethal concentration of a general oxidant—hydrogen peroxide.

As indicated herein, IsoKs are a major mediator of oxidant induced cell injury/death. Additionally, as indicated herein, therapeutic use of the IsoK scavengers of the present invention have beneficial effects in a wide variety of diseases associated with oxidative injury.

Age-related dementias are a major and costly public health problem. The most prominent cause of dementia in the elderly is Alzheimer's disease (AD), but others include vascular dementia (VaD), dementia with Lewy bodies (DLB), and multisystem atrophy (MSA). Remarkable advances have been made towards understanding the genetic basis for early-onset familial AD with the identification of mutations in amyloid precursor protein (APP), and presenilin-1 and presenilin-2 genes. However, these mutations account for only about 0.5% of all AD cases. Furthermore, even these mutations do not result in recognizable disease until well into middle age. The widespread abundance of sporadic late-onset AD, and the relatively late age of "early onset" familial AD suggests that factors other than genetic mutations contribute importantly to the development of AD.

One attractive candidate mechanism contributing to the pathogenesis of AD and other dementias is oxidative stress. A considerable body of evidence has been obtained that supports a potential role for oxidative injury in the pathogenesis of AD. First, levels of biomarkers of oxidant injury are increased in the brain and CSF from patients with AD. Moreover, several known risk factors for AD induce an oxidant stress. In this regard, elevated levels of homocysteine has been identified as an important risk factor for AD and inheritance of the ε4 allele of ApoE has been identified as a risk factor for both sporadic AD and DLB. Both of these risk factors, as well as well as elevated levels of $A\beta_{1-42}$, have been implicated in promoting oxidative stress.

Lipids are a major target of free radical attack, which leads to lipid peroxidation. A variety of products of lipid peroxidation are formed. The present inventors have focused on the characterization of isoprostanes (IsoPs). IsoPs are prostaglandin-like compounds that are formed non-enzymatically in vivo by free radical-induced peroxidation of arachidonic acid (AA) (C20:4ω6). The first class of IsoPs discovered had a prostaglandin F-type cyclopentane ring structure ($F_2$-IsoPs). Intermediate in the formation of IsoPs are labile bicyclic $PGH_2$-like endoperoxides ($H_2$-IsoPs), which are reduced to form $F_2$-IsoPs. The present inventors have found that thiols catalyze this reduction both in vitro and in vivo. However, this reduction is not entirely efficient, allowing rearrangement of $H_2$-IsoPs in vivo to form E-ring and D-ring IsoPs and also isothromboxanes. The present inventors have also shown that IsoP-like compounds are formed from oxidation of docosahexaenoic acid (DHA) (C22:6ω3). Because DHA is highly enriched in neurons these compounds are termed neuroprostanes (NeuroPs). The impetus for characterizing the formation of NeuroPs derived from the hypothesis that measurement of NeuroPs may provide a uniquely sensitive index of oxidative neuronal injury owing to the fact that DHA is highly enriched in neurons and is much more oxidizable than AA. Analogous to the IsoPs, $F_4$-, $E_4$-, and $D_4$-NeuroPs are formed in brain in vivo.

Evidence for enhanced formation of products of lipid peroxidation in AD is formidable. The present inventors have reported that levels of $F_2$-IsoPs are significantly increased in lumbar cerebrospinal fluid (CSF) from living patients with probable AD and that both $F_2$-IsoPs and $F_4$-NeuroPs are significantly increased in postmortem ventricular CSF from patients with documented AD, compared to levels in aged-matched controls. The finding of increased levels of $F_2$-IsoPs in CSF from living patients with probable AD suggests that oxidant injury is an early event in this disease. The present inventors have also found that levels of $F_4$-NeuroPs are increased approximately two-fold in the hippocampus, superior and medial temporal gyri, and inferior parietal lobe of AD brain compared to aged-matched controls. Importantly, however, no significant differences were found in the cerebellum, an area of the brain that is unaffected by AD pathology.

Lipid peroxidation also generates a number of reactive aldehydes, including 4-hydroxy-2-nonenal (HNE), malondialdehyde (MDA), and acrolein. Interest in these aldehydes derives from the fact that they are reactive molecules that adduct and covalently modify proteins and DNA. Levels of these aldehydes have also been found to be increased in AD. The present inventors discovered a series of γ-ketoaldehydes that are orders of magnitude more reactive than any other known product of lipid peroxidation. Moreover, these compounds exhibit a unique proclivity to crosslink proteins to an extent that is not shared by these other aldehydes. These compounds are formed as rearrangement products of $H_2$-IsoP and $H_4$-NeuroP endoperoxides (FIG. 1). Originally, the present inventors called these products isolevuglandins to emphasize their similarity to the cyclooxygenase-derived γ-ketoaldehydes, levuglandins $E_2$ and $D_2$. However, to these compounds have been subsequently referred to as isomeric ketoaldehydes, shortened to isoketals (IsoKs), to emphasize their chemical structure.

Oxidation of AA in vitro produces both $F_2$-IsoPs and IsoKs in nearly equivalent amounts. However, comparison of the formation of $F_2$-IsoPs and IsoKs in vivo is more complex, because IsoKs rapidly adduct to lysyl residues on proteins. FIG. 2 shows the time course of disappearance of free IsoK and HNE during an incubation with bovine serum albumin, which provides an index of the rate of adduction to the protein. Notably, the IsoK adducted to albumin with extreme rapidity, being essentially complete within a few minutes. In striking contrast, approximately 50% of the HNE still remained in free form after 80 minutes.

The above findings explained why repeated attempts in the past to detect free IsoKs during oxidation of biological systems in vitro, e.g. microsomes, and in animal models of oxidant injury in vivo were unsuccessful because they are rapidly sequestered as protein adducts. Therefore, the present inventors undertook to determine the identity of IsoK lysyl adducts as a basis for development of methodology to detect IsoK and NeuroK adducts in biological tissues in their adducted form. It was found that IsoKs adduct to lysines forming a pyrrole, which readily undergoes autoxidation to form stable lactam and hydroxylactam adducts (FIG. 3). Reversible Schiff base adducts were also identified. Schiff base adducts are formed rapidly and then decline over time, whereas lactam adducts accumulate slowly over time. Lysyl protein adducts of IsoKs and NeuroKs are analyzed by LC/MS/MS following enzymatic digestion of proteins to individual amino acids. Enzymatic digestion of proteins is necessary because the adducts degrade during acid hydrolysis. However, this analysis is further complicated by the proclivity of IsoKs and NKs to induce protein crosslinking, which is resistant to hydrolysis. This is demonstrated following incubation of ovalbumin (OVA) with 10 molar equivalents of IsoK for about 4 hours. This results in the formation of extensive cross-linked high molecular weight oligimers. In striking contrast, no cross-linking was observed following incubation of 10 molar equivalents of HNE with ovalbumin (FIG. 4). This is a dramatic example of the differential effects of IsoKs/NKs and HNE on protein adduction and cross-linking.

Without being bound by theory or mechanism, the above observations show that IsoKs/NeuroKs are the most attractive products of lipid peroxidation heretofore identified as candidates that may be responsible for neuronal injury and protein aggregation in AD and other dementias associated with oxidative stress. The extent to which $H_2$-IsoPs undergo rearrangement depends on cellular efficiency to reduce them. Therefore, the amounts of IsoKs and NeuroKs formed depends not only on the amount of $H_2$-IsoPs formed but also cellular reduction conditions. This is an important consideration when choosing therapeutic interventions to suppress the formation of IsoKs and NeuroKs. In this regard, thiol antioxidants would not only suppress the amount of $H_2$-IsoPs/$H_2$-NeuroPs formed but also effectively reduce them to $F_2$-IsoPs/$F_4$-NeuroPs, thereby preventing their rearrangement to IsoKs/NeuroKs. Therefore, thiol antioxidants would likely be more effective than non-thiol containing antioxidants in reducing the formation of IsoKs/NeuroKs.

Thus, an aspect of the present invention is a method of suppressing the formation of IsoKs/NeuroKs by administering an effective amount of thiol antioxidants.

The present inventors have also demonstrated overproduction of IsoPs in another neurodegenerative disease, including AD and Huntington's disease. Thus, IsoKs and NeuroKs are believed to participate in the oxidative neuronal injury that occurs in these and other neurodegenerative diseases.

Risk factors for AD include increasing age, inheritance of genetic mutations that increase levels of $A\beta_{1-42}$, inheritance of the ApoE4 allele, vitamin deficiencies that increase levels of homocysteine, and head injury. Without being bound by theory or mechanism, the key commonality of these risk factors is that they cause oxidative stress with attendant IsoK and/or NeuroK overproduction in the hippocampus and surrounding areas of brain, which initiates alterations in protein function leading to cellular dysfunction and death. Using immunohistochemistry with an antibody against IsoK protein adducts, the present inventors have obtained evidence that IsoK adducts in the hippocampus from patients with AD are specifically localized to neurons and neuropil. Importantly, neuronal IsoK immunoreactivity is absent in areas of brain from patients with AD that are unaffected by AD pathology (cerebellum) and in the hippocampus from aged-matched controls.

Specific mutations in the amyloid precursor protein (APP) have been characterized in some inherited forms of early-onset AD, particularly in one Swedish family (APPswe). These mutations lead to a substantial increase in the levels of the $A\beta_{1-42}$ in brain and spinal fluid. $A\beta_{1-42}$ is toxic to cultured neuronal cells, but the mechanism for this toxicity is still somewhat controversial. One potential mechanism is the production of free radicals, since incubating amyloid peptide with neuronal membranes has been shown to induce lipid peroxidation. There have been conflicting reports regarding the presence of increased amounts of lipid peroxidation products in amyloid deposits. However, soluble $A\beta_{1-42}$ rather than $A\beta_{1-42}$ in deposits is probably more capable of inducing lipid oxidation.

Folate, vitamin B6, and vitamin B12 are important cofactors in the homocysteine/methionine conversion cycle. Therefore, deficiencies in these vitamins increase homocysteine levels. Folate, vitamin $B_6$, vitamin $B_{12}$ deficiencies and hyperhomocysteinemia have been reported to be risk factors for AD. In certain at risk populations, from 10 to 30% of elderly persons may be folate or vitamin $B_{12}$ deficient. A number of studies link hyperhomocysteinemia to increased lipid peroxidation. The present inventors have recently shown that even small increases in homocysteine levels in normal humans are positively and significantly correlated with plasma concentrations of $F_2$-IsoPs. This finding has since been confirmed independently by Davi et al. One proposed mechanism for the link between homocysteine levels and oxidative stress is the participation of the thiol group in redox cycling of copper, which leads to formation of hydrogen peroxide formation and the formation of highly toxic hydroxyl radicals via Fenton chemistry. This can be markedly accelerated in the presence of cysteine. Homocyteine has also been shown to potentiate $A\beta$ mediated neuronal toxicity.

In addition to the role of vitamin B6 in the homocysteine/methionine cycle, vitamin B6 deficiency itself has been found to be an independent risk factor for AD. This suggests that vitamin B6 may play an additional role in limiting oxidative damage.

The present inventors have discovered that key members of the vitamin B6 family, pyridoxamine (PM), salicylamine (SM), etc., acts to trap reactive aldehydes formed during lipid peroxidation, especially IsoKs/NeuroKs. Effectively sequestering these aldehydes as adducts with PM prevents them from adducting to key cellular proteins. In fact, data demonstrates the efficacy by which pyridoxamine prevents IsoKs from adducting to proteins.

Whereas APPswe mice fed a normal diet do not exhibit neurodegenration, Kruman et. al. recently found that placing APPswe mice on a folate deficient diet enriched with homocysteine induced significant neurodegeneration in the CA3 region of the hippocampus, which did not occur in wild-type mice fed the same diet. The folate deficient/homocysteine enriched diet did not increase amyloid deposition. At present, nothing is known about the combined effects of hyperhomocysteinemia and ApoE4 in vivo on lipid peroxidation, proteasome activity, protein aggregation, or behavioral deficits.

Inheritance of the ε4 allele of ApoE (ApoE4) is associated with poorer cognitive performance with age and is currently the only known genetic risk factor for sporadic AD. Inheritance of ApoE4 may also be a genetic risk factor for (DLB). Homozygosity for ε4 is associated with increased oxidative damage in hippocampal pyramidal cells. In the brain, ApoE protein is produced by astrocytes and microglial cells and then secreted as part of lipoprotein particles. ApoE lipoprotein is recognized and internalized by the LDL receptor-related protein (LRP), which in brain is primarily expressed on neuronal cells, including hippocampal pyramidal neurons. ApoE has been identified immunohistochemically within neurons, where it is proposed to interact with microtubule associated proteins, including tau. ApoE3 lipoproteins induce neurite outgrowth in primary neuronal cultures, whereas ApoE4 lipoproteins do not, a process that requires recognition by LRP. For this reason, ApoE3 appears to enhance the ability of neurons to recover from injury. In keeping with this hypothesis, inheritance of ApoE4 increases risk of neurological deficits following head injury.

While numerous studies have demonstrated that genetic ablation of the mouse ApoE gene increases lipid peroxidation in various tissues, it is important to recognize that the presence of the E4 allele, and not complete deficit of the ApoE gene, is the actual risk factor for AD. Therefore, to study the effect of ApoE4 in vivo requires ablating the endogenous mouse ApoE gene and then inserting human ApoE4 as a transgene. Several variants of ApoE4 mice have been generated by placing the transgene under the control of different promoters, including human glial fibrillary acidic protein (gfap-ApoE4), human apoe (apoe-ApoE4), neuron-specific enolase (nse-ApoE4), mouse Thy1 (thy-ApoE4), or the human PDGF-β gene (pdgf-ApoE4). The effect of the transgene is promoter dependent and the appropriate promoter is somewhat controversial. Nonetheless, as ApoE protein is found in both neuron and astroglial cells, the effects of the various transgenes do reveal potential effects in each cell type. Significant dendritic alterations occur in pyramidal neurons of apoe-ApoE4 mice accompanied by poorer performance in Morris water maze tests compared to wild-type or ApoE3 mice. Aged gfap-ApoE4 mice show profound changes in performance on the radial arm test of working memory, but do not have increased levels of senile plaque compared to wild-type mice. Injection of kainic acid at doses that do not induce neurodegeneration in nse-ApoE3 mice results in significant neurodegeneration in nse-ApoE4 mice. Aged thy-ApoE4 and pdgf-ApoE4 mice, but not gfap-ApoE4 mice, show hyperphosphorylation of tau and ubiquitin-positive inclusions. In summary, all ApoE4 mice have some forms of neurological deficit with individual variations in their effects on neurodegeneration and protein aggregation. Because gfap-ApoE4 mice produce ApoE4 in astrocytes, the major source of ApoE production, the present inventors have chosen these mice to study the effects of ApoE4 on lipid peroxidation, protease function, and neurodegeneration.

Currently, it is believed that animal models provide the most effective means to compare temporal alterations in protein function that may result from oxidative neuronal injury with the onset of dementia. However, examination of human post-mortem tissue frames expectations for what alterations in protein function are important in dementia. As discussed below, several cellular functions are altered in AD for which there is in vitro evidence that oxidative injury can induce similar alterations. These include altered protease activity, altered cytoskeletal organization, and altered cholinergic function. Therefore, the present invention allows for the determination whether or not these proteins are adducted by IsoKs and/or NeuroKs in AD and if adduction of these proteins precede the onset of diminished mental function in animal models of dementia.

Aggregated ubiquinated proteins is a prevailing feature of many neurodegenerative diseases and dementias. In AD, these take the form of senile plaques and neurofibrillary tangles. In DLB, these aggregates primarily consist of α-synuclein. The cause of protein aggregation is not well understood, but the presence of ubiquitinated proteins suggests a defect in the ubiquitin/proteasome pathway. Indeed, reduced proteasome activity is a common feature of many neurodegenerative diseases. Reduced chymotrypsin-like and post-glutamyl peptidase activity of the proteasome has been found in short post-mortem interval autopsied brains from patients with AD, compared to age and sex-matched controls. The decrease in proteasome activity in AD brain appears to be due to a functional deficiency, rather than decreased proteasomal subunit expression.

Proteins can be degraded by the proteasome via 2 independent pathways, both of which are relevant to oxidized proteins and proteins modified by products of lipid peroxidation. The most common pathway is tagging proteins with ubiquitin by specific E2 and E3 ubiquitinating enzymes. The criteria for recognition and tagging of proteins by E2/E3 is a matter of intense investigation, but remains unknown for many proteins. Only multi-ubiquinated proteins are recognized and degraded by the 26S proteasome. The 26S proteasome consists of two major complexes, the 20S proteasome and either 11S or 19S regulatory subunits. The regulatory subunits recognize and unfold ubiquinated proteins, allowing them to enter into the catalytic core of the 20S proteasome. The 20S proteasome is composed of 7 alpha and 7 beta subunits and has three major protease activities: chymotrypsin-like activity, trypsin-like activity, and post-glutamyl peptidase activity. While the 26S proteasome degrades the majority of proteins, the 20S proteasome can function independently to degrade oxidized and denatured proteins. Proteasome inhibitors such as lactacystin and various peptide-aldehydes act by reacting with the catalytic subunits of the 20S proteasome, and thereby inhibit both 20S and 26S proteasome activity.

The underlying mechanism(s) responsible for impaired proteasome function in AD is unclear, but a unifying link between the occurrence of enhanced oxidant injury and impaired proteasome function is a plausible hypothesis. Exposure of fibroblasts to an oxidative stress in the form of 40% oxygen over a period of 12 wks leads to decreased proteasome activity via the formation and accumulation of aggregated lipofuscin/ceroid. Injection of ferric nitrilotriacetate into mice leads to lipid peroxidation and a transient decrease in proteasome activity. Oxidative stress produces at least three products that have been demonstrated to inhibit proteasome activity: reactive oxygen species, hydroxynonenal (HNE), and IsoKs. Of these, only the IsoKs have effects at submicromolar concentrations.

While reduced proteasome activity might directly account for accumulation of aggregated proteins intracellularly, the converse might also be true, that is that aggregated proteins might inhibit proteasome function. This not only would lead to further accumulation of protein aggregates, but potentially might also induce programmed cell death. The latter notion is supported by the findings that synthetic proteasome inhibitors induce apoptosis in neurons, probably through the accumulation of proapoptotic signals such as p53. In summary, lipid peroxidation, protein aggregation, and inhibition of proteasome function may be casually linked and intertwined, which in concert could lead to neurodegeneration.

In addition to the proteasome, another protease whose activity has been shown to be reduced by approximately 50% in AD is insulin degrading enzyme (IDE). IDE degrades not only insulin but also $A\beta_{1-42}$ peptide. Very recent studies have demonstrated that genetic ablation of IDE increases brain $A\beta_{1-42}$ levels. Addition of insulin to IDE inhibits amyloid degradation by IDE, and increases secreted levels of $A\beta_{1-42}$ in neuro2A cells. IDE strongly associates with the proteasome and addition of insulin to IDE also inhibits proteasomal chymotrypsin-like activity through an unknown mechanism. Because of this relationship, alterations in IDE activity in vivo might also effect proteasomal activity or vice versa. If IsoK or NeuroK adduction of IDE inhibits its activity, it is conceivable that $A\beta_{1-42}$ levels would increase and proteasome activity would decrease, accounting for two major findings in AD. For this reason, determining whether IDE activity decreases in animal models of AD and whether changes in activity correlate with IDE adduction by IsoKs/NeuroKs is an aspect of the present invention.

Another major protease activity in AD in calpain, which is increased in the disease. Calpain cleavage of the precursor of cdk5 activates cdk5, which phosphorylates tau. Calpain also cleaves tau, but not phosphorylated-tau or paired helical filament (PHF)-tau. Therefore, increased calpain activity could lead to increased phosphorylation of tau, a prerequisite for PHF-tau formation. Interestingly, oxidative injury and amyloid β both have been shown to increase calpain activity, which potentially may link levels of amyoid β and oxidative stress to PHF-tau formation.

Neurofibrillary tangles (NFT), which are comprised primarily of ubiquinated aggregates of PHF-tau, are a defining feature of AD. PHF-tau is phosphorylated at several well-characterized sites. In vitro, tau promotes microtubule assembly, stabilizes cellular microtubules, affects their dynamic behavior, and may play an important role in regulating microtubule interactions with membranes. Formation of the abnormal tau aggregates, PHF-tau and NFT, therefore may lead to the loss of normal neuronal structure and function. The underlying process that leads to the formation of PHF-tau and NFT formation in AD is currently unknown. One plausible hypothesis is that products of lipid peroxidation modify phosphorylated tau, preventing its degradation and thereby facilitating its aggregation. In support of this hypothesis, incubation of phosphorylated tau with products of lipid peroxidation, e.g. HNE, can induce the epitope for Alz50, an antibody that recognizes an AD-specific conformational epitope on PHF-tau. Furthermore, HNE inhibits dephosphorylation of tau in primary rat hippocampal cells. Immunohistochemical studies have also localized both immunoreactive HNE and acrolein to neurofibrillary tangles. As mM concentrations of HNE are required to induce the Alz50 epitope on tau, more reactive products of lipid peroxidation, such as IsoKs and NeuroKs, may be more attractive candidates involved in initial modification of tau in AD. Important in that regard is that we have found that adduction of IsoKs to tau does induce the Alz50 epitope.

The cellular function of microtubules include axonal and dendritic growth and support of sympatic activity. Ultrastructural analysis of cortical neurons suggest abnormalities of the cytoskeleton in AD. The underlying cause of this disruption is unknown, but products of lipid peroxidation, e.g. HNE, have been hypothesized to play a role. Incubation of mouse neuroblastoma Neuro2A cells with HNE results in disruption of microtubule organization and inhibition of neurite outgrowth. When cytoplasmic proteins from these cells were examined, HNE adducts were found on both tubulin and tau protein. Since one of the major functions of tau protein is to organize tubulin filaments, these experiments suggest that adduction of these proteins is responsible for microtubule disruption. Presumably, adduction of tubulin by IsoKs or NeuroKs would similarly disrupt microtubule organization.

Impairments in cholinergic neurotransmitter systems of the basal forebrain are a hallmark of Alzheimer's disease pathophysiology. The deficit in acetylcholine synthesis results from reduction in choline acetyltransferase activity. Reduction of acetyltranferase activity is greater than the loss of cholinergic neurons. Therefore, neuronal death may be a result of, not the cause of, the reduction in acetytransferase activity. Interestingly, exposure of neuronal cells in culture to HNE or subjecting them to an oxidative stress has been shown to decrease choline acetyltransferase activity. However, in the case of the former, it is not known whether this effect is a result of adduction of the enzyme by HNE or impairment of transcription of the choline acetyltransferase gene.

There are two Nerve Growth Factor (NGF) receptors, trkA and P75NGFR. Both NGF receptors localize to cholinergic neurons in the hippocampus and NGF receptors are depleted in AD. Although trkA mRNAs are decreased in AD, loss of NGF binding appears to precede the loss of TrkA immunoreactivity and neuronal loss, suggesting that at least some of the loss of receptor function is due to receptor modification. Exposure of neuronal cultures to hydrogen peroxide or $A\beta_{1-42}$ reduces the level of trkA protein, suggesting that oxidative injury may play a role in receptor loss.

In summary, there are a number of known proteins that are thought to play important functions in either the progression of AD or protection against the disease and whose function is altered in AD. Therefore, aspects of the present invention include the determination that these proteins in AD brain and brain from an animal model of a risk factor for AD are adducted by IsoKs and/or NeuroKs.

Purely for exemplary purposes, the following non-inclusive aspects of the present invention are discussed. These embodiments should not be considered as limiting, and other embodiments as would be obvious to one of ordinary skill in the are to be considered as part of this invention and not departures therefrom.

A first aspect of the present invention is to provide a method for assessing the formation of IsoK and NeuroK adducts quantitatively and qualitatively in AD brain.

A second aspect of the present invention is a method to assess potential causative factors involved in age-related dementia. This may include the use of ApoE null mice transgenically expressing human ApoE4 by evaluating the brain levels of $F_2$-IsoPs, $F_4$-NeuroPs, and levels and distribution of IsoK and NeuroK adducts.

A third embodiment of the present invention is a method to determine the role of oxidative stress/injury in general and specifically the role of IsoK/NeuroK adduct formation by using pharmacologic interventions that include effective amounts of at least one of antioxidants, Tempol, and lipoic acid.

A fourth aspect of the present invention is a method of identifying the proteins adducted by IsoKs and NeuroKs in the hippocampus of brains from patients with AD and in ApoE4 Tg mice fed a normal or folate deficient/homocysteine enriched diet. This may include determining whether there is enhanced adduction of the following proteins by IsoKs and NeuroKs: tau, tubulin, proteasome subunits, insulin degrading enzyme, acetylcholine acyltransferase, ApoE, and neuronal growth factor receptors.

One embodiment of the present invention is a method of treating and/or preventing oxidative damage that comprises administering an effective IsoK/NeuroK adduct formation suppressing amount of a phenolic amine compound and/or a pyridoxamine compound.

Another embodiment of the present invention is a method of preventing myocardial damage that comprises administering a damage preventing effective amount of phenolic amine compound or a pyridoxamine analog or salicylamine analog.

Another embodiment of the present is a method of preventing cardiac sodium channel dysfunction, inactivation, and/or blocking that comprises administering an effective amount of a phenolic amine compound and/or a pyridoxamine analog or salicylamine analog.

Another embodiment of the present invention is a method of preventing or treating ventricular fibrillation and/or arrhythmias that comprises administering an effective amount of a phenolic amine compound and/or a pyridoxamine analog or salicylamine analog.

Yet another embodiment of the present invention is a method of preventing or retarding the progression of neurodegenerative disease that comprises administering an effective oxidative stress preventing or decreasing amount of a phenolic amine compound and/or a pyridoxamine or salicylamine compound. The neurodegenerative disease of this or other embodiments may include, but is not limited to, Parkinson's disease, Alzheimer's disease, Huntington's disease and/or dementia.

Another embodiment of the present invention is a method of preventing or retarding the progression of oxidative stress associated with vascular dementia or stroke, comprising administering an effective oxidative stress preventing or decreasing amount of a phenolic amine compound and/or a pyridoxamine or salicylamine compound.

Any of these embodiments may include the use of a pyridoxamine, salicylamine, tyrosine compound or an analog thereof. Examples of these compounds or analogs include, but are not limited to, compounds selected from the formula:

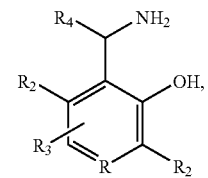

wherein:
R is N or C;
$R_2$ is independently H, substituted or unsubstituted alkyl;
$R_3$ is H, halogen, alkoxy, hydroxyl, nitro;
$R_4$ is H, substituted or unsubstituted alkyl, carboxyl; or analogs thereof.

BRIEF DESCRIPTION OF THE DRAWINGS

FIG. 46 shows characterization of the potency and selectivity of pyridoxamine derivatives for scavenging gamma ketoaldehydes.

DETAILED DESCRIPTION OF THE INVENTION

As stated above, an embodiment of the present invention is to provide a method of treating and/or preventing oxidative damage, comprising administering an effective IsoK/NeuroK adduct formation suppressing amount of a phenolic amine compound of the present invention.

In a preferred embodiment, that compounds is a salicylamine compound or an analog thereof.

Another embodiment of the present invention is a method of preventing myocardial damage, comprising administering a damage preventing effective amount of phenolic amine compound of the present invention.

Another embodiment of the present invention is a method of preventing cardiac sodium channel dysfunction, inactivation, and/or blocking, comprising administering an effective amount of a compound of the present invention.

Another embodiment of the present invention is a method of preventing or treating ventricular fibrillation and/or arrhythmias, comprising a compound of the present invention.

Another embodiment of the present invention is a method of preventing or retarding the progression of neurodegenerative disease, comprising administering an effective oxidative damage preventing or decreasing amount of a compound of the present invention. The neurodegenerative may be chosen from, for example, Parkinson's disease, Alzheimer's disease, Huntington's disease, dementia.

Another embodiment of the present invention is a method of preventing or retarding the progression of oxidative damage associated with vascular dementia or stroke, comprising administering an effective oxidative damage preventing or decreasing amount of a compounds of the present invention.

Another embodiment is to provide a method for accessing the formation of IsoK and NeuroK adducts quantitatively and qualitatively in AD brain. This embodiment can comprise determining whether levels of IsoK and NeuroK protein adducts are increased in CSF from patients with AD compared to age-matched controls. This method may be used to obtain a single chain antibody against NeuroK lysyl adducts and/or determine the localization of IsoK and NeuroK adducts in AD brain and other age-related dementias.

The term "therapeutically effective amount" or "effective amount" refers to that amount of a compound of the present invention that is sufficient to effect treatment, as defined below, when administered to a mammal in need of such treatment. The therapeutically effective amount will vary depending upon the subject and disease condition being treated, the weight and age of the subject, the severity of the disease condition, the manner of administration and the like, which can readily be determined by one of ordinary skill in the art.

The term "treatment" or "treating" means any treatment of a disease in a mammal, including, for example: (i) inhibiting the disease, that is, arresting the development of clinical symptoms; and/or (ii) relieving the disease, that is, causing the regression of clinical symptoms.

Figure 1:
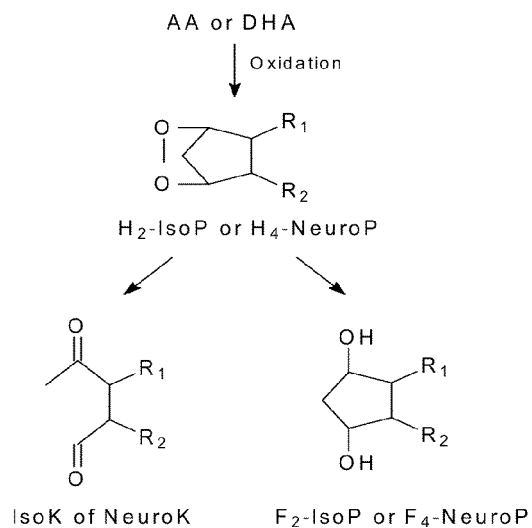
FIG. 1 is a scheme showing compounds formed as rearrangement products of $H_2$-IsoP and $H_4$-NeuroP endo peroxides.
Figure 1A:
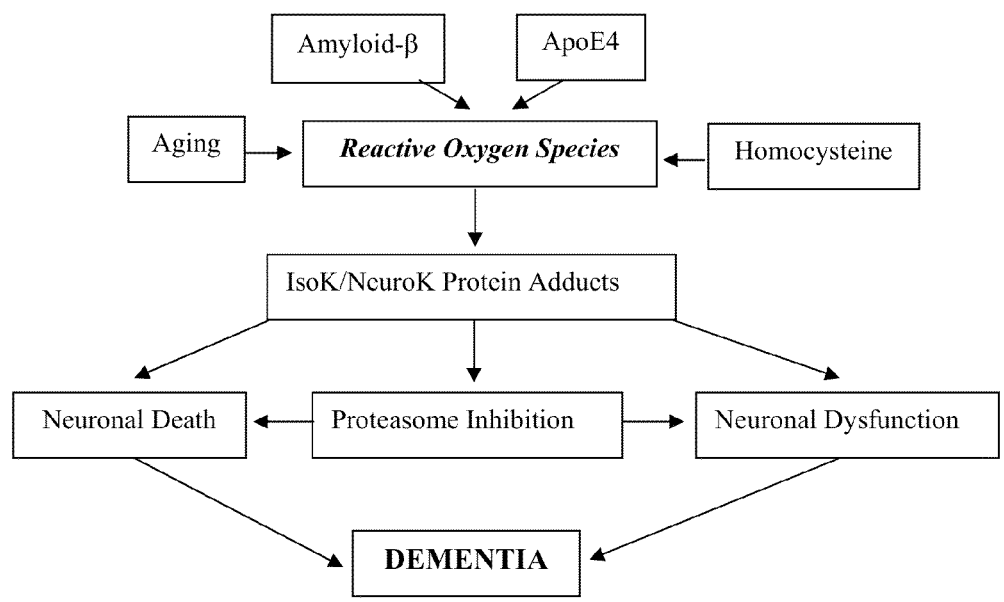
FIG. 1a is a flow chart demonstrating the relationship between dementia and oxidated stress.
Figure 2:
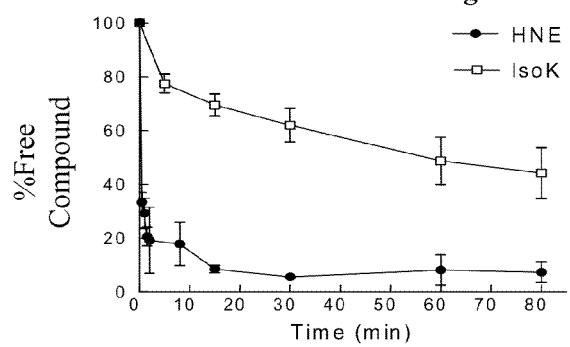
FIG. 2 is a graph showing the time course of disappearance of free IsoK and HNE.
Figure 3:
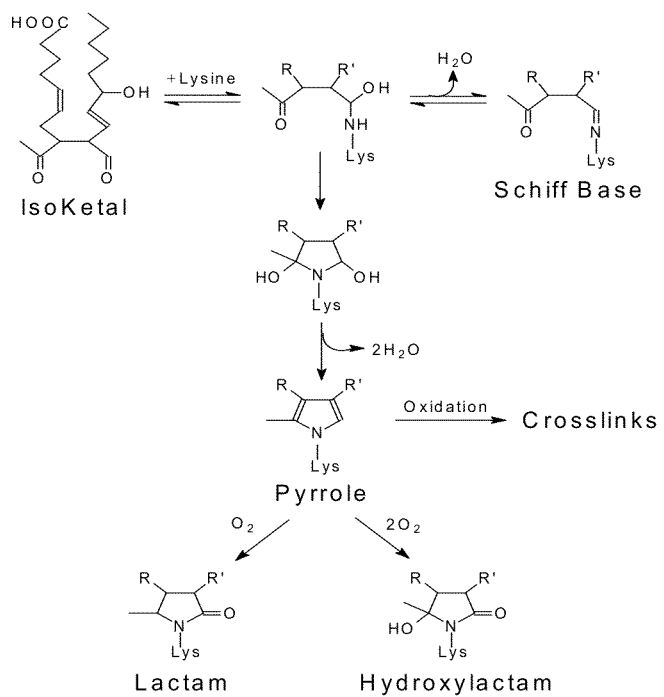
FIG. 3 is a scheme showing that IsoKs adduct to lysines.
Figure 4:
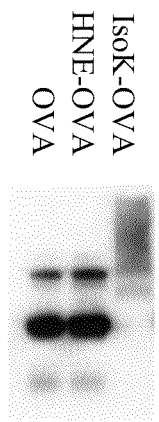
FIG. 4 is a Western blot showing the proclivity of IsoKs and NKs to induce protein crosslinking.
Figure 5:
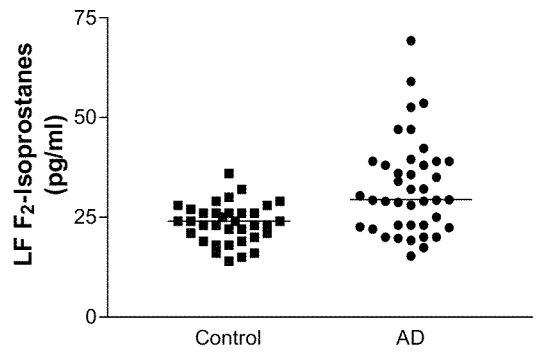
FIGS. 5-11 are graphs showing data in connection with the present invention.
Figure 6:
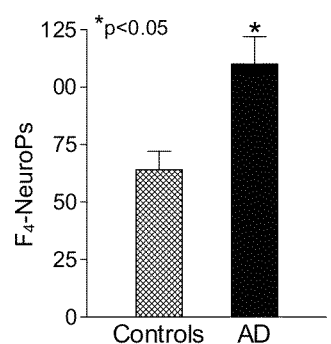

The present inventors have discovered that levels of $F_2$-IsoPs and $F_4$-NeuroPs are significantly increased in AD brain, and that in studies both in vitro and in vivo, IsoK and NeuroK formation parallels the formation of $F_2$-IsoPs and $F_4$-NeuroPs, respectively. FIG. 5 shows CSF $F_2$-IsoP concentrations in 41 living patients with probable AD and 35 aged matched controls. The average time since diagnosis for the AD patients was less than two years. CSF $F_2$-IsoP concentrations were approximately 38% higher in probable AD patients compared to aged-matched controls ($p<0.001$). CSF $F_4$-NeuroP levels were 72% higher in patients with probable AD compared to aged-matched controls ($p<0.05$) (FIG. 6.) The relative increase in $F_4$-NeuroP CSF levels in AD patients compared to controls was greater than that for $F_2$-IsoPs. This helps show that oxidative injury is localized to neurons and with the fact that DHA is more easily oxidized than AA, and suggests that lipid peroxidation occurs early in the course of the disease and is not a post-mortem artifact.

Figure 7:
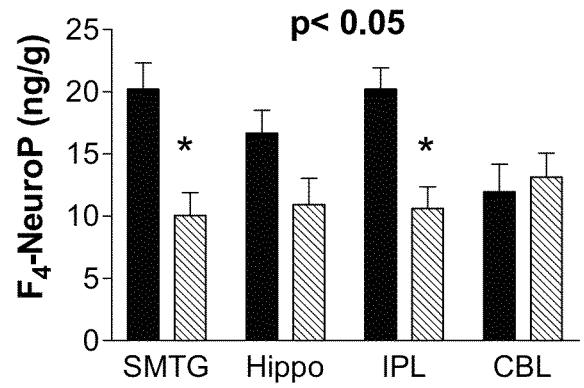

The present inventors examined AD brain by region, and found that $F_4$-NeuroPs were elevated about two-fold in the hippocampus (Hippo), superior and medial temporal gyrus (SMTG), and inferior parietal lobe (IPL) of AD brain (solid bars) compared to the same regions of brain from aged-matched controls (hatched bars). Importantly, however, no significant differences were found in the cerebellum (CBL), an area of brain unaffected by AD pathology (FIG. 7). When $F_2$-IsoPs were measured in these regions, all three affected regions were increased, although only IPL reached statistical significance (not shown). Measurement of $F_4$-NeuroPs provides a more sensitive indicator of oxidative injury in the brain than measurement of $F_2$-IsoPs.

Figure 8:
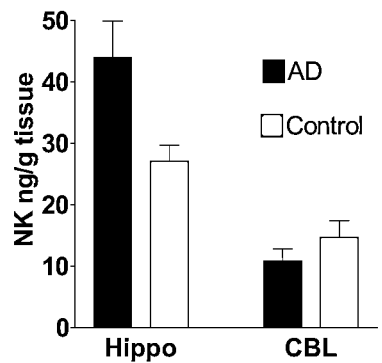

It appears that that there would be a concomitant increase in the formation of IsoKs and NeuroKs in settings where the formation of $F_2$-IsoPs and $F_4$-NeuroPs are enhanced, because they derive from the same respective endoperoxide intermediates. Because the present inventors had found that levels of $F_4$-NeuroPs esterified in brain from AD patients were increased to a greater extent than $F_2$-IsoPs, they undertook to determine if NeuroK adducts were increased in AD brain compared to levels measured in age-matched control brains. FIG. 8 shows that levels of NeuroK-lysyl-lactam protein adducts in the hippocampus from six AD patients were significantly increased compared to six aged-matched controls (p<0.02). Again, and importantly, as was found with NeuroPs, no significant difference was found in the level of NeuroK adducts between AD brain and controls in an area of brain unaffected by AD pathology, the cerebellum.

Antibodies are required to determine the location of adducts in AD brain. The present inventors obtained an antibody against IsoK lysyl adducts by pursuing a single chain antibody (ScFv) strategy, rather than the standard polyclonal antibody approach. Without being bound by theory, extensive adduction of the immunizing protein, which would also induce substantial cross-linking of the protein. Crosslinking would alter the protein's conformation and probably expose buried epitopes on the immunizing protein unrelated to the actual adducts. Therefore, antibodies generated by this method would not be specific to the IsoK adduct. In contrast, screening of phage-displayed antibodies can be done with extremely short peptides, eliminating conformational changes.

Figure 9:
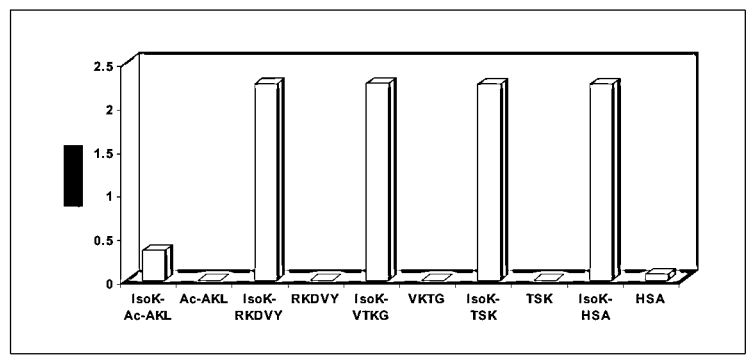

A simplified synthesis of IsoKs based on the available method for the preparation of levuglandin E2. In this regard, the present inventors, to obtain a single chain antibody, adducted biotinylated-gly-ser-gly-lys peptide with excess synthetic IsoK. The preparation was then purified using a Waters Oasis HLB cartridge. Our Molecular Recognition Core, directed by Dr. Ray Memaugh, then used this adducted peptide to screen a phage-display library of antibody sequences, which resulted in several clones with antibodies that bound to the peptide. The clone with the highest apparent binding, D11 ScFv, was chosen for further study. To test whether D11 ScFv recognized the IsoK adduct and not specific sequences, we used synthetic IsoK to adduct a series of short peptides with unrelated sequences: acetylated-ala-lys-leu (AcAKL), arg-lys-asp-val-tyr (RKDVY), val-thr-lys-gly (VTKG), and thr-ser-lys (TSK). The present inventors also adducted human serum albumin (HSA). Both unadducted and adducted peptides were coated on 384 well ELISA plates prior to blocking and D11 ScFv added. All ScFv antibodies in our Molecular Recognition Core contain a peptide sequence, the E-tag, which is recognized by an anti-E antibody conjugated to horseradish peroxidase. After washing the plates, anti-E antibody, conjugated to horseradish peroxidase (AntiE-HRP), was added. D11 recognized only the adducted forms of all four of the peptides and HSA (FIG. 9). The lower binding to acAKL is probably due to relatively poor binding of the acetylated peptide to the ELISA plate. An unrelated ScFv, A10, did not bind to either adducted or unadducted peptides (not shown). These data indicated that D11 ScFv recognizes the IsoK adduct independent of any specific amino acid sequence.

Figure 10:
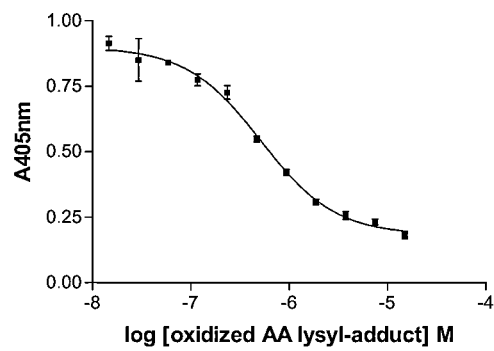

To confirm that D11 ScFv would recognize the lysyl IsoK adduct derived from the oxidation of AA, AA is oxidized in the presence of radiolabeled lysine. IsoK-adducted lysine is separated from unadducted lysine and other products of AA oxidation using sequential elution from a Sep-Pak C18 cartridge. Then a competitive ELISA is performed as follows: IsoK-RKDVY peptide was coated on 384-well ELISA plates for 1 hour. The plates were then blocked and increasing concentrations of adducted lysine incubated with a fixed concentration of D11 ScFv. After washing the plates, bound D11 ScFv was detected by AntiE-HRP. As shown in FIG. 10, the soluble IsoK lysyl adducts derived from oxidation of AA competed away D11 ScFv binding to immobilized IsoK-RKDVY.

Figure 11:
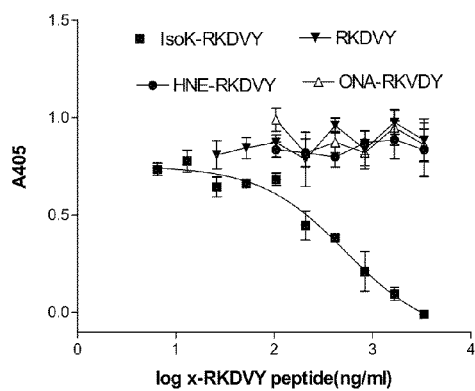

Because oxidation of arachidonic acid produces other reactive aldehydes, including HNE and 4-oxo-nonenal (ONA), D11 ScFv cross-reactivity with these products is tested. The present inventors adducted RKDVY peptide with either synthetic IsoK (IsoK-RKDVY), HNE (HNE-RKDVY), or ONA (ONA-RKDVY). Like IsoK, ONA forms pyrrole adducts but lacks one of the long acyl side chains of IsoK. The ability of D11 ScFv to bind each peptide using completive ELISA as before is tested (FIG. 11). While soluble IsoK-RKDVY competed for D11 ScFv binding, neither RKDVY peptide alone, HNE-RKDVY, or ONA-RKDVY are effective. In additional experiments, 15-$F_{2t}$-IsoP (8-iso-$PGF_{2\alpha}$) and human serum albumin also did not compete for D11 ScFv binding (not shown). These results demonstrate that D11 ScFv binds specifically to IsoK lysyl adducts.

Figure 12:
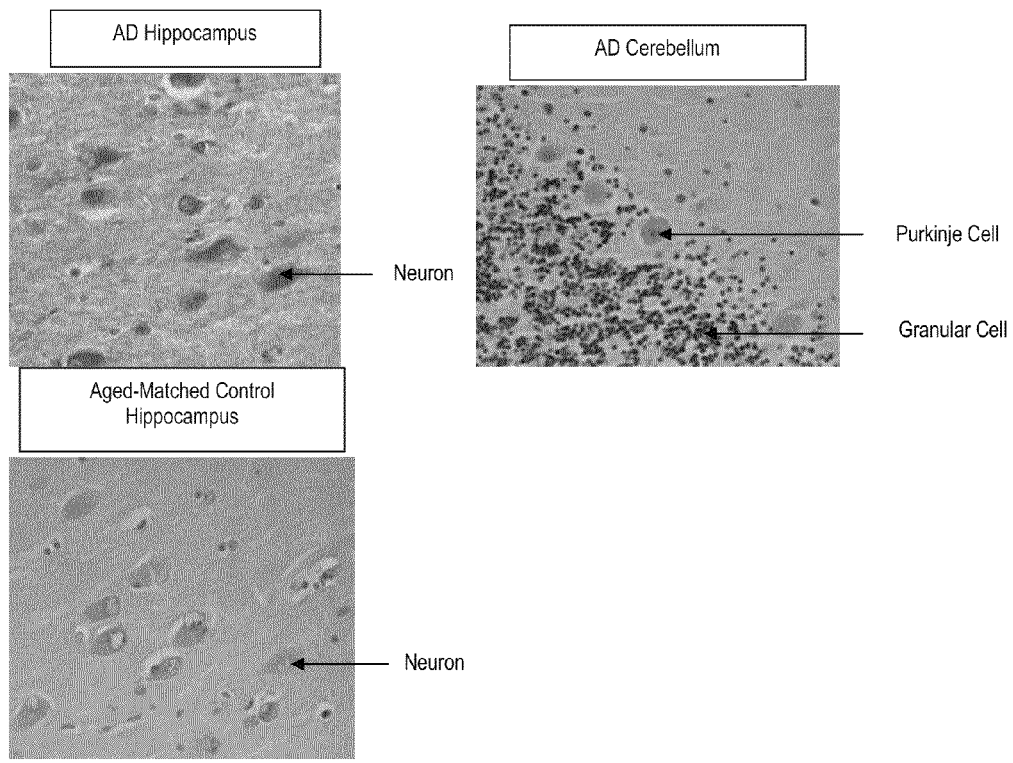
FIG. 12 is a series of color photographs showing staining of hippocample pyramidal neurons.

The present inventors examined the location of IsoK adducts in the hippocampus of AD brain by immunohistochemistry using D11 ScFv. Paraffin embedded sections were stained using D11 ScFv (FIG. 12). There is staining of hippocampal pyramidal neurons that are localized to the neuron soma and neuropil. The staining was specific for neurons in that staining of glial cells was not observed. The present inventors then examined hippocampal sections in aged-matched controls. Remarkably, we found no neuronal staining in the controls. We also examined cerebellum sections from AD brain and no staining was observed. This was an important control for the specificity of hippocampal neuronal staining since the cerebellum is unaffected by AD pathology. To ensure that the immunoreactivity in AD brain hippocampus was specific for IsoK adducts, the staining after pre-incubating with either RKDVY peptide or IsoK-RKDVY peptide is repeated. Pre-incubation with IsoK-RKDVY completely ablated D11 ScFv immunoreactivity. However, pre-incubation with RKDVY peptide was ineffective (not shown). These results strongly support the notion that the D11 ScFv immunoreactivity is highly specific for IsoK adducts. Overall, these studies suggest that the accumulation of IsoK, and possibly NeuroK, adducts are a distinguishing feature of AD.

Another aspect of the present invention is a method to assess potential causative factors involved in age-related dementia. This may include the use of ApoE null mice transgenically expressing human ApoE4 fed either a normal diet or a folate deficient/homocysteine enriched diet by evaluating at least one of performance on memory tests, brain levels of $F_2$-IsoPs, $F_4$-NeuroPs, and levels and distribution of IsoK and NeuroK adducts, activities of brain proteasome, calpain, and insulin degrading enzyme, brain levels of amyloid $\beta_{1-40}$ and $A\beta_{1-42}$, and the extent and localization of neurodegeneration.

Figure 13:
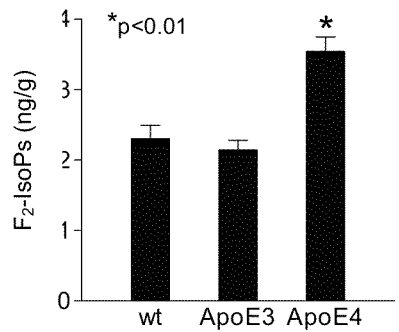
FIGS. 13-15 are graphs showing data in connection with the present invention.

An example of an animal model to replicate features of AD and DLB is genetically altered mice with the risk factor for AD, ApoE4. These mice lack the mouse gene for ApoE and are hemizygous for the є4 allele of human ApoE. Human ApoE is expressed in astrocytes in these mice under the control of the GFAP promoter. These {ApoE−/−, ApoE4+} mice display significantly increased cerebral levels of $F_2$-IsoPs at 12-16 months compared {ApoE−/−, ApoE3+} mice, whose levels were not statistically different from wild type mice (FIG. 13). This increased cerebral oxidative damage was also found to be age dependent; cerebral $F_2$-IsoPs were no different between {ApoE−/−, ApoE4+}, {ApoE−/−, ApoE3+} and wild type mice at 7 months of age (not shown).

Figure 14:
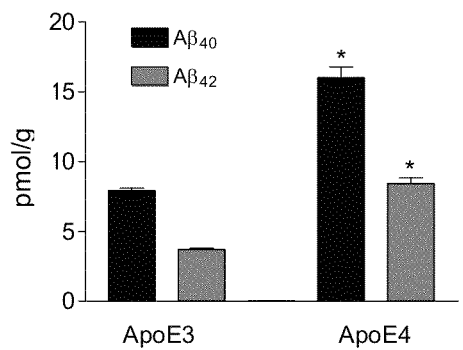

Of great interest is that it has recently been shown that these GFAP {ApoE−/−, ApoE4+} mice, but not GFAP {ApoE−/−, ApoE3+} mice, have profound impairment in terms of their acquisition performance on the working memory protocol used with the radial arm maze test when tested at a similar point during aging in which we observed increased levels of $F_2$-IsoPs (11-14 months of age). Since human ApoE isoforms have been proposed to influence Aβ metabolism, cerebral levels of $Aβ_{1-40}$ and $Aβ_{1-42}$ were determined. As shown in FIG. 14, extractable cerebral $Aβ_{1-40}$ and $Aβ_{1-42}$ levels were significantly increased in {ApoE−/−, ApoE4+} mice compared to (ApoE−/−, ApoE3+) mice which were not different from wild type mice (not shown). This was also found to be age-dependent in that no differences in levels of the Aβ peptides were found between all 3 groups of mice at age 6 months (not shown). This data suggests that increased cerebral oxidative damage is associated with increased concentrations of extractable mouse Aβ peptides in the absence of plaque formation.

This shows that mice with 2 risk factors for sporadic AD, advancing age and inheritance of ApoE4 have both increased oxidative damage and increased Aβ production. This brings together 4 characteristic features of sporadic AD pathogenesis: advancing age, inheritance of ApoE4, increased Aβ peptide production, and increased cerebral oxidative damage.

Figure 15:
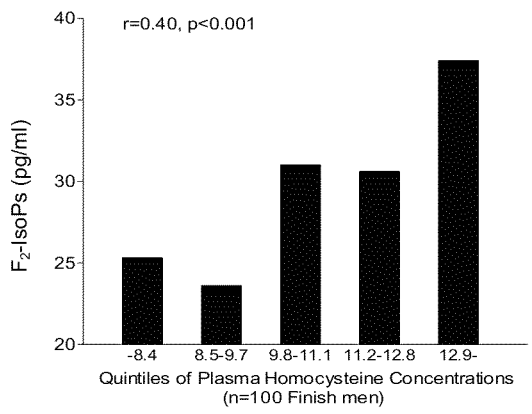

As mentioned previously, hyperhomocysteinemia is a strong risk factor for AD, APPswe mice fed a folate deficient diet supplemented with homocysteine exhibited neurodegeneration in the hippocampus, which was not observed in APPswe mice fed a normal diet, and that homocysteine can promote oxidative stress. Pertinent to this is observations that plasma concentrations of $F_2$-IsoPs are positively correlated with plasma concentrations of homocysteine over the quintile of homocysteine levels measured in normal adult human males (FIG. 15). The coefficient for association was 0.40 ($p<0.001$). An independent study by Davi et. al. also found a linear increase in urinary $F_2$-IsoP levels with increasing plasma homocysteine levels in patients with hyperhomocysteinemia.

Figure 16:
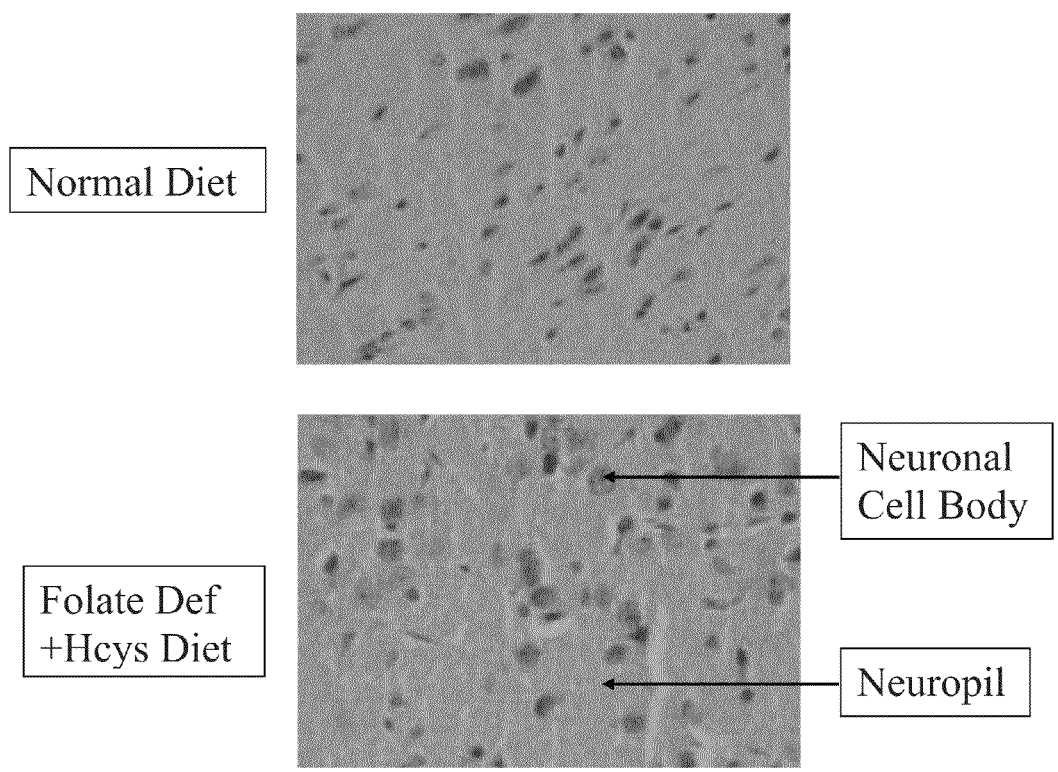
FIG. 16 is a color photograph showing immunohistochemistry of IsoK adducts in the cerebral cortex of tested mice.
Figure 17:
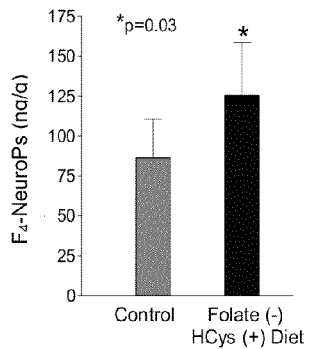
FIGS. 17-27 are graphs showing data in connection with the present invention.

To explore the effect of homocysteine on brain IsoK adduct formation, the present inventors performed immunohistochemistry for IsoK adducts in the cerebral cortex of folate deficient weanling mice fed a diet supplemented with homocysteine for 5 weeks. Immunoreactivity in many neurons of these mice were found, which was absent in mice fed a normal diet (FIG. 16). The inventors also fed normal mice the same folate deficient/homocysteine supplemented diet that Kruman et. al. fed to APPswe mice for 1 month and measured levels of $F_4$-NeuroPs in the brains. $F_4$-NeuroPs were found to be significantly increased in the brains of these mice compared to mice fed a normal diet (FIG. 17). There appears to be a strong correlation between homocysteine and oxidative stress and feeding a folate deficient/homocysteine enriched diet to APPswe mice led to hipocampal neurodegeneration that was absent in APPswe mice fed a control diet.

In examining the relationship between oxidant injury in the brain in general and IsoK/NeuroK adduct formation specifically on hippocampal proteasome function and neurodegeneration, the present inventors discovered that IsoKs and IsoK-adducted proteins/peptides can have effects on proteasome function.

Figure 18:
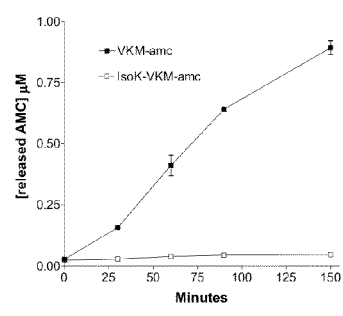
Figure 19:
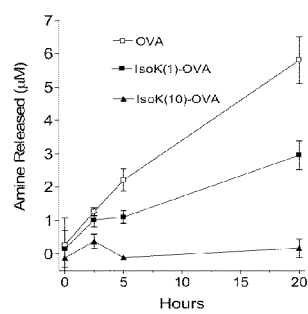

Reactive oxygen species and HNE are known to inhibit proteasome function. However, concentrations of HNE required to have an effect on proteasome function are usually in the mM range. Therefore, the inventors tested whether the far more reactive IsoKs would induce similar effects at substantially lower concentrations using a synthetic $E_2$-IsoK, which is a mixture of stereoisomers with the same basic structure as levuglandin E2. When equimolar $E_2$-IsoK was adducted to a fluorogenic proteasome substrate, VKM-amc, (IsoK-VKM-amc) the hydrolysis of the adducted peptide by proteasome containing cell lysates was essentially abolished (FIG. 18). In contrast, adduction with similar concentrations of HNE had no effect on hydrolysis (data not shown). Adduction of a model protein, ovalbumin (OVA), which contains ten surface lysines with equimolar $E_2$-IsoK (IsoK(1)-OVA), reduced its degradation by purified 20S proteasome nearly in half (FIG. 19). Adduction of all surface lysines with ten molar equivalents of $E_2$-IsoK [IsoK(10)-OVA] completely blocked its degradation. These experiments demonstrate that IsoK adduction of peptides and proteins can prevent their degradation by the proteasome, indicating that adduction of tau or other proteins in vivo would block their degradation as well, leading to their accumulation and aggregation.

Figure 20:
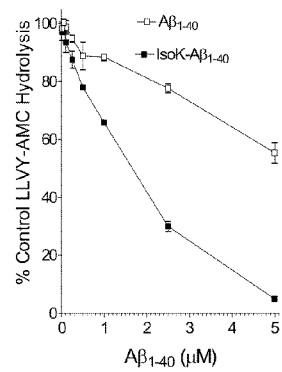

Because nondegradable substrates often act as competitive inhibitors, the inventors tested whether $E_2$-IsoK adducted proteins would inhibit proteasome chymotrypsin-like activity as measured by hydrolysis of a fluorogenic substrate, LLVY-amc. $Aβ_{1-40}$ is known to inhibit 20S proteasome activity, but adduction with $E_2$-IsoK (IsoK-$Aβ_{1-40}$) greatly potentiated the ability of the peptide to inhibit proteasome activity by approximately 5-fold ($IC_{50}$ 1.3 μM) (FIG. 20).

Figure 21:
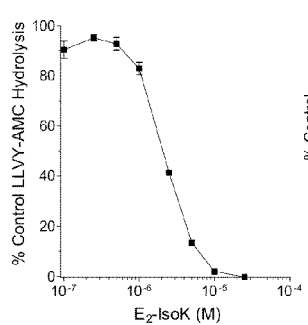

To test the effects of IsoK adduction within the milieu of intracellular proteins that would occur in vivo, $E_2$-IsoK to RAW cell lysates was added and it inhibited chymotrypsin-like activity with an $IC_{50}$ of 2.1 μM (FIG. 21). When the mechanism of inhibition id analyzed, both competitive and non-competitive mechanism are found. Therefore, in addition to adducted proteins inhibiting the proteasome, IsoKs may cause inhibition by directly adducting to the proteasome itself, or to proteins that regulate proteasome activity.

Figure 22:
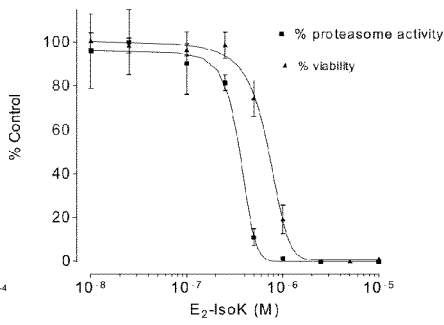

Because inhibitors of proteasome function induce neuronal death, the present inventors examined the toxicity of IsoKs. When $E_2$-IsoK was added to P19 neuroglial cultures, it potently induced both proteasome inhibition ($IC_{50}$ 330 nM) and cell death ($LC_{50}$ 670 nM) (FIG. 22). These results indicate that formation of IsoKs and NeuroKs in the brain, particularly in the presence of excess amyloid, will lead to a considerable reduction in proteasome function, as in seen in AD.

Figure 23:
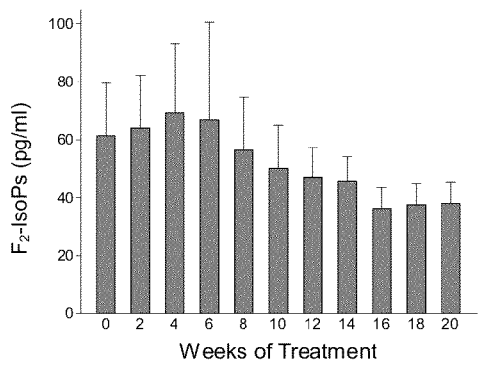
Figure 24:
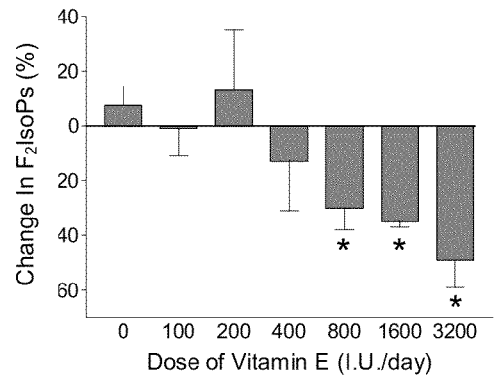

The use of antioxidants to suppress oxidative injury: An important aspect of antioxidant clinical trials that has not received sufficient attention until recently, is the scientific rational for the choice of a particular antioxidant to test, the dose to test, and the duration of treatment. Often times, when a clinical trial fails to show significant efficacy for an antioxidant, no effort has been made to ensure that the dose of the antioxidant tested effectively suppressed oxidant injury. The importance of having such information is highlighted by our studies defining the clinical pharmacology of vitamin E. First, the present inventors found that sixteen weeks of vitamin E supplementation was required to reach the plateau in maximum suppression of plasma concentrations of $F_2$-IsoPs in subjects with hyperocholesterolemia (FIG. 23). This was a key finding because the literature is abound with studies in which have vitamin E was administered for less than 10 weeks to determine its effects on some pathologic process. Also important is the finding that supplementation with vitamin E for 18 weeks had no significant effect on $F_2$-IsoP levels at doses below 800 I.U./d and the effect of 800 I.U./d was remarkably small, it reduced levels only about 10% (FIG. 24). This is an important finding because many studies of the effects of vitamin E have used doses of 400 I.U./d and observed no benefit. Administration of vitamin E at higher doses for 18 weeks dose-dependently suppressed plasma concentrations of $F_2$-IsoPs further, but the maximum suppression observed, at the extremely high dose of 3200 I.U./d was only 49%. This data suggests that the effectiveness of vitamin E to suppress oxidative stress in vivo is not as great as many had previously thought. This may, however, explain why the administration of 2000 I.U./d to patients with AD only had a modest effect to slow the progression of the disease. Nonetheless, these findings would suggest that it would be sagacious to test the efficacy of other antioxidants to suppress oxidant injury in patients with AD and in animal models of AD.

Figure 25:
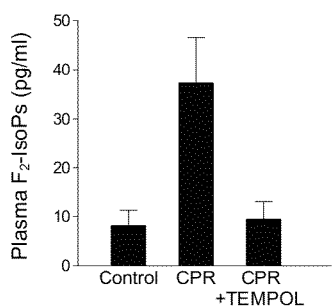
Figure 26:
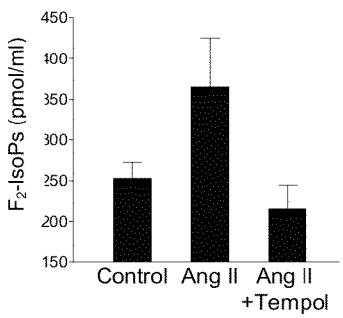

The present inventors chose antioxidants to test in the models of AD that we have found effective in suppressing oxidative stress in other animal models of oxidative injury. One model of oxidative injury is the porcine model of global ischemia/reperfusion resulting from induction of cardiac arrest for 3 mins followed by cardiopulmonary resuscitation (CPR). Shown in FIG. 25 are results using this model. As shown, cardiac arrest followed by CPR induced a dramatic increase in plasma concentrations of $F_2$-IsoPs. Intravenous injection of 30 mg/kg of Tempol, a superoxide dismutase mimetic, during CPR prior to defibrillation and reperfusion completely ablated this increase in plasma levels of $F_2$-IsoPs. This study involved the administration of a single dose of Tempol. Shown in FIG. 26 is data taken from a report from Ortiz, et. al. in which they assessed the ability of chronic oral administration of TEMPOL (1 mM in the drinking water) to suppress the increase in $F_2$-IsoPs induced by chronic IV infusion of angiotensin II. Tempol completely prevented the increase in levels of $F_2$-IsoPs in renal vein plasma. Tempol is one of the antioxidants of the present invention.

Figure 27:
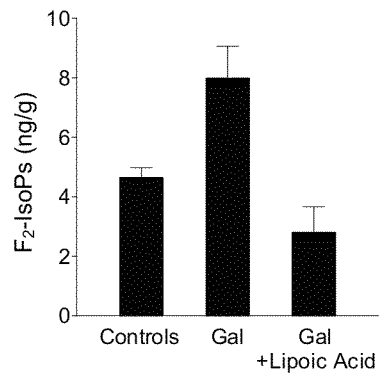
Figure 28:
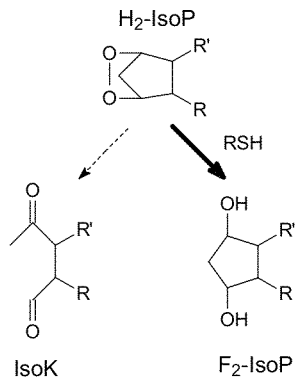
FIG. 28 is a scheme showing formation of IsoK and $F_2$-IsoP.

Another antioxidant of the present invention is lipoic acid. This antioxidant has been shown to be effective in improving cognitive impairment in aged SAMP mice that have been found to have increased levels of Aβ. The inventors have found it to be highly effective in suppressing the increase in formation of $F_2$-IsoPs in the kidney of a model of human hepatorenal syndrome, galactosamine treated rats (FIG. 27). Treatment of rats with galactosamine was associated with a significant increase in levels of $F_2$-IsoPs esterified in the kidney which was completely suppressed to below control levels in rats treated with lipoic acid (1 g/L drinking water). Dihydrolipoic acid is a dithiol. As mentioned previously, thiols reduce the endoperoxide intermediates in the IsoP pathway in vivo to $F_2$-IsoPs. Reducing the endoperoxides concomitantly therefore reduces the formation of endoperoxide rearrangement products, one of which is the IsoKs (FIG. 28). Therefore, mechanistically lipoic acid is an antioxidant to test in animal models of AD. It is also an antioxidant to test because it is available over the counter for human use.

Another embodiment of the present invention is the use of pyridoxamine and/or pyridoxamine analogs to prevent IsoK/NeuroK from adducting to proteins. This is a novel approach to mitigate the deleterious effects of adduction of IsoKs/NeuroKs to proteins. Without being bound by theory, pyridoxamine and/or an analog thereof prevents the adduction of these reactive products of lipid peroxidation selectively by acting as a surrogate amine for adduction rather than acting as an antioxidant to suppress the formation of IsoKs/NeuroKs. Pyridoxamine has been shown to prevent the formation of advanced glycation endproducts (AGE) in diabetes by trapping reactive carbonyl intermediates in the formation of AGEs. It is in Phase II trials in patients with diabetes where high plasma concentrations are achieved with this drug and no toxicity has been observed.

Figure 29:
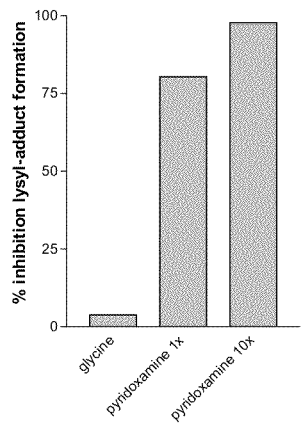
FIGS. 29-32 are graphs showing data in connection with the present invention.
Figure 30:
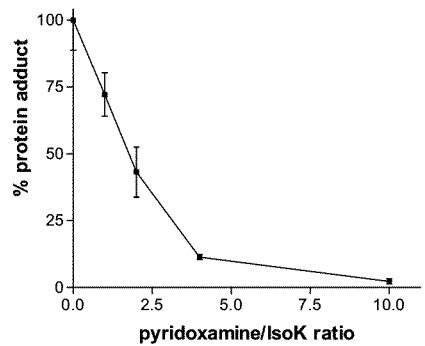

The present inventors have explored the ability of pyridoxamine, salicylamine, and/or analogs thereof to prevent adduction of IsoKs to lysine and proteins, including attempts to prevent adduction of IsoKs to lysine using other amines, e.g. glycine, but found that they were ineffective (FIG. 29). This may be understood because rate of adduction of IsoKs to the ε-amino group of lysine is much faster than its rate of adduction to the α-amino group. In contrast, pyridoxamine is effective in preventing adduction to lysine (FIG. 29). Even a 1:1 ratio of IsoK:pyridoxamine was ~80% effective in preventing IsoK from adducting to lysine and a 1:10 ratio completely prevented IsoK adduction to lysine. This is an important finding because plasma concentrations of pyridoxamine in patients treated with the drug are very high, approximately 100 μM. Then the ability of pyridoxamine to prevent IsoK adduction to a protein, ovalbumin was tested (FIG. 30). It was found that the presence of a 10-fold molar excess of pyridoxamine completely blocked any IsoK adduction of the proteins. The ability of pyridoxamine to prevent adduction to proteins appeared to be less efficacious compared to adduction to free lysine. Without being bound by theory, this may be explained by differences in the reactivity of some lysine groups in the local environment of proteins. Nonetheless, plasma concentrations with supplementation of pyridoxamine are in the range of 100-fold above expected endogenous concentrations of IsoKs/NeuroKs, far in excess of those required to prevent protein adduction. These findings suggested that the amino group on pyridoxamine is reactive and more than the ε-amino group of lysine. The present inventors determined the approximate second order rate constants of different amines for pyrrole formation with 4-oxypentanal, a γ-ketoaldehyde. The rate constants are as follows: $N^\alpha$acetyllysine ($70\times10^6$ $M^{-1}s^{-1}$), 2-aminoethanol ($310\times10^6$ $M^{-1}s^{-1}$), 4-picolinylamine ($1,100\times10^6$ $M^{-1}s^{-1}$), and pyridoxamine ($53,200\times10^6$ $M^{-1}s^{-1}$). 4-Picolinylamine has the structure of pyridoxamine without the $CH_2OH$, OH, and $CH_3$ phenyl ring substituents. These findings help explain why pyridoxamine and/or an analog thereof is so effective in trapping IsoKs, preventing them from adducting to lysine residues.

Embodiments of the IsoK scavengers/compounds of the present invention have excellent oral pharmacokinetics, are non-toxic, and passes the blood-brain barrier.

Any of these embodiments may include the use of a pyridoxamine, salicylamine, tyrosine compound or an analog thereof. Examples of these compounds or analogs include, but are not limited to, compounds selected from the formula:

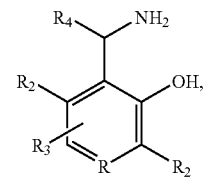

wherein:
  R is N or C;
  $R_2$ is independently H, substituted or unsubstituted alkyl;
  $R_3$ is H, halogen, alkoxy, hydroxyl, nitro;
  $R_4$ is H, substituted or unsubstituted alkyl, carboxyl; or analogs thereof.

The term "alkyl" group includes a straight or branched saturated aliphatic hydrocarbon chain having from 1 to 8 carbon atoms, such as, for example, methyl, ethyl, propyl, isopropyl (1-methylethyl), butyl, tert-butyl (1,1-dimethylethyl), and the like. The alkyl groups may optionally be interrupted in the chain by a heteroatom, such as, for example, a nitrogen or oxygen atom, forming an alkylaminoalkyl or alkoxyalkyl group, for example, methylaminoethyl or methoxymethyl, and the like.

The term "alkoxy" group includes an alkyl group as defined above joined to an oxygen atom having preferably from 1 to 4 carbon atoms in a straight or branched chain, such as, for example, methoxy, ethoxy, propoxy, isopropoxy (1-methylethoxy), butoxy, tert-butoxy (1,1-dimethylethoxy), and the like.

The compounds or analogs also may be chosen from:

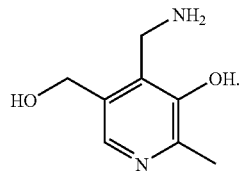

The compounds or analogs may chosen from:

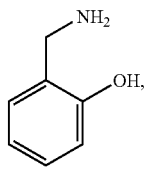

or an analog thereof

The compounds or analogs may also be chosen from:

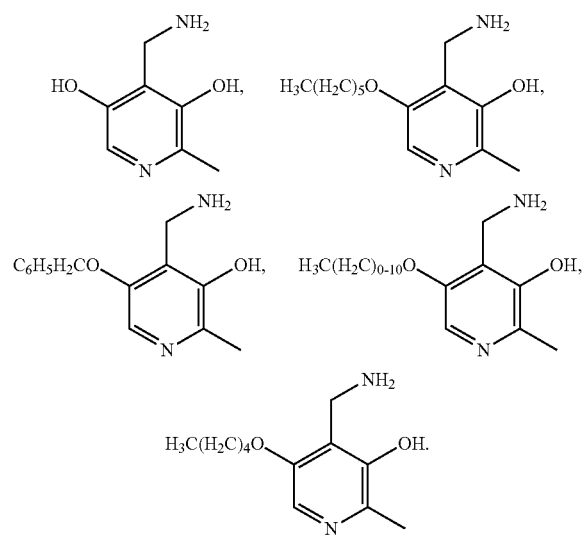

or an analog thereof.

The compounds or analogs may also be chosen from:

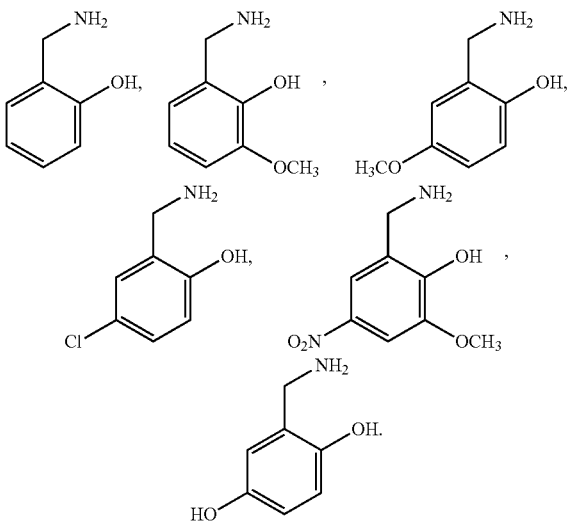

or an analog thereof

The compounds may also be chosen from:

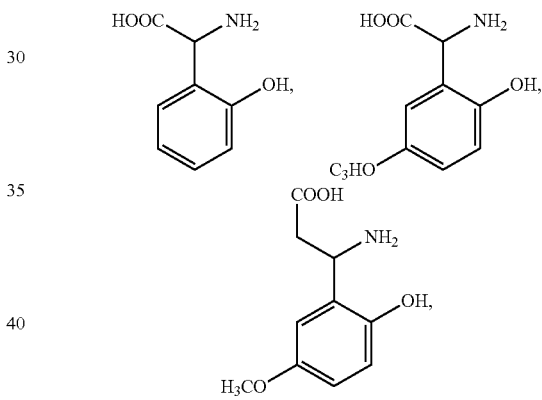

or an analog thereof.

For the purposes of the present invention, the terms pyridoxamine, pyridoxamine compounds, and pyridoxamine analogs can be considered to have alike meaning in terms of, for example, their presence in compositions, dosages, etc.

The compounds of the present invention can be administered as the sole active pharmaceutical agent, or can be used in combination with one or more other agents useful for treating or preventing various complications, such as, for example, AD and other neurodegenerative diseases. When administered as a combination, the therapeutic agents can be formulated as separate compositions that are given at the same time or different times, or the therapeutic agents can be given as a single composition.

The compounds of the present invention may be made up in a solid form (including granules, powders or suppositories) or in a liquid form (e.g., solutions, suspensions, or emulsions). They may be applied in a variety of solutions and may be subjected to conventional pharmaceutical operations such as sterilization and/or may contain conventional adjuvants, such as preservatives, stabilizers, wetting agents, emulsifiers, buffers etc.

For administration, the compounds of the present invention are ordinarily combined with one or more adjuvants appropriate for the indicated route of administration. For example, they may be admixed with lactose, sucrose, starch powder, cellulose esters of alkanoic acids, stearic acid, talc, magnesium stearate, magnesium oxide, sodium and calcium salts of phosphoric and sulphuric acids, acacia, gelatin, sodium alginate, polyvinylpyrrolidine, and/or polyvinyl alcohol, and tableted or encapsulated for conventional administration. Alternatively, they may be dissolved in saline, water, polyethylene glycol, propylene glycol, carboxymethyl cellulose colloidal solutions, ethanol, corn oil, peanut oil, cottonseed oil, sesame oil, tragacanth gum, and/or various buffers. Other adjuvants and modes of administration are well known in the pharmaceutical art. The carrier or diluent may include time delay material, such as glyceryl monostearate or glyceryl distearate alone or with a wax, or other materials well known in the art.

In therapeutic applications, the compounds of the present invention may be administered to a mammalian patient in an amount sufficient to reduce or inhibit the desired indication. Amounts effective for this use depend on factors including, but not limited to, the route of administration, the stage and severity of the indication, the general state of health of the mammal, and the judgment of the prescribing physician. The compounds of the present invention are safe and effective over a wide dosage range. However, it will be understood that the amounts of pyridoxamine actually administered will be determined by a physician, in the light of the above relevant circumstances.

Pyridoxamine may be administered by any suitable route, including orally, parentally, by inhalation or rectally in dosage unit formulations containing conventional pharmaceutically acceptable carriers, adjuvants, and vehicles, including liposomes. The term parenteral as used herein includes, subcutaneous, intravenous, intraarterial, intramuscular, intrasternal, intratendinous, intraspinal, intracranial, intrathoracic, infusion techniques, intracavity, or intraperitoneally. In a preferred embodiment, pyridoxamine is administered orally or parentally.

Pharmaceutically acceptable acid addition salts of the compounds suitable for use in methods of the invention include salts derived from nontoxic inorganic acids such as hydrochloric, nitric, phosphoric, sulfuric, hydrobromic, hydriodic, hydrofluoric, phosphorous, and the like, as well as the salts derived from nontoxic organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, trifluoroacetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are salts of amino acids such as arginate and the like and gluconate, galacturonate, n-methyl glutamine, etc. (see, e.g., Berge et al., J. Pharmaceutical Science, 66: 1-19 (1977).

The acid addition salts of the basic compounds are prepared by contacting the free base form with a sufficient amount of the desired acid to produce the salt in the conventional manner. The free base form may be regenerated by contacting the salt form with a base and isolating the free base in the conventional manner. The free base forms differ from their respective salt forms somewhat in certain physical properties such as solubility in polar solvents, but otherwise the salts are equivalent to their respective free base for purposes of the present invention.

Figure 31:
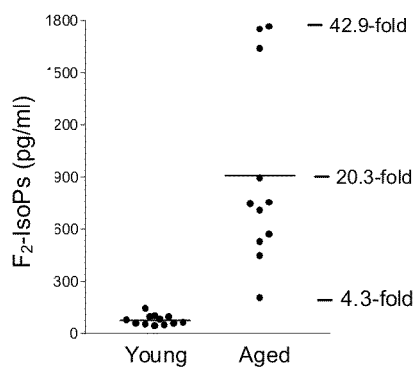

As mentioned, age is a risk factor for dementia and AD. A number of studies have suggested that oxidative stress is increased in animals during aging measuring various indices of oxidative stress. However, increases in levels measured in aged animals compared to young animals have been only 2 to 3-fold or less higher. The present inventors have measured levels of $F_2$-IsoPs in plasma of aged rats (22-24 mo) and young animals (3-4 mo) and found that the mean increase in plasma concentrations of $F_2$-IsoPs in aged animals compared to young animals was 20.3-fold (range 4.3 to 42.9-fold) (FIG. 31).

An embodiment of the present invention is a method of selecting proteins that are thought to be important in modulating the progression of AD are adducted by IsoKs and NeuroKs.

Figure 32:
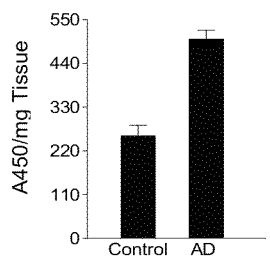

One method of the present invention to examine specific proteins to use as anti-IsoK and anti-NeuroK lysyl adduct antibodies to perform sandwich ELISA. In an example of this method, an antibody to a target protein is used to coat the plate, the sample is then added, and presence of IsoK adduct is detected with D11 ScFv (or anti-NeuroK ScFv) and anti-E HRP. To test the feasibility of this approach, the present inventors adducted commercially available recombinant tau (Sigma) with synthetic IsoK. Sandwich ELISA using a commercially available anti-tau antibody (Zymed) is them performed. Various concentrations of IsoK-tau were added, and various concentrations of D11 ScFv were used to optimize binding conditions. An assay using homogenates from brain from AD patients and aged-matched controls (FIG. 32) was then performed. Hippocampus from AD brain exhibited about a 2-fold greater immunoreactivity than aged-matched control hippocampus. These results demonstrate feasibility of rapidly screening for adducts of selected proteins by ELISA. Importantly also is that this data suggests that one of the proteins thought to be important in the pathogenesis of AD, namely tau, is one of the proteins that is adducted by IsoKs in AD.

Figure 33:
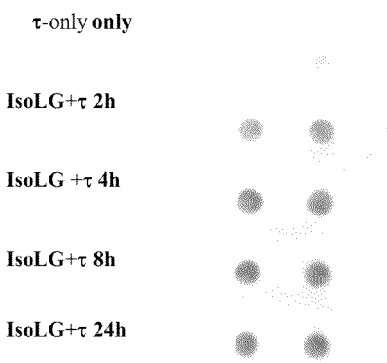
FIG. 33 shows Alz50 immunoactivity.

Because these data suggested that IsoKs adduct to tau in vivo, the present inventors examined whether IsoK adduction of tau would enhance the formation of PHF-tau. Synthetic IsoK to equimolar amounts of recombinant human tau was added and the amount of PHF-tau formation by dot blot analysis was determined with the monoclonal antibody Alz50 (a gift from Dr. Peter Davis). Alz50 recognizes an epitope unique to PHF-tau. The inventors found that incubation of tau with IsoK generated strong Alz50 immunoreactivity within 2 hrs. (FIG. 33). This result suggests that IsoK adduction of tau plays an important role in PHF-tau formation during progression of AD.

After an initial screening by ELISA, the identity of adducts on the protein may be confirmed by an alternative method. Mass spectrometry, particularly when coupled with fragmentation and product mass analysis, is a rapid and effective method of sequencing peptides from protein tryptic digests. Peptides generally fragment at the backbone carbon bond positions, so that specific mass losses identify the amino acid sequence of the peptide.

Figure 34:
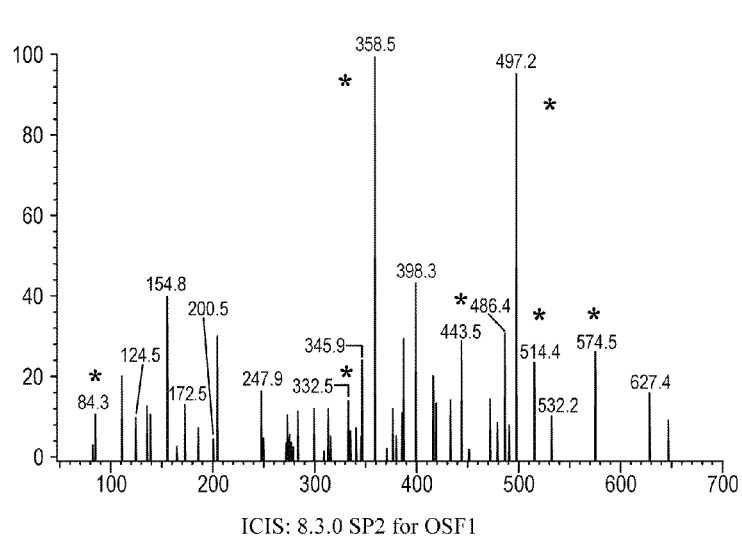
FIG. 34 shows mass spectrometry results.
Figure 35:
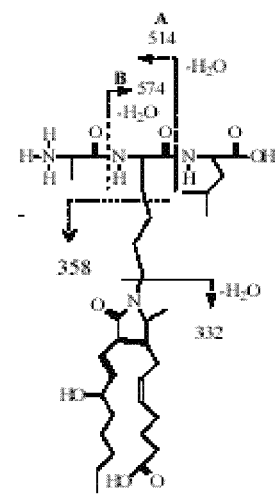
FIG. 35 peptide bond fragmentation.

The present inventors subjected two adducted peptides to electrospray ionization (ESI) mass spectrometry followed by collisionally-induced disassociation (CID) and a second round of mass spectrometry. ESI LC/MS/MS of the IsoK-acAKL (mass 663) gave a number of product ions including those with m/z 574, 514, 497, 443, 358, 332, and 84 (FIG. 34). We interpret fragmentation at peptide bond A (FIG. 35) to yield m/z 514, and fragmentation at peptide bond B to yield m/z 574. The m/z 497 ion is formed by the additional loss of the α-amino group (17 a.m.u.) from 514. Fragmentation at both peptide bonds A and B yields m/z 443. Fragmentation of the lysyl-lactam bond yields m/z 358, 332, and 84. These results suggested that fragmentation of adducted peptides do yield product ions that would identify both the peptide sequence and the presence of lysyl adducts. To test this possibility, we fragmented a second adducted peptide, IsoK-VTKG (mass 795). Again it was determined that product ions would allow identification of peptide sequence, along with the expected product ions of 443, 358, 332, and 84. Therefore, fragmentation of candidate adducted peptides should yield sufficient information both to identify its peptide sequence and to confirm that it is indeed IsoK lactam-adducted peptide. The detection of IsoK-adducted peptides may be facilitated by the use of the SALSA algorithm fact. This algorithm allows the detection of adducted peptides of low abundance. When these adducted peptides were chromatographed on the C8 RP-HPLC system for MS/MS, the adducted peptides were found to elute with retention times very similar to that of IsoK-lysyl-lactam, owing to the presence of the long IsoK hydrophobic side chains. In contrast, unadducted peptide eluted close to the void volume (data not shown). This chromatographic property of adducted peptides can be exploited to separate IsoK-adducted peptides from non-adducted peptides in protein trypsin digests. This, therefore, should greatly reduce the complexity of the mixture of peptides being analyzed for IsoK adducts.

Figure 36:
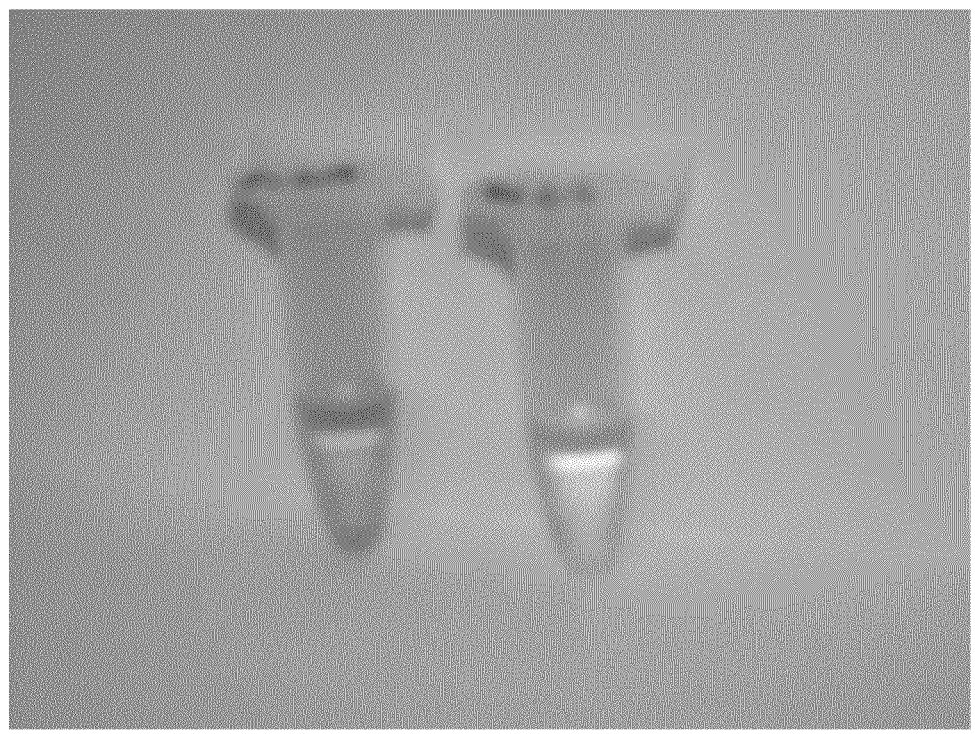
FIG. 36 is a color photograph showing precipitated HRP.

To determine whether D11 ScFv could be used for immunoprecipitation studies, the present inventors immobilized D11 ScFv to anti-E conjugated on Pharmacia NHS-sepharose 4 Fast Flow beads. As a target for immunoprecipitation horseradish peroxidase (HRP) with 5 molar equivalents of synthetic $E_2$-IsoK (IsoK-HRP) is adducted. After blocking the beads, equivalent amounts of HRP and IsoK-HRP with the D11 ScFv sepharose beads and blocking buffer for 1 hour is incubated. The beads are then centrifuged, supernatant removed, and washed six times. To visualize precipitated HRP, peroxidase substrate (ABTS) is added and allowed the green color to develop. The resulting color change is photographed (FIG. 36). The pelleted beads in the incubation that contained IsoK-HRP were intensely green, indicating that D11 ScFv Sepharose beads immunoprecipitated adducted HRP. In contrast, the pelleted beads that contained non-adducted HRP lacked color, indicating that D11 ScFv Sepharose beads did not precipitate non-adducted protein. These results indicate that the present inventors are able to effectively immunoprecipitate IsoK-adducted proteins from tissues using D11 ScFv Sepharose beads.

Dosage unit forms of the pharmaceutical compositions of the present invention comprise, for example, between 25 mg and 1000 mg of pyridoxamine or salicylamine, or a pharmaceutically acceptable salt thereof. Such dosage unit forms can comprise, for example, 25, 50, 75, 100, 125, 150, 175, 200, 250, 300, 350, 400, 450, 500, 550, 600, 650, 700, 750, 800, 850, 900, 950, or 1000 mg of pyridoxamine or salicylamine, or a pharmaceutically acceptable salt thereof, or any range of such dosage unit forms. In a preferred embodiment, the dosage unit forms of the pharmaceutical compositions comprise between 50 mg and 500 mg of pyridoxamine or salicylamine, or a pharmaceutically acceptable salt thereof. Such dosage unit forms can comprise, for example, 50, 75, 100, 125, 150, 175, 200, 250, 300, 350, 400, 450, or 500 mg of pyridoxamine or salicylamine, or a pharmaceutically acceptable salt thereof. The dosage unit form can be selected to accommodate the desired frequency of administration used to achieve a specified daily dosage of pyridoxamine or salicylamine, or a pharmaceutically acceptable salt thereof, to a patient in need thereof. Preferably the unit dosage form is prepared for once daily or twice daily administration to achieve a daily dosage of between 50 and 2000 mg, more preferably between 100 and 1000 milligrams.

Research Design and Methods: As stated above, one aspect of the present invention is to assess the formation of IsoK and NeuroK adducts quantitatively and qualitatively in AD.

Part of this aspect is determining whether levels of IsoK/NeuroK protein adducts are increased in CSF from patients with probable AD compared to age-matched controls. Levels of NeuroK adducts are increased, as measured by LC/MS/MS, and that IsoK adducts detected by IHC are clearly increased and localize to neurons and neuropil in the brains of patients who died of AD. The present inventors have determined that IsoK and NeuroK adducts are increased late in the disease, but whether they are present early on in the course of the disease cannot be determined using post-mortem brain specimens. However, analysis of CSF from living patients may provide an opportunity to do that. This allows correlation of levels of IsoK and NeuroK adducts with clinically scored disease severity. First, the present inventors determine whether we can detect IsoK and/or NeuroK adducts by LC/MS/MS in postmortem ventricular CSF from patients who died from AD. This may be done first because we can obtain up to approximately 30 mls of postmortem ventricular CSF whereas only approximately 1 ml of CSF is available from living patients with AD. Ventricular and lumbar CSF samples are provided.

Analysis and quantification of IsoK and NeuroK lysyl protein adducts by LC/ESI/MS/MS may be performed by existing methodology. Briefly, proteins are precipitated with ethanol containing butylated hydroxytoluene and triphenylphosphine to prevent autooxidation. Proteins are then enzymatically digested to free amino acids by sequential treatment with pronase and aminopeptidase. Lysyl adducts are then purified by RP-HPLC and then quantified by LC/MS/MS analysis using [$^{13}C_6$] labelled lysine adducts as an internal standard. This approach allows a determination of the level of protein adducts. However, it is conceivable that CSF may also contain IsoK/NeuroK adducted peptides, which will not precipitate with ethanol. Therefore, one may analyze also for adducts in CSF eliminating the protein precipitation step. The proteolytic enzymes therefore may be added directly to CSF. There may be endogenous inhibitors of proteolytic enzymes present in CSF in which case this approach would not be successful. This may be initially determined this by comparing the amount of lysyl IsoK adducts measured by LC/MS/MS from 1 mg of IsoK adducted OVA (ratio 5:1 IsoK:OVA) digested in PBS with adducted OVA digested in CSF. If protease inhibitors are present, first precipitate CSF with ethanol (to denature and inactivate any protease inhibitors) and analyzed for protein adducts. The supernatant may then be diluted in PBS and subjected to digestion and then analyzed for lysyl lactam adducts present on peptides.

Another embodiment of the present invention is an antibody that may be used against NeuroK adducts.

Figure 51:
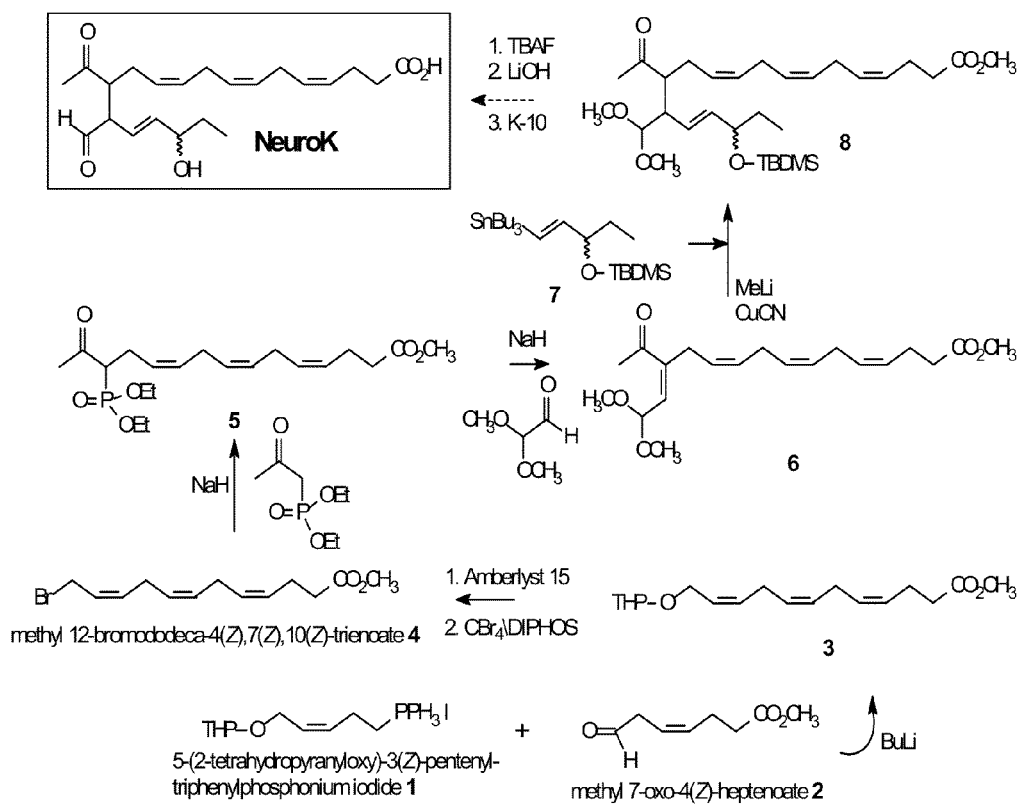
FIG. 51 is a method of the invention to synthesize a NeuroK isomer adapted from a method of the present invention to synthesize IsoKs.

Shown in FIG. 51, is a method of the present invention to synthesize a NeuroK isomer adapted from a method of the present invention to synthesize IsoKs. The long arm of the NeuroK, methyl 12-bromododeca-4(Z)-7(Z)-10(Z)-trienoate 4 is assembled by Wittig reaction between 5-(2-tetrahydropyranyloxy)-3(Z)-pentenyltriphenyl-phosphonium iodide 1, and methyl-7-oxo-4(Z)-heptenoate 2 followed by removal of the tetrahydropyranyl protection and conversion of the hydroxy to a bromo group. The preparation of 1 and a partial synthesis of 2 have already been completed. The rest of the synthesis will parallel the synthesis of IsoKs.

After synthesis of this NeuroK, an example of an approach to obtaining anti-NeuroK antibodies may follow those used to obtain D11 ScFv against lysyl IsoK adducts, discussed above. Developing these antibodies provides purified biotinylated NeuroK-adducted peptides for use in screening. Positive candidate clones may be screened against HNE, ONA, and IsoK adducted peptides and non-adducted proteins to determine the specificity of these antibodies. Candidate antibodies that recognize only NeuroK adducts are further evaluated for their use in Western blot, immunohistochemistry (IHC), and immunoprecipitation assays, as is disclosed above with respect to D11 ScFv.

Another aspect of the present invention is the determination of the localization of IsoK and NeuroK Adducts in brain in AD and other age-related dementias. Neuronal degeneration also occurs in other areas of the temporal and parietal lobes, in particular the amygdala, locus caeruleus, and nucleus basalis of Maynert. These regions are examined and for comparison, other regions unaffected by the disease. For this analysis, IHC with the D11 ScFv is performed. Brain slices obtained from the various regions of brain are examined. There should be neuronal staining in all affected regions of the brain, and less or no staining in unaffected regions. An anti-NeuroK adduct antibody of the present invention can be used in these same analyses for NeuroK adducts. As previously shown, levels of $F_4$-NeuroPs are consistently increased in AD brain to a much greater extent than levels of $F_2$-IsoPs, which is likely attributed to the fact that DHA is more easily oxidized than AA. Therefore, AD brain should exhibit even greater immunoreactivity for NeuroK adducts compared to that for IsoK adducts.

To compare the distribution of IsoK and NeuroK adducts in various age-related dementias, and with unrelated neurodegenerative diseases, post-mortem sections from the hippocampus, entorhinal cortex, temporal cortex, and frontal cortex of patients with DLB, VaD, MSA, ALS, and PD are analyzed by IHC for IsoK and NeuroK adducts as above. Samples are coded and analyzed.

Another aspect of the present invention is the determination of the role of oxidative injury in ApoE4 transgenic mice fed either a normal diet or a folate deficient/homocysteine enriched diet. As stated above, one aspect of the present invention is to determine the extent and localization of IsoK/NeuroK adduct formation in AD brain. However, these studies in humans do not easily allow determination of the time course of adduct formation in relationship to proteasome activity, behavioral abnormalities, and neurodegeneration during disease progression. Such studies can be best performed using transgenic mouse models. For this aspect, a mouse model may be used that combines established risk factors for dementia and AD, namely aging, presence of the ε4 allele of ApoE, overproduction of $A\beta_{1-42}$, and folate deficiency/hyperhomocysteinemia. These risk factors interact synergistically to increase levels of $F_2$-IsoPs, $F_4$-NeuroPs, and IsoK/NeuroK protein adducts. Although the ApoE4 Tg mice exhibit severe memory deficits, they do not show gross neuronal degeneration when fed a normal diet. Therefore, the effect of feeding these animals a folate deficient homocysteine enriched diet is studied to determine if this diet worsens cognitive defects and leads to neuronal degeneration.

All mice are fed standard chow diet until they reach 7 months of age. The diet is then changed to a defined amino acid diet supplemented with folate (normal) or the defined amino acid diet supplemented with 4.5 mg/kg D,L-homocysteine without added folate (homocysteine). These diets can be purchased from Dyets, Inc. The table below summarizes the study design and number of animals studied. At each of the time points listed, animals undergo behavioral testing and also are be sacrificed for measurements of IsoK/NeuroK adducts, $F_2$-IsoPs, and $F_4$-NeuroPs. Biochemical measurements on animals in each group are performed. The times that mice are studied and sacrificed for biochemical determinations are chosen based the relationship between age and the occurrence of elevated levels of $F_2$-IsoPs and memory deficit.

| Mouse Genotype | Diet | # Mice Sacrificed 7 month old | 9 month | 10 month | 11 month | 13 month |
|---|---|---|---|---|---|---|
| Wild Type | Normal | 20 | 20 | 20 | 20 | 20 |
| Wild Type | Homocysteine |  | 20 | 20 | 20 | 20 |
| ApoE4 | Normal | 20 | 20 | 20 | 20 | 20 |
| ApoE4 | Homocysteine |  | 20 | 20 | 20 | 20 |

Mice are euthanized using carbon dioxide. For each set of mice, the brain is removed immediately, the hemispheres divided, and for four mice one of the hemispheres will be placed in formalin solution, while the remaining hemisphere is placed in liquid nitrogen. All of the remaining mice in the set have both hemispheres placed in liquid nitrogen and stored at −70° C. until analysis.

Behavioral studies are conducted between groups (cross-sectionally) at different ages. Mice may be run individually on a commercially-available 8-arm radial maze (MED Associates, Georgia, Vt.) to assess short-term working memory. The maze is fully automated so that opening and closing of doors and food reinforcer delivery are controlled by a Windows-based computer running MED-PC software. Mice are introduced gradually to a food-restriction regimen that allows 2 hours free access to food per day, immediately following the daily session on the radial maze. Mice are not allowed to fall below 80% of their free-feeding weights. Typically on this restriction regimen mice lose weight initially, reach their free-feeding weights within a month, and then gradually gain weight over time. A habituation procedure similar to that described by Hartman et al. will be used, in which mice are required to retrieve one 20-mg food pellet from each of the eight arms before acquisition will begin. During acquisition training, one food pellet will be available at the end of each arm of the maze. Mice are required to retrieve the pellet from each arm during each daily session, which will end with the retrieval of the eighth pellet or after 5 min., whichever comes first. Working memory errors are classified as re-visits to arms from which the reinforcer had already been retrieved. A criterion of one or zero errors per session for three consecutive sessions will be used to determine successful acquisition of maze-running behavior. Errors per session and sessions to criterion will be the primary dependent measures of interest. The Y-maze spontaneous alternation task is a test of spatial memory that is sensitive to other manipulations that are known to impair memory, such as blockade of NMDA or M1 muscarinic receptors, hippocampal lesions, or elevated Aβ levels. Mice are placed individually in the maze, and exploratory behavior will be recorded for five min. The number and pattern of arm choices are the dependent variables of interest. The radial maze and spontaneous alternation task are both choice tasks, in which sensorimotor requirements for correct and incorrect responses are identical. Thus non-mnemonic phenotypes in the APOE4 transgenics, which may influence performance of tasks in which memory is inferred from speed of swimming or running, will not affect interpretation of performance of a task on which the mouse is required to choose between two or more alternatives. Nevertheless, it is important to document changes in non-mnemonic procedural variables. Thus, locomotor activity, balance/coordination, sensorimotor gating, and anxiety are accessed at each of the ages tested. Locomotor activity is tested in automated activity monitors (MED Associates, Georgia, Vt.). Balance and coordination are assessed using the wire hang and rotorod tests, and sensorimotor gating will be assessed using the prepulse inhibition of acoustic startle task. Anxiety is tested using the light/dark and elevated plus maze tests. All of these tests are well established in the Murine Neurobehavioral Laboratory (MNL) core facility.

For statistical analyses using standard values for α (0.05) and 1-β (0.75), the present inventors determined by power analysis that 15 mice per group are required to detect an effect of 0.40. For spontaneous alternation, percent alternation is calculated by dividing the number of alternations by the number of arm choices minus one. A factorial analysis of variance (ANOVA) is conducted on alternations as well as on number of arm choices, a measure of activity. A 2-factor repeated-measures ANOVA (RMANOVA) is used to analyze errors on the radial maze over repeated sessions. A factorial ANOVA is used to determine group differences in sessions to criterion, once all of the control mice have reached the criterion.

Data suggests that 8 mice hemibrains are sufficient to detect a 30% difference in levels lipid peroxidation products. Therefore, in aspects of the present invention, 8 mice are randomly chosen, and 1 frozen hemibrain from these 8 mice is weighed, placed in 2.5 ml Folch solution containing butylated hydroxytoluene (BHT) and triphenylphosphine (TPP) and homgenized. The homogenate then has saline solution added to initiate separation of esterified IsoPs and NeuroPs (lower phase). The lower phase is analyzed for esterified $F_2$-IsoPs and $F_4$-NeuroPs by GC/MS as described previously. The protein pellet at the interface of the Folch extraction is removed, further washed with EtOH and MeOH, and resuspended in PBS and subjected to complete enzymatic digestion using pronase and aminopeptidase. [$^{13}C_6$]-lysyl-IsoK/NeuroK-lactam internal standards are added and then analyzed for IsoK/NeuroK lactam adducts by LC/MS/MS as described previously.

Formalin fixed hemibrain is embedded in paraffin and prepared for immunohistochemistry. D11 ScFv to analyze IsoK adducts and the single chain antibody against NeuroK adducts may be used.

Assay of proteasome activity is performed as described previously. In one aspect, eight mice are randomly chosen and 1 frozen hemibrain from each mouse will by homogenized in 5 ml of buffer containing ATP and DTT and a 1 ml aliquot removed. The homogenate is then be centrifuged to remove cellular debris and proteasome activity is measured in the supernatant by hydrolysis of three fluorogenic substrates, z-LLVY-amc, boc-LRR-amc, and z-LLE-NA (Affiniti Research Products), which measure the chymotrypsin-like, trypsin-like, and peptidyl-glutamyl-hydrolyzing activities of the proteasome, respectively. Calpain can also hydrolyze LLVY-amc, therefore, a portion of each supernatant is treated with lactacystin or a calpastatin-derived peptide (American Peptide Company), which are selective proteasome and calpain inhibitors, respectively. Proteasome and calpain activities are calculated as difference between total LLVY-amc hydrolysis with and without their inhibitor. All activity will be normalized to amount of protein in the supernatant.

IDE activity is measured from homogenates as previously described by Qiu et al. Briefly, $^{125}$I-amyloid beta (Amersham Pharmacia) is added to homogenate and after appropriate time precipitated with TCA and run on SDS-PAGE. Changes in the 4 kD band are measured by densitometry.

Levels of Aβ peptides are measured by sandwich ELISA is described herein.

To quantify neurodegeneration, levels of synaptophysin in hemibrain homogenate by ELISA may be initially measured using a commercially available antibody (Accurate). If levels are significantly decreased in animals fed the folate deficient/homocysteine enriched diet compared to animals fed a normal diet, the total number of neurons in the hippocampus are estimated using stereological techniques.

As stated above, an aspect of the present invention is methods of determining whether pharmacologic interventions suppress IsoK/NeuroK adduct levels and improve cognitive defects in ApoE4 tg mice.

With respect to this embodiment, a supplementation with the antioxidants, Tempol and lipoic acid, improve cognitive deficits that develop in ApoE4 Tg mice.

As an example of this embodiment, animals are fed a standard chow diet until they are 7 months old, after which they are either continued on a normal diet or switched to the folate deficient/homocysteine enriched diet. Animals are given either one of the 2 antioxidants: Tempol (1 mM in drinking water) and lipoic acid (1 g/L in drinking water). The doses these antioxidants acid chosen to test is based on the data presented under Preliminary Studies. Other antioxidants may be used.

In this embodiment, twenty animals are included in each treatment group as outlined in the table below. The duration of the study is 13 months. After thirteen months, mice undergo behavioral testing and sacrificed for analysis of $F_2$-IsoPs, $F_4$-NeuroPs, IsoK and NeuroK adducts, protease activity, and neurodegeneration. Measurement of products of the IsoP and NeuroP pathways allows a determination of the ability of the different antioxidants to suppress oxidative injury in these animals. Doses and/or routes of administration, e.g. daily i.p. injections, may vary. This aspect of the invention suggests oxidative injury plays playing a pivotal role in causing the neurodegeneration.

In one embodiment, pyridoxamine is administered in the same dose that has been found effective in preventing and retinopathy and early renal disease in diabetic rats, 1 g/L of drinking water. The same parameters are evaluated as described above for the antioxidant studies. The outline of both studies is shown in the table below. The results from treating animals with antioxidants allows a determination of the role of oxidant injury in general in these processes and treatment with pyridoxamine will allow a determination of the specific role of reactive products of lipid peroxidation.

| Mouse Genotype | Diet | Tempol | Lipoic Acid | Pyridoxamine |
|---|---|---|---|---|
| ApoE4 | Normal | 20 | 20 | 20 |
| ApoE4 | Homocysteine | 20 | 20 | 20 |

The ability of PM to scavenge γ-ketoaldehydes suggests that it may be possible to generate compounds that will trap IsoKs/NeuroKs even more effectively. Therefore the present invention includes various modifications of the functional groups of PM. In one embodiment, phenyl ring substituents that participate in hydrogen bonding are factors in the scavenging ability of PM. Additionally, PM to a more hydrophobic molecule enhances its ability to intercept IsoKs/NeuroKs in certain environments, including lipid environments.

Aspects of the present invention including the following PM analogs, which are presented purely for exemplary purposes, and should not be construed as limiting of the present invention:

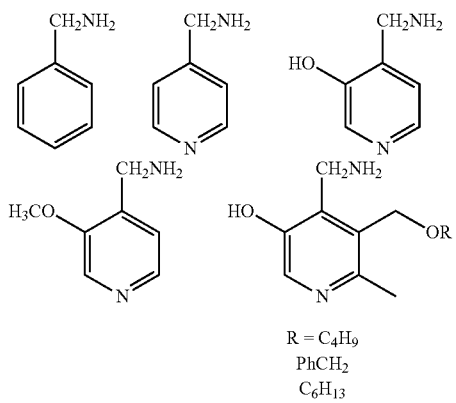

R = C₄H₉
PhCH₂
C₆H₁₃

These compounds are tested for the rate of pyrrole formation when incubated with the γ-ketoaldehyde, 4-oxopentanal. This γ-ketoaldehyde does not undergo the rapid oxidation that occurs with IsoK/NeuroK pyrroles to form lactams because it is not highly alkylated, making it more straightforward to measure rates of pyrrole formation. Ehrlich reagent may be used to detect levels of pyrroles. We will incubate radiolabeled IsoK with may be radiolabeled OVA to determine the ability of equimolar levels of various PM analogs to prevent radiolabelling of protein. The amount of IsoK adduction to protein may be determined by the amount of radiolabel present in TCA precipitates of the adducted protein in the presence of the various PM analogs. If a PM analog has highly superior IsoK/NeuroK scavenging ability compared to PM, aspects of the present invention include examining the toxicity and effectiveness of these analogs in the ApoE4 Tg mice.

Another aspect of the present invention is a method of identifying proteins adducted by IsoKs and NeuroKs in hippocampus of brains from patients with AD and in ApoE Tg mice fed either a normal or folate deficient/homocysteine enriched diet.

As an example, two approaches may be used to identify proteins adducted by IsoKs and NeuroKs in AD. The first is a candidate protein approach, which will examine specific proteins with putative roles in AD. The second simply seeks to identify the most abundant adducted proteins. A strength of the first approach is that it can be done rapidly and with high probability of success. Furthermore, significant increases in adduct levels are found, the effect of adduction on the known activities of that particular protein can be characterized. The disadvantage of this approach is that it may exclude important novel proteins previously not known to be affected by AD pathology. A strength of our second approach is that it makes no such assumption and may therefore identify important novel proteins that may be important in AD pathology. The disadvantage of this approach is that many adducted proteins may be present in low abundance, making identification problematic, and the simple presence of adducts does not necessarily mean adduction of that protein is important in the pathogenesis of AD.

As part of this aspect, one can determine whether there is enhanced adduction of the following proteins by IsoKs and NeuroKs: tau, tubulin, proteasome subunits, insulin degrading enzyme, ApoE, choline acetyltransferase, and neuronal growth factor receptors.

One strategy for the quantification of adducts of these proteins is to use a sandwich ELISA, as described above with respect to tau. Antibodies may include: tau (Zymed), 20S proteasome alpha and beta subunits (Affiniti Research Products), 19S regulator ATPase subunits rpt 1-6 (Affiniti), 19S regulator Non-ATPase subunits (Affiniti), ApoE (Biodesign Intenational), choline acetyltranferase (Abcam), p75NGFR (Abcam), trkA (Advanced Targeting Systems), and tubulin (Chemicon International). Proteins may include: tau protein (Sigma), proteasome subunits (Affinit), ApoE (Panvera, Madison, Wis.), and tubulin (Cytoskeleton). Target proteins are adducted using synthetic IsoK or NeuroK and the conditions for the sandwich ELISA optimized. Antibodies to the target protein are coated onto the 384-well plate, the plate blocked, and the adducted protein added. After washing, the D11/AntiE-HRP is added and then after further washing detected with peroxidase substrate. To ensure that the sandwich ELISA conditions will detect small differences in adducted protein levels, a known amount of adducted protein may be spiked into some control brain samples. For target proteins that purified proteins are not yet commercially available, the ELISA can be initially performed on tissue samples without optimization, using the manufacturer's recommended dilutions to coat the plates. If necessary, synthetic peptides representing the immunogen for the appropriate antibody may be used for optimization of adducted immunogen binding. Adduct levels in these proteins are compared and analyzed from a minimum of 6 brains each from patients with AD and age-matched controls, 6 brains from wild type mice fed a normal diet and 6 brains from ApoE4 Tg mice fed a folate deficient/homocysteine enriched diet for 13 months.

Proteins that are identified in the screening using ELISA that contain increased adducts may be further analyzed by LC/MS/MS. The protein may be immunoprecipitated using the appropriate antibody. A portion of the precipitate is digested with pronase and aminopeptidase and analyzed for IsoK or NeuroK lysyl lactam adducts by LC/MS/MS. Presence of lysyl IsoK and/or Neurok lactam adducts in the precipitate is partial confirmation. However, a more definitive confirmation may include identification of adducted peptides from a tryptic digest of isolated proteins. To establish a potential profile of the adducted protein, take purified protein and adduct it with synthetic IsoK or NeuroK. The protein is then be subjected to digestion with trypsin and the fragments separated by HPLC. The fragments are then be analyzed by MS using the new highly sensitive LCQ instrument in the Vanderbilt Mass Spectrometry Core. The instrument is be set to MS/MS mode. In this mode, the instrument picks the five most abundant ions in each scan for fragmentation and analysis of product ions. The various scans are then analyzed using a SALSA algorithm program that scores each scan based on the primary and secondary characteristics of adducted peptides that we have established using the IsoK-adducted peptides in our preliminary studies. These are product ions including m/z 443, 358, 332, and 84 that are specific for the IsoK lactam adduct. It also looks for expected mass shifts that would result from the presence of the adduct on lysine. This program identifies which of the thousands of scans are most likely to be from adducted peptides. Then the scan can be manually examined to determine if it indeed matches an expected adducted peptide from the target protein. Trypsin fragments from unadducted proteins may be analyzed to ensure that putative adducted peptide scans are unique to adducted protein.

The information gained from this analysis may be used to analyze tryptic digests of immunoprecipitates from AD brain. One may look initially for the exact precursor ions that we found with purified proteins. However, it is understood that that the adduction in vitro may not fully mimic adduction that occurs in vivo because different lysine residues may be adducted. Therefore, one may also analyze trypsinized peptides by LC/MS/MS using the SALSA software to analyze LCQ scans as before. Also, the high scoring scans may be manually examined to determine if they matched expected peptide sequences from the target protein. If these scans match predicted adduct sequence, the peptides may be synthesized. Then, the peptide may be adducted with [$^{13}C_3$] IsoK, for use as an internal standard. Then, the levels in 6 AD brains and 6 aged-matched controls may be quantified and compared. Increased levels of these adducted peptides would be complete confirmation of increased adducted target protein in AD brain. Since the site of protein modification is known, this information allows prediction of the potential consequences of this adduct formation and would be the basis for studies to determine the effect of adduction on protein function.

These experiments are performed by immunoprecipitation of brain homogenates with D11 ScFv and the anti-NeuroK lysl adduct ScFv. Precipitates are placed on matrix assisted laser desorption ionization (MALDI) targets, matrix added, and then MALDI time of flight (TOF) MS performed. If a large number of peaks appear in both precipitates from AD brain (or brain from the animal model of AD), the precipitate may be fractionated using ion exchange chromatography prior to MALDI-TOF analysis. Peaks unique to disease brain are selected for further analysis using post-source decay. If there are relatively few peaks present, the precipitate fractions are run on SDS-PAGE gels and stained with Commassie blue. Individual bands are then excised from the gel, digested, and sequenced by MALDI-TOF. If the sequence corresponds to a known protein, the presence of the protein is confirmed.

After identification of proteins in the previous subaims that might participate in decline of cognitive function, the age when these proteins become adducted relative to the development of memory deficits is determined. In this way, insight is gained into whether alterations in these proteins might be causally linked to the development of memory impairment. The levels of these adducted proteins are measured in the same way as for AD brain, except that as necessary, the masses of the adducted peptides examined by MS are adjusted to match the mouse sequences.

Cardiovascular Diseases: As stated above, another aspect of the present invention relates to treating and preventing cardiac diseases. This aspect includes, but is not limited to, treating and preventing ventricular fibrillation and/or arrhythmias as well as preventing or retarding the progression of oxidative stress associated with vascular dementia or stroke. The methods of this embodiment may include the use of the above-described compounds and pharmaceutical formulations.

Sudden cardiac death due to ventricular fibrillation (VF) remains a major public health problem, with costly implanted defibrillators as the major advance in therapy in the last decade. On the other hand, conventional antagonist "antiarrhythmic" drugs selectively targeting the molecular species driving cardiac excitability, the ion channel, have not yielded convincing benefits in survival, and in many cases elicit a paradoxical increase in arrhythmia risk. While the seminal mechanistic features of ischemic VF remain obscure, growing evidence implicates an interaction between cardiac $Na^l$ channels and the recently injured or acutely ischemic myocardium. In 1989, the Cardiac Arrhythmia Suppression Trial (CAST) found that therapy with the potent $Na^-$ channel-blocking drugs (flecainide or encainide) in patients convalescing from myocardial infarction unexpectedly increased mortality three-fold. A further analysis of the CAST database indicated that patients whose index myocardial infarction was not transmural ("non-Q wave"), a subset known to be at higher risk for recurrent myocardial ischemia, exhibited an even greater (8.9-fold) risk with concomitant $Na^+$ channel blocker therapy.

More recently, the Brugada Syndrome, a rare autosomal dominant disorder of idiopathic ventricular fibrillation, has been attributed to alterations in $Na^+$ channel function arising from mutations in the gene encoding the human cardiac Na channel (hH1, or SCN5A). Functional analysis of recombinant $Na^-$ channels that carry these mutations often reveal familiar changes in gating function that resemble the effects of $Na^+$ channel blocking agents: enhanced sodium channel behavior. The phenotypic similarity between the genetic and pharmacologic arrhythmia models cast suspicion on enhanced $Na^+$ channel inactivation as a general proarrhythmic mechanism. A molecular mechanism whereby cardiac ischemia could alter $Na^+$ channel function in this proarrhythmic manner has not been identified.

Acute hypoxia depletes the myocardial cells of intracellular defenses against reactive oxygen species, such as superoxide dismutase and glutathione. Unabated, reactive oxygen species are free to react with key cellular components, and can attack unsaturated fatty acids and form lipid peroxides that are known to affect membrane proteins. This process is potentiated by an ischemia-induced shift in anaerobic metabolism, forming xanthine oxidase, which generates superoxide anion upon reperfusion and reintroduction of oxygen. The products of free radical-induced lipid peroxidation can covalently adduct and modify membrane proteins. Recently E2-isoketals (IsoKs) were identified as an extraordinarily reactive lipid peroxidation product. IsoK's are generated via the isoprostane lipid peroxidation pathway, a non-enzymatic free radical-induced peroxidation of arachidonic acid. IsoKs rapidly adduct to amines and especially to the lysine residues on proteins.

The present inventors have discovered a link consistent changes in $Na^-$ channel inactivation gating function, similar to those associated with Brugada syndrome, to the byproducts of a particular oxidative pathway. In addition, the present inventors show synergy between the pharmacological effects of flecainide, a proarrhythmic $Na^+$ channel blocker, and oxidative stress. Also, the present inventors find that these reactive byproducts accumulate in cultured (HEK) cells upon exposure to oxidative stress, as well as in the specific canine infarct zones where $Na^+$ channels have been shown to exhibit enhanced inactivation. Studies related to this invention suggest $Na^+$ channel dysfunction evoked by highly-reactive lipid peroxidation products is an important candidate mechanism for ischemia-induced ventricular fibrillation and sudden cardiac death, and may help explain the proarrhythmic effects of $Na^+$ channel blocking agents during myocardial ischemia.

Figure 37:
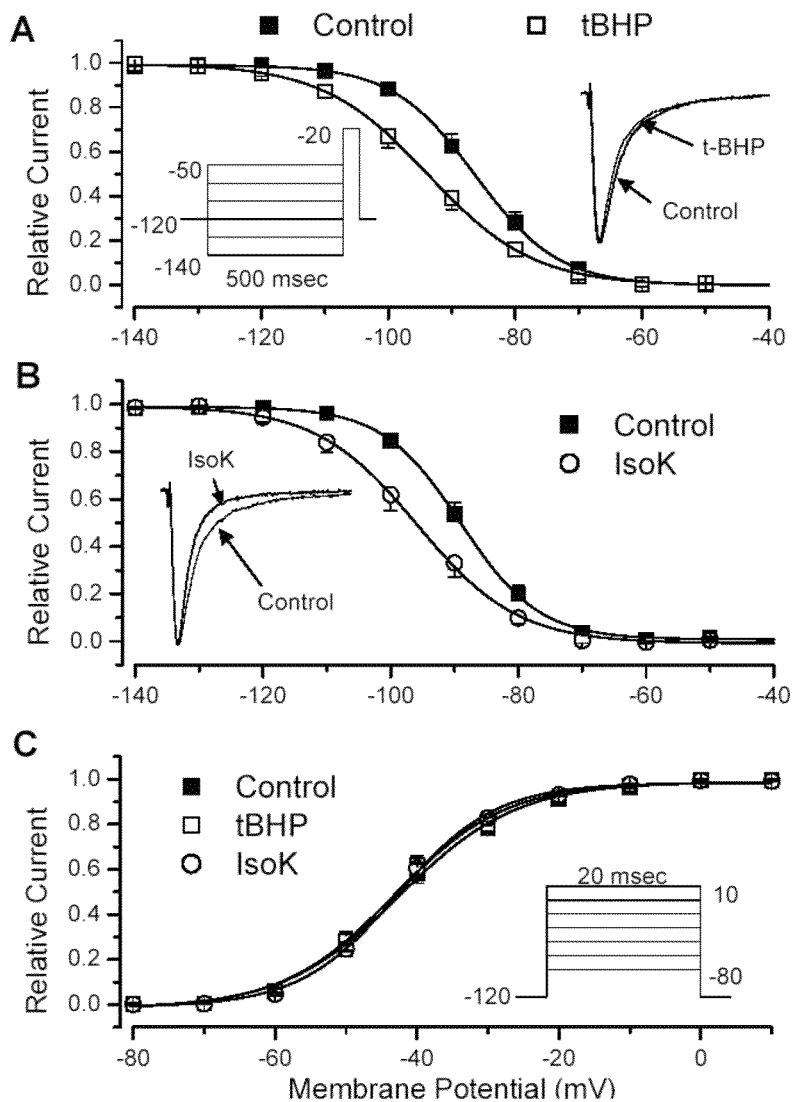
FIGS. 37-40 are graphs showing data in connection with the present invention.

FIG. 37 shows voltage-dependent properties of sodium channel. A. Voltage-dependence of inactivation of sodium channels transfected in HEK-293 cells in the presence of the general oxidant, t-BHP (1 mM). The voltage-clamp protocols are shown in the inset, and data were fitted to a Boltzmann function (y=[1+exp {(V−$V_{1/2}$)/k}]−1), where $V_{1/2}$ is the half-maximal voltage and k is the slope factor. Over a range of potentials t-BHP caused a negative shift in the voltage-dependence of inactivation. For control $V_{1/2}$=−86.7±1.6 mV. In the presence of t-BHP, $V_{1/2}$=−93.9±1.9 mV (P<0.01 with control). B. Voltage-dependence of Na+ channel inactivation in the presence of Iso-K (10 µM). Like t-BHP, Iso-K also caused a negative shift in the inactivation curve. For control, $V_{1/2}$=−89.0±1.3 mV. In IsoK, $V_{1/2}$=−96.4±1.1 mV (P<0.01 with control). C. Voltage-dependence of activation evaluated using the protocol shown in the inset. The oxidants, t-BHP and Iso-K had no effect on the activation of sodium channels over a range of membrane potentials.

Figure 38:
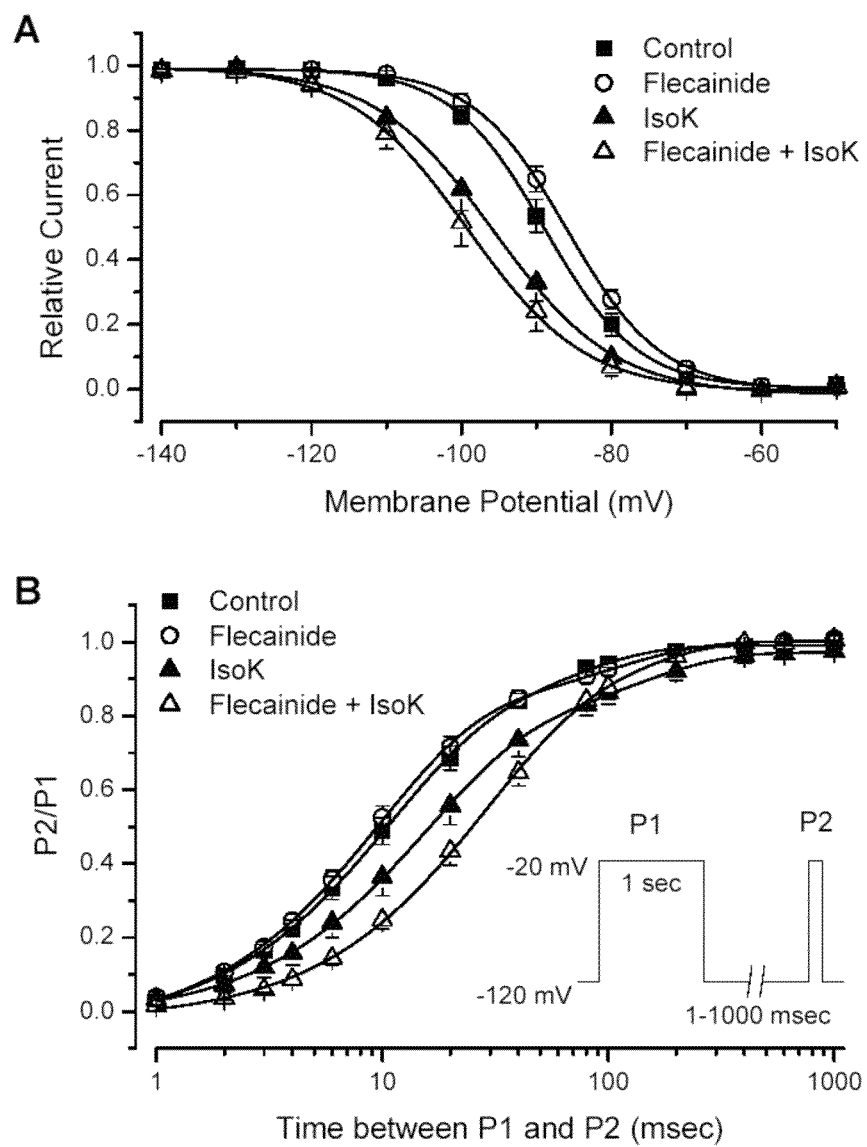

FIG. 38 shows the effect of Iso-K on voltage and time-dependent inactivation in the presence of flecainide. A. Voltage-dependence of inactivation in the presence of flecainide (1 µM) and/or Iso-K (10 µM) is obtained. While IsoK shifted the curve in the hyperpolarizing potential, flecainide had no additional effect on inactivation. For flecainide, $V_{1/2}$=−86.4±2.1 mV (P=NS with control) alone and −99.3±2.3 mV in the presence of IsoK (P=NS with Iso-K alone). B. Recovery from inactivation was evaluated using the protocol shown in the inset. The time course was characterized by two kinetic components, representing fast and slow inactivation and was therefore fitted by a two exponential function y=$y_0$+$A_1$(1−exp [−t/$\tau_{fast}$])+$A_2$(1−exp [−t/$\tau_{slow}$]). Iso=K delayed the recovery from inactivation and flecainide accentuated this effect. Data are summarized in the table below.

Figure 39:
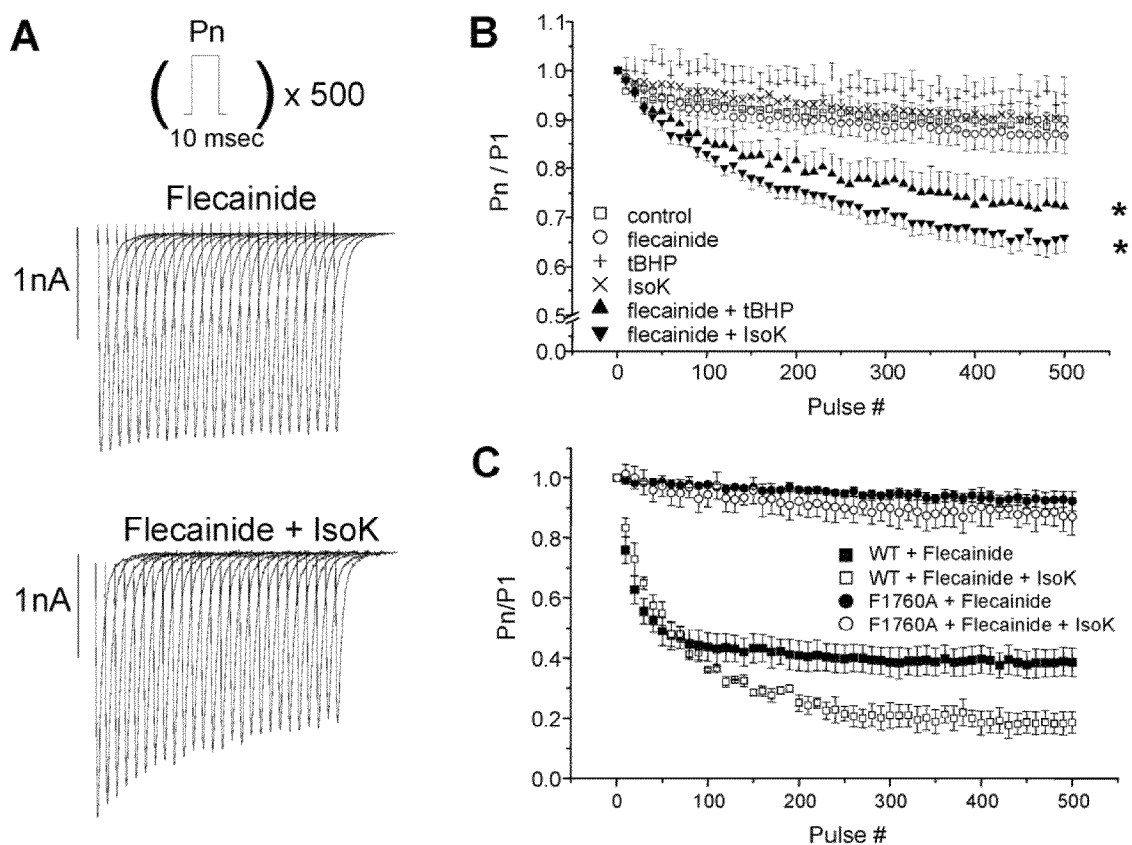

FIG. 39 shows effects of oxidative stress on use-dependent flecainide block. A. Use-dependent flecainide block was examined using the protocol shown. A train of 500 depolarizing pulses with 10 msec duration at −20 mV were applied at a frequency of 5 Hz. Currents are plotted from every twentieth pulse. Upper panel represents the current in the presence of flecainide (1 µM). Lower panel represents $I_{Na}$ in the presence of flecainide and IsoK (10 µM). B. Depolarization-dependent effects are summarized as a function of the pulse number. All current amplitudes are normalized to that of the first depolarization and every tenth pulse is plotted. Even after the five hundredth pulse, flecainide did not reduce the current (P500/P1=0.90±0.03 (control, n=6) vs. 0.87±0.04 (flecainide, n=5), n.s.). In contrast, IsoK and t-BHP significantly reduced the current in the presence of flecainide (0.66±0.03, P<0.001, 0.72±0.05 (n=6), P<0.05, respectively vs. flecainide), but not in the absence of flecainide (0.89±0.02 (n=10), n.s., 0.95±0.04 (n=6), n.s., respectively vs. control). C. When the putative flecainide binding site was mutated to alanine (F1760A), the enhancement of use-dependent flecainide block by Iso-K was prevented. For these experiments flecainide concentration was increased to 10 µM. Use-dependent block of flecainide was enhanced with IsoK (10 µM) in WT (P500/P1=0.38±0.05 in flecainide alone (n=4) vs. 0.19±0.04 in the combination of flecainide and IsoK (n=3), P<0.05). F1760A prevented the use-dependent block of flecainide (0.92±0.03 n=4, P<0.0001, vs. WT). IsoK did not enhance the use-dependent block of flecainide in F1760A (0.87±0.06 in the combination of flecainide and IsoK (n=4), n.s., vs. flecainide alone).

Figure 40:
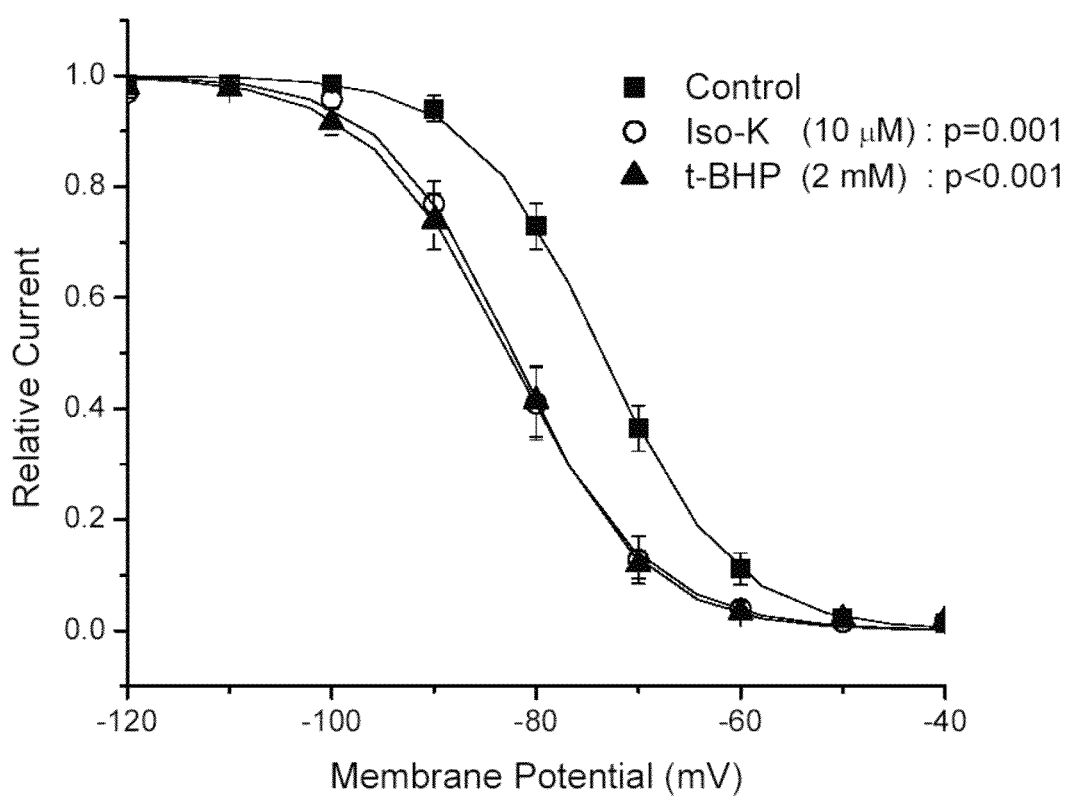

FIG. 40 shows the effect of oxidative stress in immortalized atrial myocytes. Voltage-dependence of inactivation is evaluated. Preincubation of t-BHP and IsoK reduced Na channel availability in HL-1 cells, an effect that was similar to those seen on sodium channels expressed in HEK-293 cells.

Figure 41:
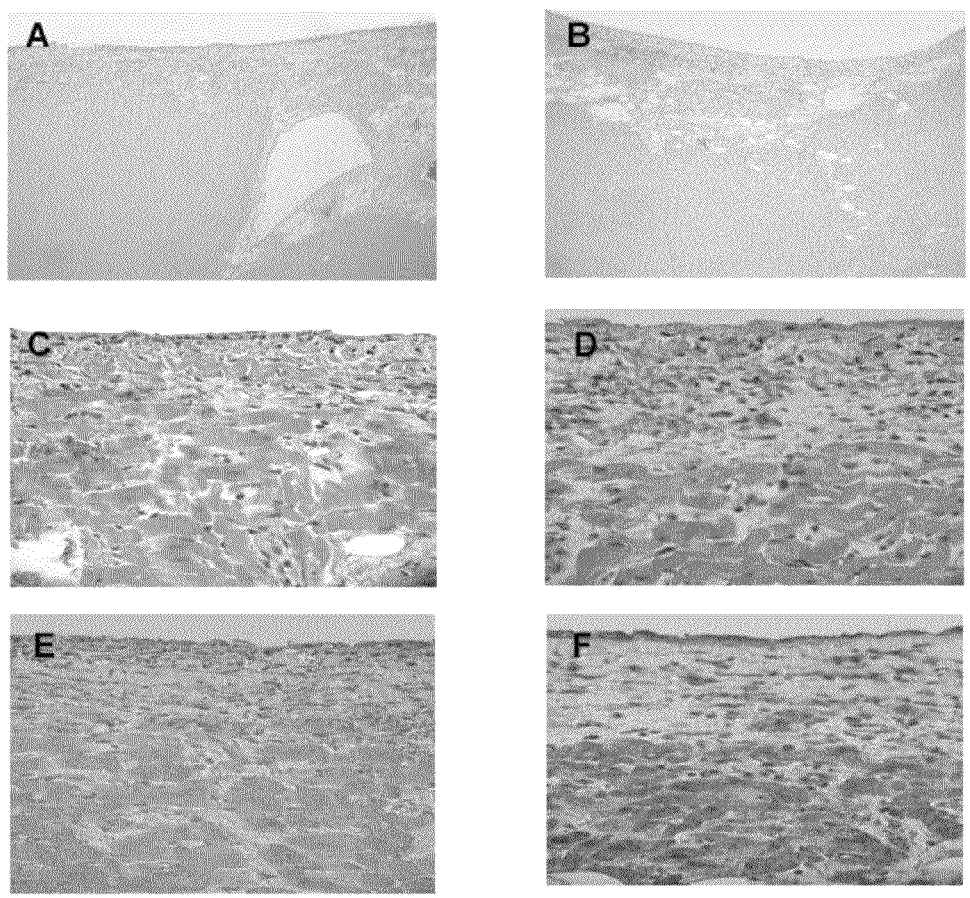
FIG. 41 is a series of color photographs showing $F_2$-IsoPs esterified in heart samples.

Finally, FIG. 41 shows D11 ScFv immunohistochemistry—adduct formation in the epicardial border zone of infarct. A, C, and E represent remote sections of heart taken far away from the area of the infarct. B, D, and F represent sections of heart taken from the border zone of the infarct. A and B are low power (5×) sections where the D11 ScFv primary antibody was not included in the protocol and demonstrate specificity of staining in other sections. C and D are high power (40×) sections stained with H&E and show that there are not fundamental morphological differences between the remote and border zones. E and F are sections stained with D11 ScFv primary antibody and anti-E tag HRP conjugated secondary antibody. Color was developed using AEC, and sections were counterstained with hematoxylin. Profound immunoreactivity to IsoK adducts is readily apparent in the EBZ, which is clearly not present in the remote sections.

As a non-limiting experimental example of this embodiment, recombinant wild-type and mutant $Na^+$ channels were prepared as previously described and were subcloned into the expression vector pCGI (provided by David Johns, Johns Hopkins University, Baltimore, Md.) for bicistronic expression of the channel protein and GFP reporter in HEK-293 cells. Where indicated, cells were co-transfected with an equimolar ratio of Na channel human $\beta_1$ subunit. cDNAs were transiently transfected into HEK-293 cells using lipofectamine (GIBCO-BRL, Gaithersburg, Md.), and were cultured in MEM medium supplemented with 10% fetal bovine serum and 1% pen-strep in a 5% CO2 incubator at 37° C. for 1 to 4 days. Cells exhibiting green fluorescence were chosen for electrophysiology analysis.

Electrophysiology: Whole-cell sodium currents were recorded at room temperature (Axopatch 200B, Axon Instruments, Foster City, Calif.) using electrodes of 1-2 MΩ when filled with a pipette solution containing (in mM): NaF 10, CsF 110, CsCl 20, EGTA 10, Hepes 10 (pH 7.35 with CsOH). The bath solution contained (in mM): NaCl 145, KCl 4.5, $CaCl_2$ 1.5, $MgCl_2$ 1, Hepes 10 (titrated to pH 7.35 with CsOH). For myocyte recordings, the bath solution contained (in mM): NaCl 20, Choline Chloride 115, KCl 4.5, CaCl2 1, CoCl2 2, MgCl2 1, BaCl2 1, hepes 10, and niflumic acid 10 µM. In all recordings, 75% of the series resistance was compensated, yielding a maximum voltage error of ~1 mV. The disulfide reducing agents dithiothreitol (DTT) and glutathione were dissolved directly in the extracellular and pipette solutions at a concentration of 2 mM. The oxidative agents tert-butyl hydroperoxide (t-BHP), hydrogen peroxide($H_2O_2$), and lipid peroxidation products (discussed below) were dissolved directly in the extracellular solution.

Whole-cell Na currents ($I_{Na}$) were sampled at ≥20 kHz through an A/D converter (DigiData 1200, Axon Instruments, Foster City, Calif.) and low pass filtered at 5 kHz unless otherwise specified. Data were collected and analyzed using pClamp 8.0 software (Axon Instruments). Inactivation gating kinetics were assessed using voltage-clamp protocols described in the text and figure legends. All results are expressed as mean±SEM unless otherwise specified and statistical comparisons were made using one-way ANOVA (Microcal Origin, Northampton, Mass.) with p<0.05 indicating significance. Multi-exponential functions were fitted to the data using non-linear least-squares methods (Origin).

Synthesis and analysis of reactive products of lipid peroxidation: $E_2$-isoketal was synthesized as previously described. The present inventors used mass spectrometry to analyze $F_2$-isoprostanes formed following treatment of HEK 293 cells with t-BHP. For this assay, HEK-293 cells (1×$10^6$) were treated for 30 minutes at room temperature with buffer containing 100 µM t-BHP, or 100 µM t-BHP and 200 µM $FeCl_2$. Total (free and esterified) $F_2$-isoprostanes ($F_2$-IsoPs) esterified in cellular lipids were then quantified by a highly accurate GC/NICI/MS assay as described previously.

Preparation of Myocardial Infarction: Under isoflurane anesthesia (30 mg/kg) and sterile conditions, myocardial infarction was produced by a two-step total occlusion of the left coronary artery using the Harris procedure. Dogs were treated with lidocaine (2 mg/kg IV) if multiple ventricular beats occurred at the time of the surgical procedure. Five days after surgery, a cardiectomy was performed with the dogs under sodium pentobarbital (30 mg/kg IV) anesthesia.

Slices of tissue were taken from the visible epicardial border zone (EBZ) area as previously described as well as am area remote (Rem) from the infarct (LV base). Some tissues were quickly frozen for analysis. Other tissues were subjected to our cell dispersion protocol to study using whole cell techniques, Na⁻ current function. In some hearts columns of tissue (from epicardium toward infarct core) are frozen for histochemical examination.

Oxidizing agents reduce cardiac $Na^+$ channel availability: In order to investigate the gating effects of oxidizing agents, the present inventors recorded $I_{Na}$ from HEK cells expressing wild-type hH1 in control conditions and after 30 mins of preincubation with a membrane-permeant form of hydrogen peroxide (t-butyl hydroperoxide, t-BHP). To assess the voltage-dependence of channel availability (FIG. 37A), data were fitted by a Boltzmann function ($y=[1+\exp\{V-V_{1/2}\}/k\}]^{-1}$), where $V_{1/2}$ is the half-maximal voltage and k is the slope factor. Over a range of holding potentials, channel availability was altered by preincubation with t-BHP: $V_{1/2}$ was hyperpolarized by nearly 7 mV, from −86.7±1.6 mV to −93.9±1.9 mV (P<0.01). There was no effect on $I_{Na}$ decay (inset, panel A). To examine whether the gating effects induced by t-BHP could result from generation of reactive products of lipid peroxidation, the present inventors exposed HEK cells expressing hH 1 channels to a number of lipid peroxidation products including E2-isoketal (IsoK), $F_2$-isoprostane ($F_2$-Isop) and 4-hydroxynonenal (HNE).

IsoK shifted the steady-state availability curve to hyperpolarized potentials, similar to t-BHP (FIG. 37B, $V_{1/2}$: from −89.0±1.3 mV to −96.4±1.1 mV; P<0.01). Unlike t-BHP, Iso-K speeded the rate Of $I_{Na}$ decay during a depolarizing pulse from −100 mV to −20 mV (inset, panel B). In contrast to Iso-K and t-BHP, $F_2$-Isop or HNE did not affect the voltage-dependent availability of $Na^+$ channels ($V_{1/2}$ was −87.9±1.8 mV and −91.4±1.8 mV, for control and $F_2$-IsoP, respectively, P=NS; $V_{1/2}$ was −86.7±1.6 mV and −83.7±2.1 mV, for control and HNE, respectively, P=NS). t-BHP and IsoK did not affect the voltage-dependence of $Na^+$ channel activation as seen in FIG. 37C ($V_{1/2}$ control: −43.1±1.3 mV, t-BHP: 42.4±1.5 mV and Iso-K: −41.6±1.5 mV). While previous studies observed a persistent inward current due to oxidation (similar to the effects of long QT 3 mutations), the present inventors did not observe any sustained non-inactivating component of $Na^+$ current during exposure to t-BHP or Iso-K. In summary, the gating effects of t-BHP and IsoK were similar, causing a hyperpolarizing effect on voltage-dependent availability, consistent with a selective stabilization of the "inactivated" conformational state. The effect appears specific for the isoketal lipid peroxidation pathway, as other common isoprostanes (HNE, $F_2$IsoP) had no effect.

Synergistic effects of $Na^+$ channel blockers and Iso-K: Given the evidence that free radicals and free radical-induced lipid peroxidation products have been identified during ischemia-reperfusion and that $Na^+$ channel block can be proarrhythmic post myocardial infarction, the present inventors tested the combined effects of flecainide and Iso-K on $Na^+$ channel function. The present inventors first examined the steady-state availability of $Na^+$ channels in the presence of flecainide and Iso-K alone. While Iso-K shifted the availability curve to more negative potentials (FIG. 38A, FIG. 37B), flecainide had no effect (FIG. 38A). Furthermore, in the presence of IsoK, flecainide had no additional effect (FIG. 38A, $V_{1/2}$: from −86.4±2.1 mV to −99.3±2.3 mV; P<0.0001).

Characterization of inherited hH1 mutations linked to the Brugada arrhythmia syndrome have clarified that in addition to altering the voltage-dependence of inactivation, mutations that delay the rate of recovery from inactivation during diastole reduce the availability of $Na^+$ channels to open at rapid rates, and may thus set the stage for reentrant circuits and ventricular fibrillation. To further characterize the interaction between IsoK and flecainide, a twin-pulse voltage-clamp protocol (FIG. 38B inset) was used to evaluate the rate of $Na^+$ channel recovery from inactivation: $I_{Na}$ recorded in the second (P2) pulse was measured relative to that recorded during the preceding P1 pulse as the interpulse interval was progressively increased from 1 ms to 1 sec. FIG. 38B plots the magnitude Of $I_{Na}$ in the P2 pulse relative to P1 pulse. To quantify this gating effect, the data were fitted by a two exponential function, $y=y_0+A_1(1-c^{-t/\tau fast})+A_2(1-c^{-t/\tau slow})$, where $\tau_{fast}$ and $\tau_{slow}$ represent rapid and slow kinetic components of recovery from inactivation. The fitted parameters are shown in Table 1. Flecainide alone had no effect as shown previously. IsoK delayed both kinetic components ($\tau_{fast}$; from 12.5±1.1 to 17.4±2.2, P<0.05: $\tau_{slow}$; from 48.7±3.2 to 155.1±32.9, P<0.001, respectively). In the presence of flecainide, IsoK still delayed both components ($\tau_{fast}$; from 10.3±2.2 to 29.7±1.8, P<0.0001: $\tau_{slow}$; from 64.3±3.8 to 119.4±10.1, P<0.0001, respectively), and the effect of IsoK on the fast component was greater in flecainide than IsoK alone (P<0.001). This suggests that flecainide "aggravates" the delay of recovery from inactivation caused by IsoK. Particularly at rapid heart rates, where diastolic intervals are brief, conditions that delay recovery of $Na^+$ channel inactivation cause a cumulative loss of $Na^-$ current, termed "use-dependence". Use-dependence can have proarrhythmic consequences. To examine if the effects observed in FIG. 38B are manifest as proarrhythmic alterations in use-dependence, depolarizing pulses were applied in the presence of t-BHP or IsoK at a frequency of 5 Hz. At this frequency, a therapeutic concentration of flecainide (1 μM) did not increase use-dependence (FIG. 39A and B). Similarly, IsoK (10 μM) alone did not change $I_{Na}$. However, IsoK caused a significant use-dependent loss Of $I_{Na}$ in the presence of flecainide (FIG. 39A, B). Similar results were seen with t-BHP (FIG. 39B), again illustrating concordance between the effects of a general oxidant (t-BHP) and IsoK.

To confirm that the observed IsoK-flecainide synergy is specific, and requires binding of flecainide to its receptor on the $Na^+$ channel, the present inventors studied a mutant $Na^+$ channel in which the putative local anesthetic binding site was mutated (F1760A). The effects of IsoK were tested using the same protocol as FIG. 39A. In this experiment, the concentration of flecainide was increased to 10 μM to exaggerate use-dependence. As previously reported, use-dependent flecainide block was significantly attenuated in F1760A channels compared to wild type. Moreover, the combination of IsoK and flecainide did not enhance block of F1760A channels (FIG. 39C). These data demonstrate that flecainide binding is required for use-dependent synergy between flecainide and IsoK.

Peroxides induce lipid peroxidation metabolites that modify $Na^+$ channel gating/Isoprostanes accumulate in the ischemic myocardium: To establish the relevance of these findings to the myocardium, the present inventors first examined the effects of t-BHP and Iso-K on Na$^+$ channel availability in immortalized mouse atrial myocytes (HL-1) cells. As in the recombinant system, t-BHP (2 mM) shifted the availability of native Na$^+$ channels (FIG. 40) to hyperpolarizing potentials ($V_{1/2}$: −73.6±1.4 mV in control, −82.8±1.7 mV in t-BHP, p<0.01). Similarly, exposure to Iso-K (10 μM) shifted the availability to hyperpolarizing potentials ($V_{1/2}$: −82.0±1.7 mV, p<0.01). Prior studies of Na$^+$ channel function in myocytes isolated from the epicardial border zone of the 5-day infarcted canine heart reveal a change in Na$^+$ channel inactivation gating not unlike those observed here with IsoK. The present inventors explored whether products of the IsoP pathway are increased in vivo in canine hearts post-infarction. Dogs were subjected to ventricular infarction according to the method of Harris, and after 5 days the core and epicardial border zones (EBZ) of the infract, as well as remote areas, were excised, snap frozen in dry ice, and stored at −70° C. for analysis. Levels of $F_2$-IsoPs esterified in the heart samples were increased strikingly in EBZ, and even to a greater extent in the core compared to levels measured in a remote area of the ventricle (FIG. 41). As a further test, the present inventors also analyzed levels of isofurans (IsoF), a new series of lipid peroxidation products the present inventors have recently described. IsoF levels were also markedly increased in the EBZ (FIG. 8), and mirrored the results with F2-IsoPs, suggesting that products of the IsoP pathway are indeed formed in substantial quantities in the border zone of cardiac infarcts.

Severe ventricular arrhythmias can occur during ischemia-reperfusion. A wealth of experimental data has described biochemical and functional changes in the heart arising from ischemia and subsequent reperfusion. Reactive nitrogen and oxygen species, including superoxide anion, hydrogen peroxide, and hydroxyl radicals, react with proteins, fatty acids, and DNA to provoke multiple functional changes. Intracellular defenses in the myocardium against reactive species include a variety of enzymatic pathways and small molecule oxidants (such as superoxide dismutase and glutathione), many of which are depleted by hypoxia. Further, the ischemia-induced shift in anaerobic metabolism forms xanthine oxidase, which generates superoxide anion upon reperfusion and reintroduction of oxygen. Free-radical scavengers, or agents that prevent free radical production, reduce the incidence of ventricular fibrillation and myocardial damage due to ischemia. While functional changes have been described in multiple ion channels and transporters, Na channel dysfunction appears to play a key role under these conditions: ischemic arrhythmias often evolve from sites of slow conduction near the ischemic border zone, which displays rate dependent slowing and facilitated reentry due to sodium channel blockade. In addition, prior studies have identified delayed recovery from Na$^+$ channel inactivation in myocardial cells harvested from the ischemic border zone of the infarcted canine heart. Here, conditions that mimic oxidative stress, as seen in myocardial ischemia, evoke a reduction of Na$^+$ current in both heterologously-expressed hH1 channels and in native cardiac myocytes, and are consistent with the emerging concepts of ischemia-induced arrhythmogenesis in vitro and in vivo. Specifically, the present inventors show that the general oxidant, t-BHP, and IsoK, a product of lipid peroxidation, act to potentiate Na$^+$ channel inactivation, suggesting that free radical-induced lipd peroxidation might play a major role in the modulation of Na$^+$ channel function during ischemia.

Excess t-BHP can initiate any number of oxidative processes, including formation of reactive oxygen species and lipid peroxidation. The reactive oxygen species and lipid peroxidation products that ensue during oxidative stress tend to form irreversible adducts with membrane proteins and irreversibly alter function. A key role for lipid peroxidation in cardiac Na$^+$ channel dysfunction is supported by our findings that exposure of HEK cells to t-BHP, and rendering canine hearts ischemic, both induce the formation of abundant quantities of $F_2$-IsoPs and IsoK. In addition, our functional data indicate that $E_2$-IsoK altered Na$^+$ channel inactivation in a manner identical to the nonspecific oxidant, t-BHP.

The Cardiac Arrhythmia Suppression Trial study demonstrates that the administration of flecainide or encainde to suppress premature ventricular contractions increased both cardiac and arrhythmic mortality, contrary to the expectation that these drugs might reduce mortality. In experimental models of myocardial infarction or ischemia-reperfusion, flecainide had proarrhythmic consequences attributable to conduction block or delay due to reduced Na$^+$ channel availability. Computer models support the hypothesis that proarrhythmic mechanisms of Na channel blockade are associated with the reduction of Na$^+$ channel availability. Furthermore, Restivo et al. showed that the enhancement of use-dependent block by flecainide led to a predisposition to arrhythmias under ischemic conditions. Similarly in our study, IsoK and t-BHP both enhanced use-dependent block by flecainide (FIG. 39B). However, IsoK had no effect on use-dependence when the putative flecainide binding site was mutated (FIG. 39C), suggesting that the synergistic effects of flecainide and IsoK are specific, and require flecainide binding to Na$^+$ channels.

Given recent studies that suggest strong familial components in the risk for cardiac arrest during myocardial ischemia and infarction, it will be important to assess whether arrhythmia risk is influenced by inherited changes in complex milieu of gene products that coassemble with Na$^-$ channels in the plasma membrane. Additionally, the identification of lipid peroxidation products as potent modifiers of cardiac Na$^+$ channel gating dysfunction during oxidative conditions raises the possibility of developing antiarrhythmic agents "targeted" for action specifically during conditions of myocardial ischemia. "Protection" of the Na$^+$ channels from lipid peroxidation deserves further evaluation as a new therapeutic approach for the prevention and treatment of sudden cardiac death.

TABLE 1

| | Kinetic parameters for recovery from inactivation | | | | |
|---|---|---|---|---|---|
| | n | $A_1$ | $\tau_{fast}$ | $A_2$ | $\tau_{slow}$ |
| control | 17 | 0.77 ± 0.03 | 12.5 ± 1.1 | 0.23 ± 0.03 | 48.7 ± 3.2 |
| IsoK | 9 | 0.79 ± 0.04 | 17.4 ± 2.2* | 0.21 ± 0.04 | 155.1 ± 32.9†† |
| flecainide 1 μM | 12 | 0.80 ± 0.04 | 10.3 ± 2.2 | 0.20 ± 0.04 | 64.3 ± 3.8 |
| flecainide + IsoK | 8 | 0.84 ± 0.04 | 29.7 ± 1.8**,† | 0.16 ± 0.04 | 19.4 ± 10.1** |

The data in FIG. 39 were fitted to a two exponential function of the form $y=y_0+A_1(1-\exp(-t/-\tau_{fast}))+A_2(1-\exp(-t/-\tau_{slow}))$, where $y_0$ is the offset, $A_1$ is the amplitude of the fast component, $A_2$ is the amplitude of the slow component and $\tau_{fast}$ and $\tau_{slow}$ are the time constants of fast and slow component, respectively. Fitted parameters (means±S.E.M.) are shown. *P<0.05, ††P<0.001 vs. control. **P<0.0001 vs. flecainide 1 uM. †P<0.001 vs. IsoK.

The following additional examples are presented to further show aspects of the present invention. They are to be viewed as exemplary of the present invention and not to be construed as being limiting thereof.

EXAMPLE 1

IsoKs, IsoK Scavengers and the Heart

Figure 42:
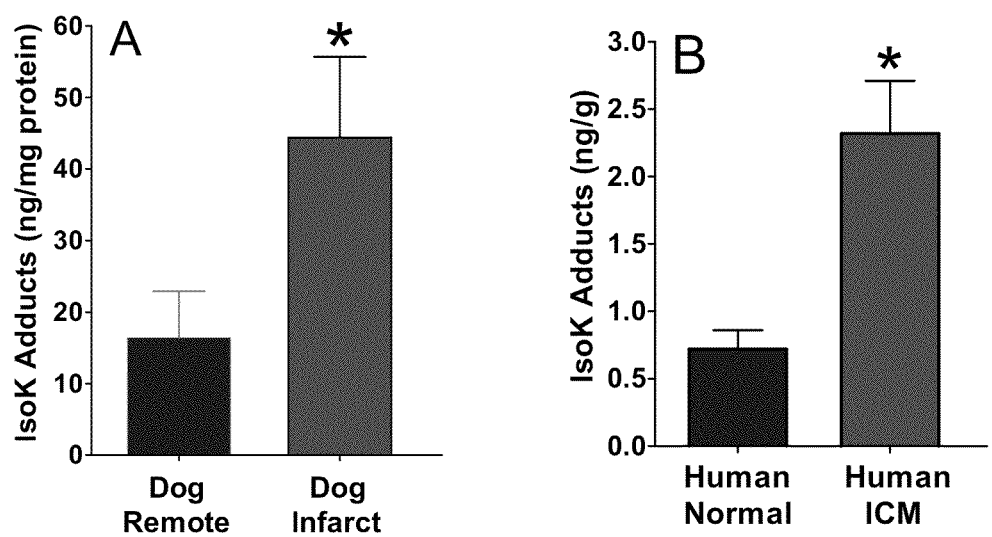
FIG. 42 is a graph showing that IskK adducts are increased in infarcted area of dogs.

IsoK adducts are increased in infarcted area of dog hearts (FIG. 42A) and in hearts from patients with coronary artery disease (ischemic cardiomyopathy ICM) (FIG. 42B)

Mimicking what happens during myocardial infarction, exposure of cells expressing the cardiac Na channel to an oxidant converts the Na channel electrophysiology into a pro-arrhythmic state.

Importantly, this is inhibited and/or prevented by compounds of the present invention.

Additionally, in infarcted mice the area of infarcted myocardium is decreased by ~½, heart contractile function is significantly improved and the survival rate is increased by ~2-fold by treatment with compounds of the present invention.

In a series of experiments, the present inventors have tested the effect of the γ KA scavenger salicylamine (SA) in mice subjected to ligation of the left anterior coronary artery resulting in a myocardial infarction. All experiments were done in blinded fashion regarding the treatment group (SA versus placebo (water)). Mice received drinking water containing either SA (1 g/l) or no drug for three days prior to coronary ligation and for 7 days afterwards. The present inventors have previously tested this dosing regimen in mice, and found that it is well tolerated and results in steady-state serum SA concentrations of approximately 1 mM. Treatment with SA improved systolic function measured as fractional LV shortening (FS) by echocardiography (contractile function 7 days post MI. *p<0.05) (FIG. 43A).

Figure 43:
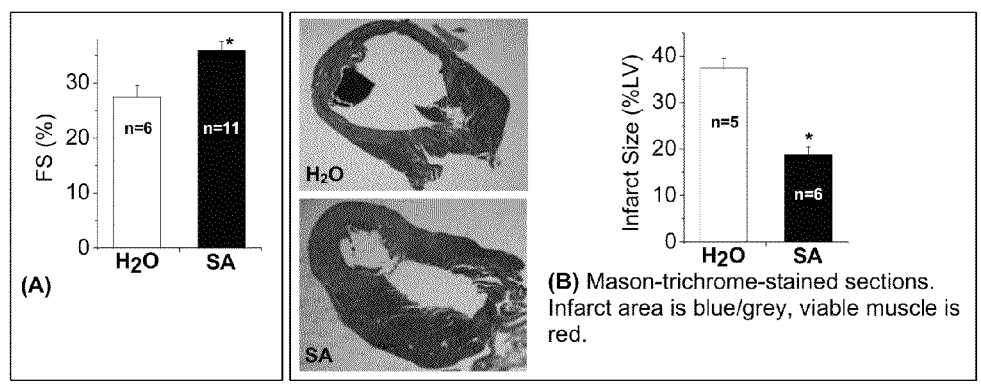
FIG. 43 is a graph showing improved systolic function with treatment with SA, and shoes SA treatment reduced infarct size of hearts harvested after coronary ligation.

SA treatment also significantly reduced infarct size of hearts harvested 7 days after coronary ligation (*p<0.05) (FIG. 43B).

Figure 50:
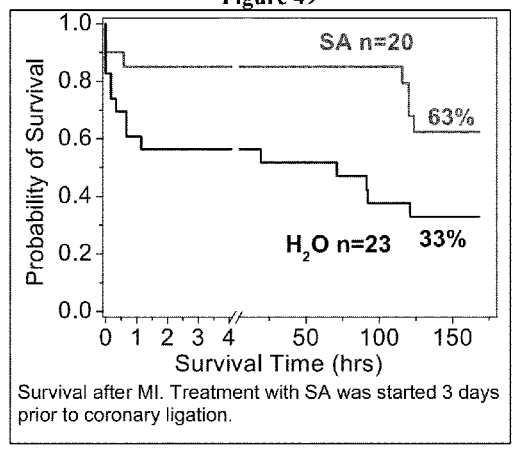
FIG. 50 is a graph showing survival after MI.

As shown in FIG. 50, there was a trend towards increased survival in the SA treated group (p=0.1 by Cox Proportional Hazard model).

EXAMPLE 2

IsoKs in Alzheimer's Disease (AD)

This Example further demonstrates the role of IsoKs in Alzheimer's Disease (AD). IsoK adducts are significantly increased in disease affected areas of brain from patients with AD, which is not present in brains from normal age-matched controls.

Figure 44:
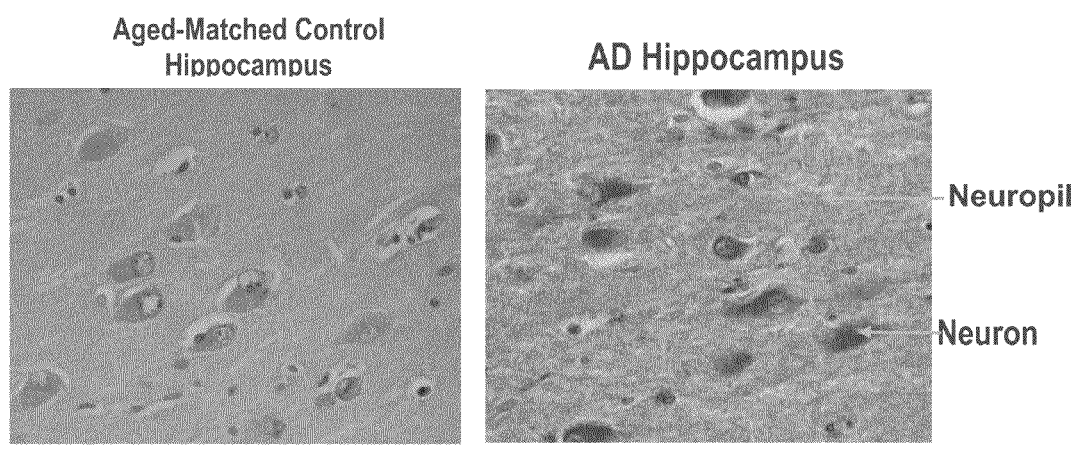
FIG. 44 shows location of IsoK adducts in AD brains.

The location of IsoK adducts in the AD brains by immunohistochemistry reveals intense staining (brown—See FIG. 44) in essentially all neurons and neuropil in disease affected areas.

Figure 45:
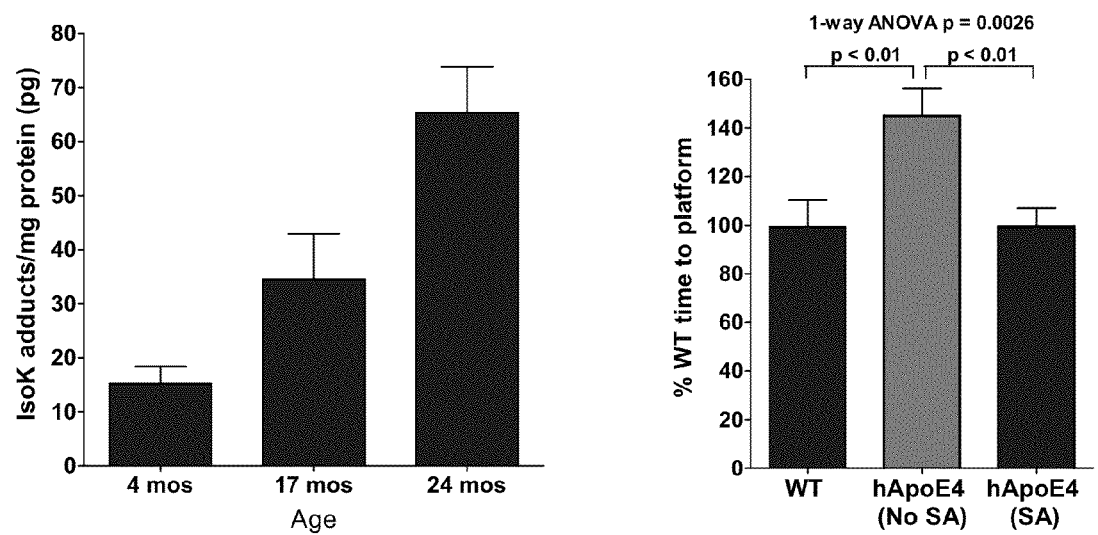
FIG. 45 is a pair of graphs showing development and memory in transgenic animals treated with an embodiment of the present invention.

The present inventors have determined that IsoK adducts increase in the brain of mice during aging. Additionally, in a transgenic mouse model of AD (hApoE4) animals develop memory and learning deficits as they age. The inventors have determined that the development of memory and learning deficits does not occur in transgenic animals treated with the compounds of the present invention. See FIG. 45.

EXAMPLE 3

This Example demonstrates the potency and selectivity of examples of scavengers of the present invention.

To understand the basis of PM's reactivity with γ KAs, the present inventors determined the second order reaction rates for a series of primary amines related to PM with the model γ KA, 4-oxopentanal (FIG. 46A). All rates are shown relative to N-α-acetyl-lysine. The present inventors discovered that a key is a phenolic amine with a hydroxyl group adjacent to the methyl amine. This study resulted in three γ KA scavengers of the present invention: pyridoxamine (PM), salicylamine (SA), and pentylpyridoxamine (PPM). Additionally, another compound of the present invention, 4-salicylamine (4-SA), the inactive regioisomer of SA, can be used as a negative control. While PM, SA, and PPM were clearly very good at scavenging γ KAs, PM is known to also scavenge methylglyoxal and other γ-ketoaldehydes derived from lipid peroxidation. While any primary amine including PM should be able to react to some extent with any aldehyde, there is variation in their reaction rates, and the individual species of aldehyde that will be scavenged in vivo is determined by both reaction rate and local concentration of the various aldehydes. The present inventors found that PM reacted with the model γ KA, 4-oxopentanal (OPA) 187 times faster than it reacted with the model γ-ketoaldehyde, methylglyoxal and that PM only trivially reacted with HNE.

Because the relative concentrations of γ-ketoaldehydes and γ KAs that form during lipid peroxidation are unknown, the present inventors oxidized arachidonic acid in the presence of both vehicle, PM, SA, or PPM and 10 molar excess of lysine. All three scavengers markedly reduced the levels of Lys-lactam adduct formed compared to vehicle treated reactions (FIG. 46B). None of the three scavengers reduced the levels of $F_2$-IsoP formed in the reactions (FIG. 46C), indicating that these scavengers do not act as antioxidants, so that the reduction in Lys-lactam levels can be attributed to γ KA scavenging. Then the amount of product formed by the reaction of PM (or PM derivative) with γKA and the various previously reported γ-ketoaldehyde products was quantified. The amounts of each of these adducts to the amount of γ KA adduct formed were normalized. The two most abundant of the γ-ketoaldehyde adducts were the N-hexanoyl (HEX) and the N-pentanedioyl (PDA) adducts. For all three scavengers, the γ KA product was formed to a far greater extent than any of the γ-ketoaldehyde products (FIG. 46D), with PPM being the most selective for forming γ KA products. Thus, PM, SA, and PPM scavenge γ KAs relatively selectively compared to other lipid peroxidation products. Although PM is highly effective in intercepting γ KAs from adduction to lysine in aqueous environments such as oxidation of arachidonic acid in buffer, it is quite hydrophilic. Therefore, PM poorly penetrates into nonpolar environments such as cellular membranes or organic solvents. In contrast, both SA and PPM readily dissolve into ethyl acetate. Because γ KAs form in situ on phospholipids during lipid peroxidation in cells, lipophilic γ KA scavengers would be expected to be more effective than a hydrophilic scavenger like PM. Because cardiac ion channels are embedded in cellular membranes, the ability to penetrate into membranes is critical. In this regard, the present inventors found that the most lipophilic scavenger, SA, provided the best protection of cellular viability in cultured HepG2 cell exposed to hydrogen peroxide.

|  | 5 day plasma | 5 day liver |
|---|---|---|
| 1 g/L SA | 1.411 mM | 0.063 mM |
| 5 g/L SA | 1.443 mM | 0.113 mM |

PPM, which is slightly less lipophilic than SA, provided slightly less protection, while the hydrophilic scavenger PM provided no significant protection.

SA was tested to determine whether it could be used in vivo. 1 g/L or 5 g/L salicylamine was added to the drinking water of C57BL6 mice for 5 days and then harvested plasma and liver from the animals. SA was measured by monitoring absorption at 259 nm after derivatization with 1,1'-thiocarbonyldiimidazole. In part from this study, the present inventors concluded that SA is orally bioavailable and that the concentrations in plasma and in tissue are likely to be sufficient to provide protection.

EXAMPLE 4

Figure 47:
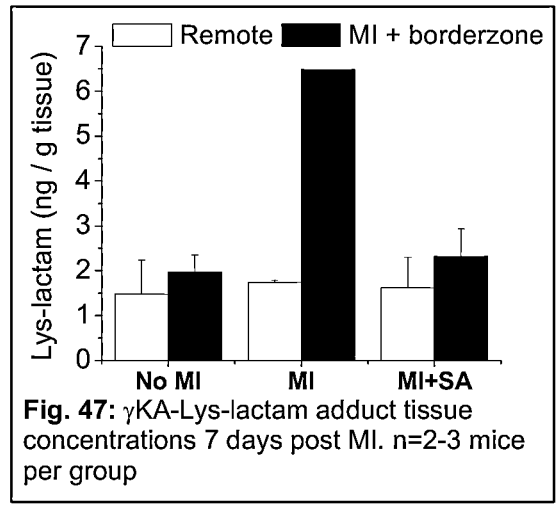
FIG. 47 is a graph that shows benefits of SA pretreatment.
Figure 48:
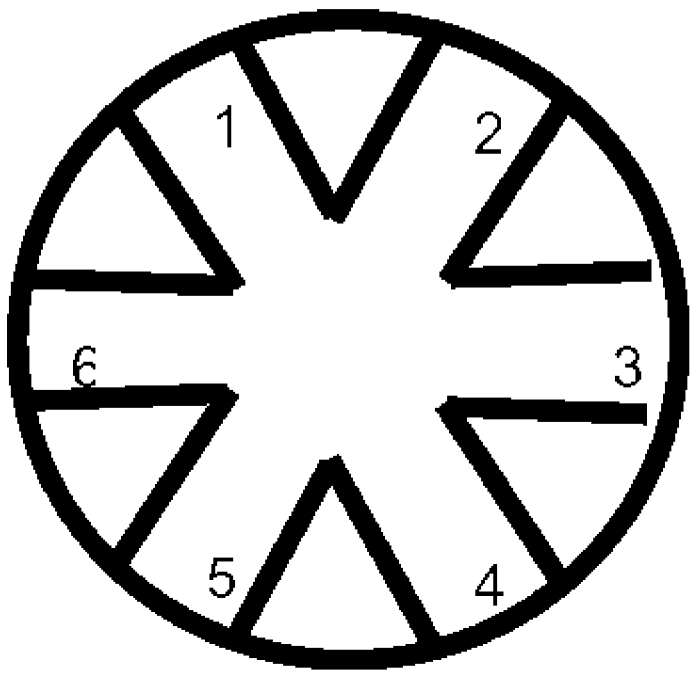
FIG. 48 shows a 6-arm water radial maze.
Figure 49:
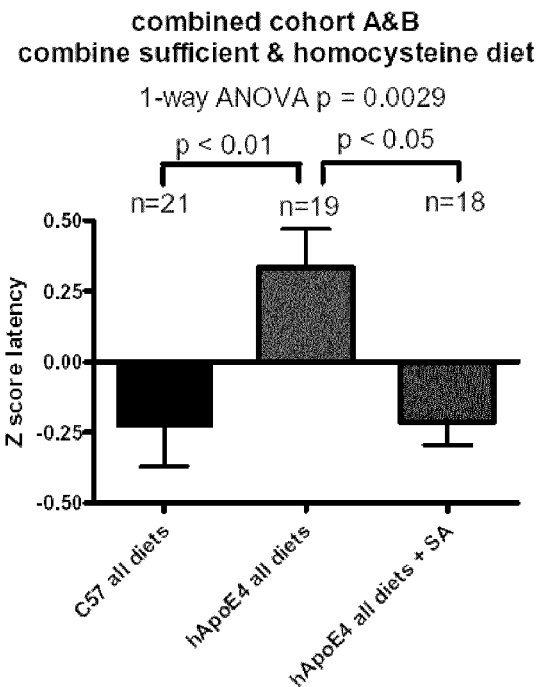
FIG. 49 is a graph showing combined diets and Z score latency.

Further Demonstration of Examples of Scavengers of the Present Invention Reducing Lys-Lactam Protein Adducts in Mice after Myocardial Infarction The present inventors examined the effect of SA treatment on Lys-lactam protein adduct formation. Mouse hearts were harvested 7 days after coronary ligation and the atria and the right ventricular free wall were removed. The remainder of each heart (LV free wall and septum) was then cut into two, roughly equal tissue specimens of ~50 mg wet weight: The anterior-apical part contained the infarct and the peri-infarct border zone (MI+borderzone), and the posterior-basal part was unaffected (Remote). The tissue content of Lys-lactam protein adducts was quantified using our LC $MS^2$ based analytical technique. Consistent with results from the dog coronary ligation model, Lys-lactam protein adducts were dramatically increased in the infarct and peri-infarct borderzone (FIG. 47) and did not changed in the remote, normal myocardium. Importantly, SA pretreatment appears to prevent the adduct formation (FIG. 47).

While preliminary, these data nevertheless suggest that the beneficial effects of SA are the result of preventing Lys-lactam protein adducts, not oxidative stress in general.

EXAMPLE 5

Effect of Salicylamine on Cognitive Impairments

This example shows that treatment with salicylamine improves memory in mouse model of dementia (transgenic humanized apoE4 mice.).

Starting at six months of age, wild-type (C57) and transgenic humanized apoE4 mice (hApoE4) were given either standard water or water containing 1 g/ml SA (+SA) as their only source of drinking water. At this time, animals were also switched from standard chow diets to either a sufficient amino acid based diet (suff) or an amino-acid based diet insufficient in choline, methionine, and folate, and enriched in homocysteine (HC). All animals were fed diets and drinking water for six months (to 12 months of age) prior to testing. The purpose of the HC diet was to attempt to exacerbate oxidative stress in these animals. Because breeding and behavioral testing is extremely time consuming, it was not possible to have sufficient animals for each group in a single cohort and still perform adequate behavioral testing. Therefore two separate cohorts of animals (A & B) were raised and tested about two month apart. Each experimental group (except the C57+SA group) had nearly equal numbers of animals in each cohort. Total animals in each group for the two cohorts is shown below:

| Groups | WATER | | SALICYLAMI | |
|---|---|---|---|---|
|  | suff | HC | suff | HC |
| C57BL6 | 11 | 10 | 4 | 9 |
| hApoE4 | 12 | 7 | 9 | 9 |

All animals were tested in a water radial arm maze test according to the protocol established by Gary Arendash, an expert in behavioral testing. The water radial arm maze is considered by Arendash to be the strictest test of working memory and has greater discriminatory power for cognitive deficits than the standard Morris Hidden Water Maze test. Prior to being testing, all animals had been trained and tested in the Morris Hidden Water Maze test.

The water radial arm maze test requires a mouse to find a hidden platform placed in one of six maze arms. The test takes place on 9 consecutive days, and the arm location of the hidden platform changes each of the 9 test days. On each test day, a mouse undergoes 4 consecutive training trials, with a different start arm for each trial. At the beginning of the trial, the mouse is placed at the opening of the start arm facing the center, the mouse released to swim, and the timer started. If the mouse enters an arm without the platform, an error is scored and the mouse is dragged by the tail back to the start arm and released. The latency timer does not stop during this time. If a mouse swims in the central area for 12 sec without picking an arm, an error is also scored and the animal is dragged back to the start arm and released. The latency timer ends when the mouse finds and mounts the hidden platform. If the latency timer reaches 60 sec before the mouse has found the platform, the mouse is gently guided to the platform. The mouse remains on the platform for 30 secs before being moved. After the fourth training trial, the mouse then rests for 30 min in a warming box before undergoing the final test trial, which starts from the last unused starting arm for that day. (The arm with the hidden platform is never used as a start arm.) The testing trials of the final 3 days are used for determining the memory performance and either latency time or errors in the testing trial can be used to measure this performance. A lower latency or error score is indicative of better working memory.

Because the two cohorts were tested approximately two months apart, and subtle changes in the testing room, water, testor behavior, etc. . . . can affect absolute latencies and errors, the two cohorts were normalized to a Z-score and combined. The Z-score statistic preserves the mean and deviation of the cohort during normalization and is calculated as (raw score—cohort average)/(cohort deviation). A Z-score=0.0 for a group would mean that the group on average performed exactly as well as the cohort on average. A Z-score of −1.0 indicates a group performed one standard deviation better (lower latency time or errors) than the cohort average, while a Z-score of 1.0 indicates a group performed one standard deviation worse than the cohort average. The Z-scores for all individuals in both cohorts for each group were then added together for statistical comparisons.

Although the HC diet was designed to exacerbate memory deficits, there were only very minor, non-significant differences in test performances between animals that received HC diet and the sufficient diet. Therefore, we grouped animals of the same genotype and treatment who received either sufficient or HC diet together for the final analysis shown.

There was a significant effect of genotype and treatment on latency (1-way ANOVA p=0.0029). As expected, animals with the humanized ApoE4 transgene performed more poorly during memory testing than did their wild-type counterparts (p<0.01, post-hoc Tukey test.). Treatment with SA significantly improved the performance of humanized ApoE4 transgenic mice (p<0.05, post-hoc Tukey test.) (Note: C57 animals receiving SA were not included in the ANOVA comparison.)

In summary, the present inventors have discovered that IsoKs appear to be a major mediator of oxidative induced cell injury and death.

Embodiments of the present invention are compounds, compositions, and methods related to selective efficient scavengers of IsoKs. The present inventors have discovered that the IsoK scavenger compounds of the present invention have salutary effects in animal models of two major human diseases, i.e. myocardial infarction and Alzheimer's disease. The compounds of the present invention further are effective in the treatment of a wide variety of diseases associated with oxidative injury.

IsoK scavengers represent a targeted novel mechanistic based pharmacologic approach to mitigate pathology in disorders involving oxidative injury.

Throughout this application, various references are cited, specifically including those listed below that may be more relevant to the neurodegenerative aspects of the invention. All such references, specifically including those listed below, are incorporated herein by reference in their entirety.

Morrow, J. D., Hill, K. E., Burk, R. F., Nammour, T. M., Badr, K. F., and Roberts, L. J., 2nd (1990) A series of prostaglandin F2-like compounds are produced in vivo in humans by a non-cyclooxygenase, free radical-catalyzed mechanism. *Proc Natl Acad Sci USA* 87, 9383-9387.

Morrow, J. D., Roberts, L. J., Daniel, V. C., Awad, J. A., Mirochnitchenko, O., Swift, L. L., and Burk, R. F. (1998) Comparison of formation of D2/E2-isoprostanes and F2-isoprostanes in vitro and in vivo—effects of oxygen tension and glutathione. *Arch Biochem Biophys* 353, 160-171.

Morrow, J. D., Minton, T. A., Mukundan, C. R., Campbell, M. D., Zackert, W. E., Daniel, V. C., Badr, K. F., Blair, I. A., and Roberts, L. J., 2nd (1994) Free radical-induced generation of isoprostanes in vivo. Evidence for the formation of D-ring and E-ring isoprostanes. *J Biol Chem* 269, 4317-4326.

Morrow, J. D., Awad, J. A., Wu, A., Zackert, W. E., Daniel, V. C., and Roberts, L. J., 2nd (1996) Nonenzymatic free radical-catalyzed generation of thromboxane-like compounds (isothromboxanes) in vivo. *J Biol Chem* 271, 23185-23190.

Roberts, L. J., 2nd, Montine, T. J., Markesbery, W. R., Tapper, A. R., Hardy, P., Chemtob, S., Dettbarn, W. D., and Morrow, J. D. (1998) Formation of isoprostane-like compounds (neuroprostanes) in vivo from docosahexaenoic acid. *J Biol Chem* 273, 13605-13612.

Reich, E. E., Zackert, W. E., Brame, C. J., Chen, Y., Roberts, L. J., 2nd, Hachey, D. L., Montine, T. J., and Morrow, J. D. (2000) Formation of novel D-ring and E-ring isoprostane-like compounds (D4/E4-neuroprostanes) in vivo from docosahexaenoic acid. *Biochemistry* 39, 2376-2383.

Montine, T. J., Markesbery, W. R., Morrow, J. D., and Roberts, L. J. (1998) Cerebrospinal fluid F2-isoprostane levels are increased in Alzheimer's disease. *Ann. Neurol.* 44, 410-413

Montine, T. J., Beal, M. F., Cudkowicz, M. E., O'Donnell, H., Margolin, R. A., McFarland, L., Bachrach, A. F., Zackert, W. E., Roberts, L. J., and Morrow, J. D. (1999) Increased CSF F2-isoprostane concentration in probable AD. *Neurology* 52, 562-565.

Reich, E. E., Markesbery, W. R., Roberts, L. J., Swift, L. L., Morrow, J. D., and Montine, T. J. (2001) Brain Regional Quantification of F-Ring and D-/E-Ring Isoprostanes and Neuroprostanes in Alzheimer's Disease. *Am. J. Pathol.* 158, 293-297

Esterbauer, H., Schaur, R. J., and Zollner, H. (1991) Chemistry and biochemistry of 4-hydroxynonenal, malonaldehyde and related aldehydes. *Free Radic Biol Med* 11, 81-128

Page, G., Barrier, L., Morel, P., Schulzberg, M., Piriou, A., and Huguet, F. (1998) Possible relationship between changes in [3H]DA uptake and autoxidation in rat striatal slices. *Exp Neurol* 152, 88-94.

Brame, C. J., Salomon, R. G., Morrow, J. D., and Roberts, L. J., 2nd (1999) Identification of extremely reactive gamma-ketoaldehydes (isolevuglandins) as products of the isoprostane pathway and characterization of their lysyl protein adducts. *J Biol Chem* 274, 13139-13146.

Bernoud-Hubac, N., Davies, S. S., Boutaud, O., Montine, T. J., and Roberts, L. J., 2nd (2001) Formation of highly reactive gamma-ketoaldehydes (neuroketals) as products of the neuroprostane pathway. *J Biol Chem* 276, 30964-30970.

Boutaud, O., Brame, C. J., Salomon, R. G., Roberts, L. J., 2nd, and Oates, J. A. (1999) Characterization of the lysyl adducts formed from prostaglandin H2 via the levuglandin pathway. *Biochemistry* 38, 9389-9396.

Davies, S. S., Amarnath, V., Montine, K. S., Bernoud-Hubac, N., Boutaud, O., Montine, T. J., and Roberts, L. J., 2nd (2002) Effects of reactive gamma-ketoaldehydes formed by the isoprostane pathway (isoketals) and cyclooxygenase pathway (levuglandins) on proteasome function. *Faseb J* 16, 715-717.

Montine, T. J., Beal, M. F., Robertson, D., Cudkowicz, M. E., Biaggioni, I., O'Donnell, H., Zackert, W. E., Roberts, L. J., and Morrow, J. D. (1999) Cerebrospinal fluid F2-isoprostanes are elevated in Huntington's disease. *Neurology* 52, 1104-1105

Butterfield, D. A., Hensley, K., Harris, M., Mattson, M., and Carney, J. (1994) beta-Amyloid peptide free radical fragments initiate synaptosomal lipoperoxidation in a sequence-specific fashion: implications to Alzheimer's disease. *Biochem Biophys Res Commun* 200, 710-715.

Goodman, Y., and Mattson, M. P. (1996) Ceramide protects hippocampal neurons against excitotoxic and oxidative insults, and amyloid beta-peptide toxicity. *J Neurochem* 66, 869-872.

Bruce, A. J., Malfroy, B., and Baudry, M. (1996) beta-Amyloid toxicity in organotypic hippocampal cultures: protection by EUK-8, a synthetic catalytic free radical scavenger. *Proc Natl Acad Sci USA* 93, 2312-2316.

Pike, C. J., Ramezan-Arab, N., and Cotman, C. W. (1997) Beta-amyloid neurotoxicity in vitro: evidence of oxidative stress but not protection by antioxidants. *J Neurochem* 69, 1601-1611.

Sayre, L. M., Zelasko, D. A., Harris, P. L., Perry, G., Salomon, R. G., and Smith, M. A. (1997) 4-Hydroxynonenal-derived advanced lipid peroxidation end products are increased in Alzheimer's disease. *J Neurochem* 68, 2092-2097.

Ando, Y., Brannstrom, T., Uchida, K., Nyhlin, N., Nasman, B., Suhr, O., Yamashita, T., Olsson, T., El Salhy, M., Uchino, M., and Ando, M. (1998) Histochemical detection of 4-hydroxynonenal protein in Alzheimer amyloid. *J Neurol Sci* 156, 172-176.

Papaioannou, N., Tooten, P. C., van Ederen, A. M., Bohl, J. R., Rofina, J., Tsangaris, T., and Gruys, E. (2001) Immunohistochemical investigation of the brain of aged dogs. I. Detection of neurofibrillary tangles and of 4-hydroxynonenal protein, an oxidative damage product, in senile plaques. *Amyloid* 8, 11-21.

Montine, K. S., Kim, P. J., Olson, S. J., Markesbery, W. R., and Montine, T. J. (1997) 4-hydroxy-2-nonenal pyrrole adducts in human neurodegenerative disease. *J Neuropathol Exp Neurol* 56, 866-871.

Sayre, L. M., Perry, G., Harris, P. L., Liu, Y., Schubert, K. A., and Smith, M. A. (2000) In situ oxidative catalysis by neurofibrillary tangles and senile plaques in Alzheimer's disease: a central role for bound transition metals. *J Neurochem* 74, 270-279.

Seshadri, S., Beiser, A., Selhub, J., Jacques, P. F., Rosenberg, I. H., D'Agostino, R. B., Wilson, P. W., and Wolf, P. A. (2002) Plasma homocysteine as a risk factor for dementia and Alzheimer's disease. *N Engl J Med* 346, 476-483.

Wang, H. X., Wahlin, A., Basun, H., Fastbom, J., Winblad, B., and Fratiglioni, L. (2001) Vitamin B(12) and folate in relation to the development of Alzheimer's disease. *Neurology* 56, 1188-1194.

Postiglione, A., Milan, G., Ruocco, A., Gallotta, G., Guiotto, G., and Di Minno, G. (2001) Plasma folate, vitamin B(12), and total homocysteine and homozygosity for the C677T mutation of the 5,10-methylene tetrahydrofolate reductase gene in patients with Alzheimer's dementia. A case-control study. *Gerontology* 47, 324-329.

Colman, N., Barker, E. A., Barker, M., Green, R., and Metz, J. (1975) Prevention of folate deficiency by food fortification. IV. Identification of target groups in addition to pregnant women in an adult rural population. *Am J Clin Nutr* 28, 471-476.

Infante-Rivard, C., Krieger, M., Gascon-Barre, M., and Rivard, G. E. (1986) Folate deficiency among institutionalized elderly. Public health impact. *J Am Geriatr Soc* 34, 211-214.

Fenech, M. F., Dreosti, I. E., and Rinaldi, J. R. (1997) Folate, vitamin B12, homocysteine status and chromosome damage rate in lymphocytes of older men. *Carcinogenesis* 18, 1329-1336.

Wright, J. D., Bialostosky, K., Gunter, E. W., Carroll, M. D., Najjar, M. F., Bowman, B. A., and Johnson, C. L. (1998) Blood folate and vitamin B12: United States, 1988-94. *Vital Health Stat* 11, 1-78.

Baik, H. W., and Russell, R. M. (1999) Vitamin B12 deficiency in the elderly. *Annu Rev Nutr* 19, 357-377

Stabler, S. P., Allen, R. H., Fried, L. P., Pahor, M., Kittner, S. J., Penninx, B. W., and Guralnik, J. M. (1999) Racial differences in prevalence of cobalamin and folate deficiencies in disabled elderly women. *Am J Clin Nutr* 70, 911-919.

Penninx, B. W., Guralnik, J. M., Ferrucci, L., Fried, L. P., Allen, R. H., and Stabler, S. P. (2000) Vitamin B(12) deficiency and depression in physically disabled older women: epidemiologic evidence from the Women's Health and Aging Study. *Am J Psychiatry* 157, 715-721.

Jones, B. G., Rose, F. A., and Tudball, N. (1994) Lipid peroxidation and homocysteine induced toxicity. *Atherosclerosis* 105, 165-170.

Hirano, K., Ogihara, T., Miki, M., Yasuda, H., Tamai, H., Kawamura, N., and Mino, M. (1994) Homocysteine induces iron-catalyzed lipid peroxidation of low-density lipoprotein that is prevented by alpha-tocopherol. *Free Radic Res* 21, 267-276.

Toborek, M., Kopieczna-Grzebieniak, E., Drozdz, M., and Wieczorek, M. (1995) Increased lipid peroxidation as a mechanism of methionine-induced atherosclerosis in rabbits. *Atherosclerosis* 115, 217-224.

Young, P. B., Kennedy, S., Molloy, A. M., Scott, J. M., Weir, D. G., and Kennedy, D. G. (1997) Lipid peroxidation induced in vivo by hyperhomocysteinaemia in pigs. *Atherosclerosis* 129, 67-71.

Huang, R. F., Hsu, Y. C., Lin, H. L., and Yang, F. L. (2001) Folate depletion and elevated plasma homocysteine promote oxidative stress in rat livers. *J Nutr* 131, 33-38.

Voutilainen, S., Morrow, J. D., Roberts, L. J., 2nd, Alfthan, G., Alho, H., Nyyssonen, K., and Salonen, J. T. (1999) Enhanced in vivo lipid peroxidation at elevated plasma total homocysteine levels. *Arterioscler Thromb Vasc Biol* 19, 1263-1266.

Davi, G., Di Minno, G., Coppola, A., Andria, G., Cerbone, A. M., Madonna, P., Tufano, A., Falco, A., Marchesani, P., Ciabattoni, G., and Patrono, C. (2001) Oxidative stress and platelet activation in homozygous homocystinuria. *Circulation* 104, 1124-1128.

White, A. R., Huang, X., Jobling, M. F., Barrow, C. J., Beyreuther, K., Masters, C. L., Bush, A. I., and Cappai, R. (2001) Homocysteine potentiates copper- and amyloid beta peptide-mediated toxicity in primary neuronal cultures: possible risk factors in the Alzheimer's-type neurodegenerative pathways. *J Neurochem* 76, 1509-1520.

Hogg, N. (1999) The effect of cyst(e)ine on the auto-oxidation of homocysteine. *Free Radic Biol Med* 27, 28-33.

Miller, J. W., Green, R., Mungas, D. M., Reed, B. R., and Jagust, W. J. (2002) Homocysteine, vitamin B6, and vascular disease in AD patients. *Neurology* 58, 1471-1475.

Kruman, II, Kumaravel, T. S., Lohani, A., Pedersen, W. A., Cutler, R. G., Kruman, Y., Haughey, N., Lee, J., Evans, M., and Mattson, M. P. (2002) Folic acid deficiency and homocysteine impair DNA repair in hippocampal neurons and sensitize them to amyloid toxicity in experimental models of Alzheimer's disease. *J Neurosci* 22, 1752-1762.

Mahley, R. W., and Huang, Y. (1999) Apolipoprotein E: from atherosclerosis to Alzheimer's disease and beyond. *Curr Opin Lipidol* 10, 207-217.

Singleton, A. B., Wharton, A., O'Brien, K. K., Walker, M. P., McKeith, I. G., Ballard, C. G., O'Brien, J., Perry, R. H., Ince, P. G., Edwardson, J. A., and Morris, C. M. (2002) Clinical and neuropathological correlates of apolipoprotein E genotype in dementia with Lewy bodies. *Dement Geriatr Cogn Disord* 14, 167-175

Ballard, C., O'Brien, J., Morris, C. M., Barber, R., Swann, A., Neill, D., and McKeith, I. (2001) The progression of cognitive impairment in dementia with Lewy bodies, vascular dementia and Alzheimer's disease. *Int J Geriatr Psychiatry* 16, 499-503.

Montine, K. S., Reich, E., Neely, M. D., Sidell, K. R., Olson, S. J., Markesbery, W. R., and Montine, T. J. (1998) Distribution of reducible 4-hydroxynonenal adduct immunoreactivity in Alzheimer disease is associated with APOE genotype. *J Neuropathol Exp Neurol* 57, 415-425.

Pratico, D., Clark, C. M., Lee, V. M., Trojanowski, J. Q., Rokach, J., and FitzGerald, G. A. (2000) Increased 8,12-iso-iPF2alpha-VI in Alzheimer's disease: correlation of a noninvasive index of lipid peroxidation with disease severity. *Ann Neurol* 48, 809-812.

Lin, C. T., Xu, Y. F., Wu, J. Y., and Chan, L. (1986) Immunoreactive apolipoprotein E is a widely distributed cellular protein. Immunohistochemical localization of apolipoprotein E in baboon tissues. *J Clin Invest* 78, 947-958.

Oropeza, R. L., Wekerle, H., and Werb, Z. (1987) Expression of apolipoprotein E by mouse brain astrocytes and its modulation by interferon-gamma. *Brain Res* 410, 45-51.

Diedrich, J. F., Minnigan, H., Carp, R. I., Whitaker, J. N., Race, R., Frey, W., 2nd, and Haase, A. T. (1991) Neuropathological changes in scrapie and Alzheimer's disease are associated with increased expression of apolipoprotein E and cathepsin D in astrocytes. *J Virol* 65, 4759-4768.

Lafarga, M., Crespo, P., Berciano, M. T., Andres, M. A., and Leon, J. (1994) Apolipoprotein E expression in the cerebellum of normal and hypercholesterolemic rabbits. *Brain Res Mol Brain Res* 21, 115-123.

Hall, E. D., Oostveen, J. A., Dunn, E., and Carter, D. B. (1995) Increased amyloid protein precursor and apolipoprotein E immunoreactivity in the selectively vulnerable hippocampus following transient forebrain ischemia in gerbils. *Exp Neurol* 135, 17-27.

Stone, D. J., Rozovsky, I., Morgan, T. E., Anderson, C. P., Hajian, H., and Finch, C. E. (1997) Astrocytes and microglia respond to estrogen with increased apoe mRNA in vivo and in vitro. *Exp Neurol* 143, 313-318.

Rebeck, G. W., Reiter, J. S., Strickland, D. K., and Hyman, B. T. (1993) Apolipoprotein E in sporadic Alzheimer's disease: allelic variation and receptor interactions. *Neuron* 11, 575-580.

Tooyama, I., Kawamata, T., Akiyama, H., Kimura, H., Moestrup, S. K., Gliemann, J., Matsuo, A., and McGeer, P. L. (1995) Subcellular localization of the low density lipoprotein receptor-related protein (alpha 2-macroglobulin receptor) in human brain. *Brain Res* 691, 235-238.

Ishiguro, M., Imai, Y., and Kohsaka, S. (1995) Expression and distribution of low density lipoprotein receptor-related protein mRNA in the rat central nervous system. *Brain Res Mol Brain Res* 33, 37-46.

Sun, Y., Wu, S., Bu, G., Onifade, M. K., Patel, S. N., LaDu, M. J., Fagan, A. M., and Holtzman, D. M. (1998) Glial fibrillary acidic protein-apolipoprotein E (apoe) transgenic mice: astrocyte-specific expression and differing biological effects of astrocyte-secreted apoE3 and apoE4 lipoproteins. *J Neurosci* 18, 3261-3272.

Han, S. H., Einstein, G., Weisgraber, K. H., Strittmatter, W. J., Saunders, A. M., Pericak-Vance, M., Roses, A. D., and Schmechel, D. E. (1994) Apolipoprotein E is localized to the cytoplasm of human cortical neurons: a light and electron microscopic study. *J Neuropathol Exp Neurol* 53, 535-544.

Han, S. H., Hulette, C., Saunders, A. M., Einstein, G., Pericak-Vance, M., Strittmatter, W. J., Roses, A. D., and Schmechel, D. E. (1994) Apolipoprotein E is present in hippocampal neurons without neurofibrillary tangles in Alzheimer's disease and in age-matched controls. *Exp Neurol* 128, 13-26.

Strittmatter, W. J., Saunders, A. M., Goedert, M., Weisgraber, K. H., Dong, L. M., Jakes, R., Huang, D. Y., Pericak-Vance, M., Schmechel, D., and Roses, A. D. (1994) Isoform-specific interactions of apolipoprotein E with microtubule-associated protein tau: implications for Alzheimer disease. *Proc Natl Acad Sci USA* 91, 11183-11186.

Fleming, L. M., Weisgraber, K. H., Strittmatter, W. J., Troncoso, J. C., and Johnson, G. V. (1996) Differential binding of apolipoprotein E isoforms to tau and other cytoskeletal proteins. *Exp Neurol* 138, 252-260.

Nathan, B. P., Bellosta, S., Sanan, D. A., Weisgraber, K. H., Mahley, R. W., and Pitas, R. E. (1994) Differential effects of apolipoproteins E3 and E4 on neuronal growth in vitro. *Science* 264, 850-852.

Holtzman, D. M., Pitas, R. E., Kilbridge, J., Nathan, B., Mahley, R. W., Bu, G., and Schwartz, A. L. (1995) Low density lipoprotein receptor-related protein mediates apolipoprotein E-dependent neurite outgrowth in a central nervous system-derived neuronal cell line. *Proc Natl Acad Sci USA* 92, 9480-9484.

Mayeux, R., Ottman, R., Maestre, G., Ngai, C., Tang, M. X., Ginsberg, H., Chun, M., Tycko, B., and Shelanski, M. (1995) Synergistic effects of traumatic head injury and apolipoprotein-epsilon 4 in patients with Alzheimer's disease. *Neurology* 45, 555-557.

Jordan, B. D., Relkin, N. R., Ravdin, L. D., Jacobs, A. R., Bennett, A., and Gandy, S. (1997) Apolipoprotein E epsilon4 associated with chronic traumatic brain injury in boxing. *Jama* 278, 136-140.

Friedman, G., Froom, P., Sazbon, L., Grinblatt, I., Shochina, M., Tsenter, J., Babaey, S., Yehuda, B., and Groswasser, Z. (1999) Apolipoprotein E-epsilon4 genotype predicts a poor outcome in survivors of traumatic brain injury. *Neurology* 52, 244-248.

Lichtman, S. W., Seliger, G., Tycko, B., and Marder, K. (2000) Apolipoprotein E and functional recovery from brain injury following postacute rehabilitation. *Neurology* 55, 1536-1539.

Sabo, T., Lomnitski, L., Nyska, A., Beni, S., Maronpot, R. R., Shohami, E., Roses, A. D., and Michaelson, D. M. (2000) Susceptibility of transgenic mice expressing human apolipoprotein E to closed head injury: the allele E3 is neuroprotective whereas E4 increases fatalities. *Neuroscience* 101, 879-884

Crawford, F. C., Vanderploeg, R. D., Freeman, M. J., Singh, S., Waisman, M., Michaels, L., Abdullah, L., Warden, D., Lipsky, R., Salazar, A., and Mullan, M. J. (2002) APOE genotype influences acquisition and recall following traumatic brain injury. *Neurology* 58, 1115-1118.

Veinbergs, I., Mallory, M., Mante, M., Rockenstein, E., Gilbert, J. R., and Masliah, E. (1999) Differential neurotrophic effects of apolipoprotein E in aged transgenic mice. *Neurosci Lett* 265, 218-222.

Hartman, R. E., Wozniak, D. F., Nardi, A., Olney, J. W., Sartorius, L., and Holtzman, D. M. (2001) Behavioral phenotyping of GFAP-apoE3 and -apoE4 transgenic mice: apoE4 mice show profound working memory impairments in the absence of Alzheimer's-like neuropathology. *Exp Neurol* 170, 326-344.

Smith, J. D., Sikes, J., and Levin, J. A. (1998) Human apolipoprotein E allele-specific brain expressing transgenic mice. *Neurobiol Aging* 19, 407-413.

Buttini, M., Akeefe, H., Lin, C., Mahley, R. W., Pitas, R. E., Wyss-Coray, T., and Mucke, L. (2000) Dominant negative effects of apolipoprotein E4 revealed in transgenic models of neurodegenerative disease. *Neuroscience* 97, 207-210

Tesseur, I., Van Dorpe, J., Spittaels, K., Van den Haute, C., Moechars, D., and Van Leuven, F. (2000) Expression of human apolipoprotein E4 in neurons causes hyperphosphorylation of protein tau in the brains of transgenic mice. *Am J Pathol* 156, 951-964.

Kaytor, M. D., and Warren, S. T. (1999) Aberrant protein deposition and neurological disease. *J Biol Chem* 274, 37507-37510.

Keller, J. N., Hanni, K. B., and Markesbery, W. R. (2000) Impaired proteasome function in Alzheimer's disease. *J. Neurochem.* 75, 436-439

McNaught, K. S., and Jenner, P. (2001) Proteasomal function is impaired in substantia nigra in Parkinson's disease. *Neurosci. Lett.* 297, 191-194

Chai, Y., Koppenhafer, S. L., Shoesmith, S. J., Perez, M. K., and Paulson, H. L. (1999) Evidence for proteasome involvement in polyglutamine disease: localization to nuclear inclusions in SCA3/MJD and suppression of polyglutamine aggregation in vitro. *Hum Mol Genet* 8, 673-682.

Bradbury, J. (2001) Proteolysis problems implicated in neurodegenerative diseases. *Lancet* 357, 1679.

Sitte, N., Merker, K., von Zglinicki, T., Grune, T., and Davies, K. J. (2000) Protein oxidation and degradation during cellular senescence of human BJ fibroblasts: part I—effects of proliferative senescence. *FASEB J.* 14, 2495-2502

Sitte, N., Merker, K., von Zglinicki, T., Davies, K. J., and Grune, T. (2000) Protein oxidation and degradation during cellular senescence of human BJ fibroblasts: part II—aging of nondividing cells. *FASEB J.* 14, 2503-2510

Sitte, N., Huber, M., Grune, T., Ladhoff, A., Doecke, W. D., von Zglinicki, T., and Davies, K. J. (2000) Proteasome inhibition by lipofuscin/ceroid during postmitotic aging of fibroblasts. *FASEB J.* 14, 1490-1498

Okada, K., Wangpoengtrakul, C., Osawa, T., Toyokuni, S., Tanaka, K., and Uchida, K. (1999) 4-Hydroxy-2-nonenal-mediated impairment of intracellular proteolysis during oxidative stress. Identification of proteasomes as target molecules. *J Biol Chem* 274, 23787-23793.

Reinheckel, T., Sitte, N., Ullrich, O., Kuckelkorn, U., Davies, K. J., and Grune, T. (1998) Comparative resistance of the 20S and 26S proteasome to oxidative stress. *Biochem J.* 335 (Pt 3), 637-642

Friguet, B., and Szweda, L. I. (1997) Inhibition of the multicatalytic proteinase (proteasome) by 4-hydroxy-2-nonenal cross-linked protein. *FEBS Lett.* 405, 21-25

Friguet, B., Szweda, L. I., and Stadtman, E. R. (1994) Susceptibility of glucose-6-phosphate dehydrogenase modified by 4-hydroxy-2-nonenal and metal-catalyzed oxidation to proteolysis by the multicatalytic protease. *Arch. Biochem. Biophys.* 311, 168-173

Shringarpure, R., Grune, T., Sitte, N., and Davies, K. J. (2000) 4-Hydroxynonenal-modified amyloid-beta peptide inhibits the proteasome: possible importance in Alzheimer's disease. *Cell Mol. Life Sci.* 57, 1802-1809

Bence, N. F., Sampat, R. M., and Kopito, R. R. (2001) Impairment of the ubiquitin-proteasome system by protein aggregation. *Science* 292, 1552-1555.

Taglialatela, G., Kaufmann, J. A., Trevino, A., and Perez-Polo, J. R. (1998) Central nervous system DNA fragmentation induced by the inhibition of nuclear factor kappa B. *Neuroreport* 9, 489-493.

Fenteany, G., and Schreiber, S. L. (1998) Lactacystin, proteasome function, and cell fate. *J Biol Chem* 273, 8545-8548.

Masaki, R., Saito, T., Yamada, K., and Ohtani-Kaneko, R. (2000) Accumulation of phosphorylated neurofilaments and increase in apoptosis-specific protein and phosphorylated c-Jun induced by proteasome inhibitors. *J Neurosci Res* 62, 75-83.

Lopes, U. G., Erhardt, P., Yao, R., and Cooper, G. M. (1997) p53-dependent induction of apoptosis by proteasome inhibitors. *J Biol Chem* 272, 12893-12896.

Perez, A., Morelli, L., Cresto, J. C., and Castano, E. M. (2000) Degradation of soluble amyloid beta-peptides 1-40, 1-42, and the Dutch variant 1-40Q by insulin degrading enzyme from Alzheimer disease and control brains. *Neurochem Res* 25, 247-255.

Kurochkin, I. V., and Goto, S. (1994) Alzheimer's beta-amyloid peptide specifically interacts with and is degraded by insulin degrading enzyme. *FEBS Lett* 345, 33-37.

McDermott, J. R., and Gibson, A. M. (1997) Degradation of Alzheimer's beta-amyloid protein by human and rat brain peptidases: involvement of insulin-degrading enzyme. *Neurochem Res* 22, 49-56.

Qiu, W. Q., Walsh, D. M., Ye, Z., Vekrellis, K., Zhang, J., Podlisny, M. B., Rosner, M. R., Safavi, A., Hersh, L. B., and Selkoe, D. J. (1998) Insulin-degrading enzyme regulates extracellular levels of amyloid beta-protein by degradation. *J Biol Chem* 273, 32730-32738.

Vekrellis, K., Ye, Z., Qiu, W. Q., Walsh, D., Hartley, D., Chesneau, V., Rosner, M. R., and Selkoe, D. J. (2000) Neurons regulate extracellular levels of amyloid beta-protein via proteolysis by insulin-degrading enzyme. *J Neurosci* 20, 1657-1665.

Miller, B. C., Eckman, E. A., Sambamurti, K., Dobbs, N., Chow, K. M., Eckman, C. B., Hersh, L. B., and Thiele, D. L. (2003) Amyloid-beta peptide levels in brain are inversely correlated with insulysin activity levels in vivo. *Proc Natl Acad Sci USA* 100, 6221-6226.

Farris, W., Mansourian, S., Chang, Y., Lindsley, L., Eckman, E. A., Frosch, M. P., Eckman, C. B., Tanzi, R. E., Selkoe, D. J., and Guenette, S. (2003) Insulin-degrading enzyme regulates the levels of insulin, amyloid beta-protein, and the beta-amyloid precursor protein intracellular domain in vivo. *Proc Natl Acad Sci USA* 100, 4162-4167.

Gasparini, L., Gouras, G. K., Wang, R., Gross, R. S., Beal, M. F., Greengard, P., and Xu, H. (2001) Stimulation of beta-amyloid precursor protein trafficking by insulin reduces intraneuronal beta-amyloid and requires mitogen-activated protein kinase signaling. *J Neurosci* 21, 2561-2570.

Bennett, R. G., Hamel, F. G., and Duckworth, W. C. (1994) Identification and isolation of a cytosolic proteolytic complex containing insulin degrading enzyme and the multicatalytic proteinase. *Biochem Biophys Res Commun* 202, 1047-1053.

Duckworth, W. C., Bennett, R. G., and Hamel, F. G. (1994) A direct inhibitory effect of insulin on a cytosolic proteolytic complex containing insulin-degrading enzyme and multicatalytic proteinase. *J Biol Chem* 269, 24575-24580.

Bennett, R. G., Hamel, F. G., and Duckworth, W. C. (1997) Characterization of the insulin inhibition of the peptidolytic activities of the insulin-degrading enzyme-proteasome complex. *Diabetes* 46, 197-203.

Saito, K., Elce, J. S., Hamos, J. E., and Nixon, R. A. (1993) Widespread activation of calcium-activated neutral proteinase (calpain) in the brain in Alzheimer disease: a potential molecular basis for neuronal degeneration. *Proc Natl Acad Sci USA* 90, 2628-2632.

Johnson, G. V., Jope, R. S., and Binder, L. I. (1989) Proteolysis of tau by calpain. *Biochem Biophys Res Commun* 163, 1505-1511.

Litersky, J. M., and Johnson, G. V. (1992) Phosphorylation by cAMP-dependent protein kinase inhibits the degradation of tau by calpain. *J Biol Chem* 267, 1563-1568.

Mercken, M., Grynspan, F., and Nixon, R. A. (1995) Differential sensitivity to proteolysis by brain calpain of adult human tau, fetal human tau and PHF-tau. *FEBS Lett* 368, 10-14.

Litersky, J. M., and Johnson, G. V. (1995) Phosphorylation of tau in situ: inhibition of calcium-dependent proteolysis. *J Neurochem* 65, 903-911.

Yang, L. S., and Ksiezak-Reding, H. (1995) Calpain-induced proteolysis of noral human tau and tau associated with paired helical filaments. *Eur J Biochem* 233, 9-17.

Zawaski, K., Gruebele, A., Kaplan, D., Reddy, S., Mortensen, A., and Novak, R. F. (1993) Evidence for enhanced expression of c-fos, c-jun, and the Ca(2+)-activated neutral protease in rat liver following carbon tetrachloride administration. *Biochem Biophys Res Commun* 197, 585-590.

Miyoshi, H., Umeshita, K., Sakon, M., Imajoh-Ohmi, S., Fujitani, K., Gotoh, M., Oiki, E., Kambayashi, J., and Monden, M. (1996) Calpain activation in plasma membrane bleb formation during tert-butyl hydroperoxide-induced rat hepatocyte injury. *Gastroenterology* 110, 1897-1904.

Andersson, M., Sjostrand, J., Petersen, A., and Karlsson, J. O. (1998) Calcium-dependent proteolysis in rabbit lens epithelium after oxidative stress. *Ophthalmic Res* 30, 157-167

Guo-Ross, S., Yang, E., and Bondy, S. C. (1998) Elevation of cerebral proteases after systemic administration of aluminum. *Neurochem Int* 33, 277-282.

Chera, B., Schaecher, K. E., Rocchini, A., Imam, S. Z., Ray, S. K., Ali, S. F., and Banik, N. L. (2002) Calpain upregulation and neuron death in spinal cord of MPTP-induced parkinsonism in mice. *Ann NY Acad Sci* 965, 274-280.

Ray, S. K., Wilford, G. G., Ali, S. F., and Banik, N. L. (2000) Calpain upregulation in spinal cords of mice with 1-methyl-4-phenyl-1,2,3,6-tetrahydropyridine (MPTP)-induced Parkinson's disease. *Ann NY Acad Sci* 914, 275-283

Brandt, R. (1996) The tau proteins in neuronal growth and development. *Front Biosci* 1, d118-130.

Takeda, A., Smith, M. A., Avila, J., Nunomura, A., Siedlak, S. L., Zhu, X., Perry, G., and Sayre, L. M. (2000) In Alzheimer's disease, heme oxygenase is coincident with Alz50, an epitope of tau induced by 4-hydroxy-2-nonenal modification. *J Neurochem* 75, 1234-1241.

Mattson, M. P., Fu, W., Waeg, G., and Uchida, K. (1997) 4-Hydroxynonenal, a product of lipid peroxidation, inhibits dephosphorylation of the microtubule-associated protein tau. *Neuroreport* 8, 2275-2281.

Montine, K. S., Olson, S. J., Amarnath, V., Whetsell, W. O., Jr., Graham, D. G., and Montine, T. J. (1997) Immunohistochemical detection of 4-hydroxy-2-nonenal adducts in Alzheimer's disease is associated with inheritance of APOE4. *Am J Pathol* 150, 437-443.

Calingasan, N. Y., Uchida, K., and Gibson, G. E. (1999) Protein-bound acrolein: a novel marker of oxidative stress in Alzheimer's disease. *J Neurochem* 72, 751-756.

Heidemann, S. R. (1996) Cytoplasmic mechanisms of axonal and dendritic growth in neurons. *Int Rev Cytol* 165, 235-296

Gray, E. G., Paula-Barbosa, M., and Roher, A. (1987) Alzheimer's disease: paired helical filaments and cytomembranes. *Neuropathol Appl Neurobiol* 13, 91-110.

Paula-Barbosa, M., Tavares, M. A., and Cadete-Leite, A. (1987) A quantitative study of frontal cortex dendritic microtubules in patients with Alzheimer's disease. *Brain Res* 417, 139-142.

Metuzals, J., Robitaille, Y., Houghton, S., Gauthier, S., Kang, C. Y., and Leblanc, R. (1988) Neuronal transformations in Alzheimer's disease. *Cell Tissue Res* 252, 239-248.

Neely, M. D., Sidell, K. R., Graham, D. G., and Montine, T. J. (1999) The lipid peroxidation product 4-hydroxynonenal inhibits neurite outgrowth, disrupts neuronal microtubules, and modifies cellular tubulin. *J Neurochem* 72, 2323-2333.

Veinbergs, I., Mallory, M., Sagara, Y., and Masliah, E. (2000) Vitamin E supplementation prevents spatial learning deficits and dendritic alterations in aged apolipoprotein E-deficient mice. *Eur J Neurosci* 12, 4541-4546.

Perry, R. H., Candy, J. M., Perry, E. K., Irving, D., Blessed, G., Fairbairn, A. F., and Tomlinson, B. E. (1982) Extensive loss of choline acetyltransferase activity is not reflected by neuronal loss in the nucleus of Meynert in Alzheimer's disease. *Neurosci Lett* 33, 311-315.

Henke, H., and Lang, W. (1983) Cholinergic enzymes in neocortex, hippocampus and basal forebrain of non-neurological and senile dementia of Alzheimer-type patients. *Brain Res* 267, 281-291.

Pedersen, W. A., Cashman, N. R., and Mattson, M. P. (1999) The lipid peroxidation product 4-hydroxynonenal impairs glutamate and glucose transport and choline acetyltransferase activity in NSC-19 motor neuron cells. *Exp Neurol* 155, 1-10.

Sobreviela, T., Clary, D. O., Reichardt, L. F., Brandabur, M. M., Kordower, J. H., and Mufson, E. J. (1994) TrkA-immunoreactive profiles in the central nervous system: colocalization with neurons containing p75 nerve growth factor receptor, choline acetyltransferase, and serotonin. *J Comp Neurol* 350, 587-611.

Mufson, E. J., Bothwell, M., and Kordower, J. H. (1989) Loss of nerve growth factor receptor-containing neurons in Alzheimer's disease: a quantitative analysis across subregions of the basal forebrain. *Exp Neurol* 105, 221-232.

Higgins, G. A., and Mufson, E. J. (1989) NGF receptor gene expression is decreased in the nucleus basalis in Alzheimer's disease. *Exp Neurol* 106, 222-236.

Kerwin, J. M., Morris, C. M., Perry, R. H., and Perry, E. K. (1992) Hippocampal nerve growth factor receptor immunoreactivity in patients with Alzheimer's and Parkinson's disease. *Neurosci Lett* 143, 101-104.

Hock, C., Heese, K., Muller-Spahn, F., Hulette, C., Rosenberg, C., and Otten, U. (1998) Decreased trkA neurotrophin receptor expression in the parietal cortex of patients with Alzheimer's disease. *Neurosci Lett* 241, 151-154.

Dubus, P., Faucheux, B., Boissiere, F., Groppi, A., Vital, C., Vital, A., Agid, Y., Hirsch, E. C., and Merlio, J. P. (2000) Expression of Trk isoforms in brain regions and in the striatum of patients with Alzheimer's disease. *Exp Neurol* 165, 285-294.

Boissiere, F., Lehericy, S., Strada, O., Agid, Y., and Hirsch, E. C. (1996) Neurotrophin receptors and selective loss of cholinergic neurons in Alzheimer disease. *Mol Chem Neuropathol* 28, 219-223.

141. Boissiere, F., Hunot, S., Faucheux, B., Hersh, L. B., Agid, Y., and Hirsch, E. C. (1997) Trk neurotrophin receptors in cholinergic neurons of patients with Alzheimer's disease. *Dement Geriatr Cogn Disord* 8, 1-8.

Strada, O., Hirsch, E. C., Javoy-Agid, F., Lehericy, S., Ruberg, M., Hauw, J. J., and Agid, Y. (1992) Does loss of nerve growth factor receptors precede loss of cholinergic neurons in Alzheimer's disease? An autoradiographic study in the human striatum and basal forebrain. *J Neurosci* 12, 4766-4774.

Olivieri, G., Otten, U., Meier, F., Baysang, G., Dimitriades-Schmutz, B., Muller-Spahn, F., and Savaskan, E. (2002) Oxidative stress modulates tyrosine kinase receptor A and p75 receptor (low-affinity nerve growth factor receptor) expression in SHSY5Y neuroblastoma cells. *Neurol Clin Neurophysiol* 2, 2-10

Gregori, L., Fuchs, C., Figueiredo-Pereira, M. E., Van Nostrand, W. E., and Goldgaber, D. (1995) Amyloid beta-protein inhibits ubiquitin-dependent protein degradation in vitro. *J Biol Chem* 270, 19702-19708.

Sano, M., Ernesto, C., Thomas, R. G., Klauber, M. R., Schafer, K., Grundman, M., Woodbury, P., Growdon, J., Cotman, C. W., Pfeiffer, E., Schneider, L. S., and Thal, L. J. (1997) A controlled trial of selegiline, alpha-tocopherol, or both as treatment for Alzheimer's disease. The Alzheimer's Disease Cooperative Study. *N Engl J Med* 336, 1216-1222.

Ortiz, M. C., Manriquez, M. C., Romero, J. C., and Juncos, L. A. (2001) Antioxidants block angiotensin II-induced increases in blood pressure and endothelin. *Hypertension* 38, 655-659.

Farr, S. A., Poon, H. F., Dogrukol-Ak, D., Drake, J., Banks, W. A., Eyerman, E., Butterfield, D. A., and Morley, J. E. (2003) The antioxidants alpha-lipoic acid and N-acetylcysteine reverse memory impairment and brain oxidative stress in aged SAMP8 mice. *J Neurochem* 84, 1173-1183.

Khalifah, R. G., Baynes, J. W., and Hudson, B. G. (1999) Amadorins: novel post-Amadori inhibitors of advanced glycation reactions. *Biochem Biophys Res Commun* 257, 251-258.

Booth, A. A., Khalifah, R. G., and Hudson, B. G. (1996) Thiamine pyrophosphate and pyridoxamine inhibit the formation of antigenic advanced glycation end-products: comparison with aminoguanidine. *Biochem Biophys Res Commun* 220, 113-119.

Stadtman, E. R. (1992) Protein oxidation and aging. *Science* 257, 1220-1224.

Rikans, L. E., and Hornbrook, K. R. (1997) Lipid peroxidation, antioxidant protection and aging. *Biochim Biophys Acta* 1362, 116-127.

Kaneko, T., Tahara, S., and Matsuo, M. (1997) Retarding effect of dietary restriction on the accumulation of 8-hydroxy-2'-deoxyguanosine in organs of Fischer 344 rats during aging. *Free Radic Biol Med* 23, 76-81

Izzotti, A., Cartiglia, C., Taningher, M., De Flora, S., and Balansky, R. (1999) Age-related increases of 8-hydroxy-2'-deoxyguanosine and DNA-protein crosslinks in mouse organs. *Mutat Res* 446, 215-223.

Roberts, L. J., 2nd, and Reckelhoff, J. F. (2001) Measurement of F(2)-isoprostanes unveils profound oxidative stress in aged rats. *Biochem Biophys Res Commun* 287, 254-256.

Carmel, G., Mager, E. M., Binder, L. I., and Kuret, J. (1996) The structural basis of monoclonal antibody Alz50's selectivity for Alzheimer's disease pathology. *J Biol Chem* 271, 32789-32795.

Liebler, D. C., Hansen, B. T., Davey, S. W., Tiscareno, L., and Mason, D. E. (2002) Peptide sequence motif analysis of tandem MS data with the SALSA algorithm. *Anal Chem* 74, 203-210.

Morrow, J. D., and Roberts, L J, II (1998) Mass spectrometric quantification of F2-isoprostanes in biological fluids and tissues as a measure of oxidant stress. *Methods Enzymol.* 300, 3-12

Maki, M., Bagci, H., Hamaguchi, K., Ueda, M., Murachi, T., and Hatanaka, M. (1989) Inhibition of calpain by a synthetic oligopeptide corresponding to an exon of the human calpastatin gene. *J Biol Chem* 264, 18866-18869.

Kawarabayashi, T., Younkin, L. H., Saido, T. C., Shoji, M., Ashe, K. H., and Younkin, S. G. (2001) Age-dependent changes in brain, CSF, and plasma amyloid (beta) protein in the Tg2576 transgenic mouse model of Alzheimer's disease. *J Neurosci* 21, 372-381.

West, M. J. (1999) Stereological methods for estimating the total number of neurons and synapses: issues of precision and bias. *Trends Neurosci* 22, 51-61.

West, M. J. (2002) Design-based stereological methods for counting neurons. *Prog Brain Res* 135, 43-51

Stitt, A., Gardiner, T. A., Alderson, N. L., Canning, P., Frizzell, N., Duffy, N., Boyle, C., Januszewski, A. S., Chachich, M., Baynes, J. W., Thorpe, S. R., and Anderson, N. L. (2002) The AGE inhibitor pyridoxamine inhibits development of retinopathy in experimental diabetes. *Diabetes* 51, 2826-2832.

Degenhardt, T. P., Alderson, N. L., Arrington, D. D., Beattie, R. J., Basgen, J. M., Steffes, M. W., Thorpe, S. R., and Baynes, J. W. (2002) Pyridoxamine inhibits early renal disease and dyslipidemia in the streptozotocin-diabetic rat. *Kidney Int* 61, 939-950.

Hansen, B. T., Jones, J. A., Mason, D. E., and Liebler, D. C. (2001) SALSA: a pattern recognition algorithm to detect electrophile-adducted peptides by automated evaluation of CID spectra in LC-MS-MS analyses. *Anal Chem* 73, 1676-1683.

Nattel, S., Pedersen, D. H., and Zipes, D. P. 1981. Alterations in regional myocardial distribution and arrhythmogenic effects of aprindine produced by coronary artery occlusion in the dog. *Cardiovascular Research* 15:80-85.

Roden, D. M., Dawson, A. K., Duff, H. J., Woosley, R. L., and Smith, R. F. 1984. Electrophysiology of O-demethyl encainide in a canine model of sustained ventricular tachycardia. *Journal of Cardiovascular Pharmacology* 6:588-595.

Investigators, T. C. 1989. Preliminary report: effect of encainide and flecainide on mortality in a randomized trial of arrhythmia suppression after myocardial infarction. The Cardiac Arrhythmia Suppression Trial (CAST) Investigators. *N Engl J Med* 321:406-412.

Akiyama, T., Pawitan, Y., Greenberg, H., Kuo, C. S., and Reynolds-Haertle, R. A. 1991. Increased risk of death and cardiac arrest from encainide and flecainide in patients after non-Q-wave acute myocardial infarction in the Cardiac Arrhythmia Suppression Trial. CAST Investigators. *Am J Cardiol* 68:1551-1555.

Brugada, P., and Brugada, J. 1992. Right bundle branch block, persistent ST segment elevation and sudden cardiac death: a distinct clinical and electrocardiographic syndrome. A multicenter report. *J Am Coll Cardiol* 20:1391-1396.

Alings, M., and Wilde, A. 1999. "Brugada" syndrome: clinical data and suggested pathophysiological mechanism. *Circulation* 99:666-673.

Balser, J. R. 1999. Sodium "channelopathies" and sudden death: must you be so sensitive? *Circ Res* 85:872-874.

Chen, Q., Kirsch, G. E., Zhang, D., Brugada, R., Brugada, J., Brugada, P., Potenza, D., Moya, A., Borggrefe, M., Breithardt, G., et al. 1998. Genetic basis and molecular mechanism for idiopathic ventricular fibrillation. *Nature* 392:293-296.

Guamieri, C., Flamigni, F., and Caldarera, C. M. 1980. Role of oxygen in the cellular damage induced by re-oxygenation of hypoxic heart. *J Mol Cell Cardiol* 12:797-808.

McCord, J. M. 1985. Oxygen-derived free radicals in postischemic tissue injury. *N Engl J Med* 312:159-163.

Bhatnagar, A. 1995. Electrophysiological effects of 4-hydroxynonenal, an aldehydic product of lipid peroxidation, on isolated rat ventricular myocytes. *Circ Res* 76:293-304.

Lu, C., Chan, S. L., Fu, W., and Mattson, M. P. 2002. The lipid peroxidation product 4-hydroxynonenal facilitates opening of voltage-dependent Ca2+ channels in neurons by increasing protein tyrosine phosphorylation. *J Biol Chem* 277:24368-24375.

Ong, B. H., Tomaselli, G. F., and Balser, J. R. 2000. A Structural Rearrangement in the Sodium Channel Pore Linked to Slow Inactivation and Use Dependence. *J Gen Physiol* 116:653-662.

Veldkamp, M. W., Viswanathan, P. C., Bezzina, C., Baartscheer, A., Wilde, A. A., and Balser, J. R. 2000. Two distinct congenital arrhythmias evoked by a multidysfunctional Na(+) channel. *Circ Res* 86:E91-E97.

Davies, S. S., Amarnath, V., Montine, K. S., Bernoud-Hubac, N., Boutaud, O., Montine, T. J., and Roberts, L. J. 2002. Effects of reactive g-ketoaldehydes formed by the isoprostane pathway (isoketals) and cyclooxygeanse pathway (levuglandins) on proteasome function. *FASEB Journal* 10.1096/fj.01-0696fje.

Morrow, J. D., and Roberts, L. J. 1998. Mass spectrometric quantification of F2-isoprostanes in biological fluids as a measure of oxidant stress. *Methods Enzymol.* 300:3-12.

Harris, A. S. 1950. Delayed development of ventricular ectopic rhythms following experimental coronary occlusion. *Circulation* 1: 1318-1328.

Pu, J., and Boyden, P. A. 1997. Alterations of Na+ currents in myocytes from epicardial border zone of the infarcted heart. A possible ionic mechanism for reduced excitability and postrepolarization refractoriness. *Circ Res* 81:110-119.

Viswanathan, P. C., Bezzina, C. R., George, A. L., Jr., Roden, D. M., Wilde, A. A., and Balser, J. R. 2001. Gating-dependent mechanisms for flecainide action in SCN5A-linked arrhythmia syndromes. *Circulation* 104: 1200-1205.

Weirich, J., and Antoni, H. 1998. Rate-dependence of antiarrhythmic and proarrhythmic properties of class I and class III antiarrhythmic drugs. *Basic Res Cardiol* 93:125-132.

Restivo, M., Yin, H., Caref, E. B., Patel, A. I., Ndrepepa, G., Avitable, M. J., Assadi, M. A., Isber, N., and el-Sherif, N. 1995. Reentrant arrhythmias in the subacute infarction period. The proarrhythmic effect of flecainide acetate on functional reentrant circuits. *Circulation* 91: 1236-1246.

Liu, H., Atkins, J., and Kass, R. S. 2003. Common molecular determinants of flecainide and lidocaine block of heart Na+ channels: evidence from experiments with neutral and quaternary flecainide analogues. *J Gen Physiol* 121: 199-214.

Fessel, J. P., Porter, N. A., Moore, K. P., Sheller, J. R., and Roberts, L. J., 2nd. 2002. Discovery of lipid peroxidation products formed in vivo with a substituted tetrahydrofuran ring (isofurans) that are favored by increased oxygen tension. *Proc Natl Acad Sci* 99:16713-16718.

Kloner, R. A. 1993. Does reperfusion injury exist in humans? *J Am Coll Cardiol* 21:537-545.

Hohnloser, S. H., and Gersh, B. J. 2003. Changing late prognosis of acute myocardial infarction: impact on management of ventricular arrhythmias in the era of reperfusion and the implantable cardioverter-defibrillator. *Circulation* 107:941-946.

Werns, S. W., Shea, M. J., and Lucchesi, B. R. 1986. Free radicals and myocardial injury: pharmacologic implications. *Circulation* 74:1-5.

Simpson, P. J., Mickelson, J. K., and Lucchesi, B. R. 1987. Free radical scavengers in myocardial ischemia. *Fed Proc* 46:2413-2421.

Carmeliet, E. 1999. Cardiac ionic currents and acute ischemia: from channels to arrhythmias. *Physiol Rev* 79:917-1017.

Kimura, Y., Iyengar, J., Engelman, R. M., and Das, D. K. 1990. Prevention of myocardial reperfusion injury in experimental coronary revascularization following ischemic arrest by a novel antiinflammatory drug, ONO-3144. *J Cardiovasc Pharmacol* 16:992-999.

Pogwizd, S. M., and Corr, P. B. 1987. Reentrant and nonreentrant mechanisms contribute to arrhythmogenesis during early myocardial ischemia: results using three-dimensional mapping. *Circulation Research* 61:352-371.

Pu, J., Balser, J. R., and Boyden, P. A. 1998. Lidocaine action on Na+ currents in ventricular myocytes from the epicardial border zone of the infarcted heart. *Circ Res* 83:431-440.

Heinecke, J. W. 1999. Mass spectrometric quantification of amino acid oxidation products in proteins: insights into pathways that promote LDL oxidation in the human artery wall. *Faseb J* 13:1113-1120.

Deuticke, B., Heller, K. B., and Haest, C. W. 1987. Progressive oxidative membrane damage in erythrocytes after pulse treatment with t-butylhydroperoxide. *Biochimica et Biophysica Acta* 899:113-124.

Echt, D. S., Liebson, P. R., Mitchell, L. B., Peters, R. W., Obias-Manno, D., Barker, A. H., Arensberg, D., Baker, A., Friedman, L., Greene, H. L., et al. 1991. Mortality and morbidity in patients receiving encainide, flecainide, or placebo. *N Engl J Med* 324:781-788.

Aupetit, J. F., Loufoua-Moundanga, J., Faucon, G., and Timour, Q. 1997. Ischaemia-induced loss or reversal of the effects of the class I antiarrhythmic drugs on vulnerability to fibrillation. *British Journal of Pharmacology* 120:523-529.

Kidwell, G. A., and Gonzalez, M. D. 1993. Effects of flecainide and D-sotalol on myocardial conduction and refractoriness: relation to antiarrhythmic and proarrhythmic drug effects. *J Cardiovasc Pharmacol* 21:621-632.

Ranger, S., and Nattel, S. 1995. Determinants and mechanisms of flecainide-induced promotion of ventricular tachycardia in anesthetized dogs. *Circulation* 92:1300-1311.

Starmer, C. F., Lastra, A. A., Nesterenko, V. V., and Grant, A. O. 1991. Proarrhythmic response to sodium channel blockade. Theoretical model and numerical experiments. *Circulation* 84:1364-1377.

Starmer, C. F., Lancaster, A. R., Lastra, A. A., and Grant, A. O. 1992. Cardiac instability amplified by use-dependent Na channel blockade. *Am J Physiol* 262.

Friedlander, Y., Siscovick, D. S., Weinmann, S., Austin, M. A., Psaty, B. M., Lemaitre, R. N., Arbogast, P., Raghunathan, T. E., and Cobb, L. A. 1998. Family history as a risk factor for primary cardiac arrest. *Circulation* 97:155-160.

Amarnath V, Amarnath K, Amarnath K, Davies S, Roberts II L J. Pyridoxamine: An Extremely Potent Scavenger of 1,4-Dicarbonyls. *Chem Res Tox.* 2004; 17:410-415.

Brame C J, Boutaud O, Davies S S, Yang T, Oates J A, Roden D, Roberts L J, 2nd. Modification of proteins by isoketal-containing oxidized phospholipids. *J Biol Chem.* 2004; 279: 13447-51.

Davies S S, Amarnath V, Brame C J, Boutaud O, Roberts L J, 2nd. Measurement of chronic oxidative and inflammatory stress by quantification of isoketal/levuglandin gamma-ketoaldehyde protein adducts using liquid chromatography tandem mass spectrometry. *Nat Protoc.* 2007; 2:2079-91.

Davies S S, Brantley E J, Voziyan P A, Amamath V, Zagol-Ikapitte I, Boutaud O, Hudson B G, Oates J A, Ii L J. Pyridoxamine Analogues Scavenge Lipid-Derived gamma-Ketoaldehydes and Protect against H(2)O(2)-Mediated Cytotoxicity. *Biochemistry.* 2006; 45: 15756-67.

Fukuda K, Davies S S, Nakajima T, Ong B H, Kupershmidt S, Fessel J, Amarnath V, Anderson M E, Boyden P A, Viswanathan P C, Roberts L J, 2nd, Balser J R. Oxidative mediated lipid peroxidation recapitulates proarrhythmic effects on cardiac sodium channels. *Circ Res.* 2005; 97:1262-9.

Metz T O, Alderson N L, Chachich M E, Thorpe S R, Baynes J W. Pyridoxamine traps intermediates in lipid peroxidation reactions in vivo: evidence on the role of lipids in chemical modification of protein and development of diabetic complications. *J Biol Chem.* 2003; 278:42012-9.

Voziyan P A, Metz T O, Baynes J W, Hudson B G. A post-Amadori inhibitor pyridoxamine also inhibits chemical modification of proteins by scavenging carbonyl intermediates of carbohydrate and lipid degradation. *J Biol Chem.* 2002; 277:3397-403.

The invention thus being described, it would be obvious that the same can be varied in many ways. Such variations that would be obvious to one of ordinary skill in the art is to be considered as being bard of this disclosure.

Unless otherwise indicated, all numbers expressing quantities of ingredients, properties such as reaction conditions, and so forth used in the Specification and Claims are to be understood as being modified in all instances by the term "about." Accordingly, unless indicated by the contrary, the numerical parameters set forth in the Specification and Claims are approximations that may vary depending upon the desired properties sought to be determined by the present invention.

Notwithstanding that the numerical ranges and parameters setting forth the broad scope of the invention are approximations, the numerical values set forth in the experimental sections or the example sections are reported as precisely as possible. Any numerical value, however, inherently contain certain errors necessarily resulting from the standard deviation found in their respective testing measurements.

We claim:

1. A method of treating oxidative damage, comprising administering an effective IsoK/NeuroK adduct formation suppressing amount of a phenolic amine compound and/or a salicylamine compound wherein the compound is selected from the formula:

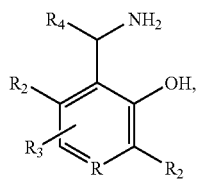

wherein:
R is N or C;
$R_2$ is independently H, substituted or unsubstituted alkyl, alkoxy, alkoxyalkyl, alkylalkoxyalkyl, alkylaminoalkyl;
$R_3$ is H, halogen, alkoxy, hydroxyl, nitro;
$R_4$ is H, substituted or unsubstituted alkyl, carboxyl; provided that when R is N, the ortho $R_2$ is $CH_3$ and $R_4$ is H, then the meta $R_2$ cannot be hydroxymethyl; or a pharmaceutically acceptable salt thereof.

2. The method of claim 1, wherein the compound is at least one of a salicylamine compound, or a, tyrosine compound.

3. The method of claim 1, wherein the compound is chosen from:

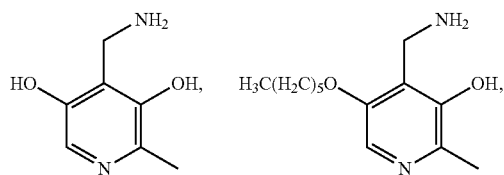
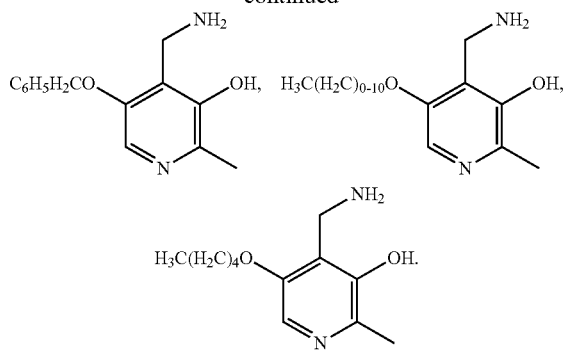

4. The method of claim 1, wherein the compound is of the following formula:

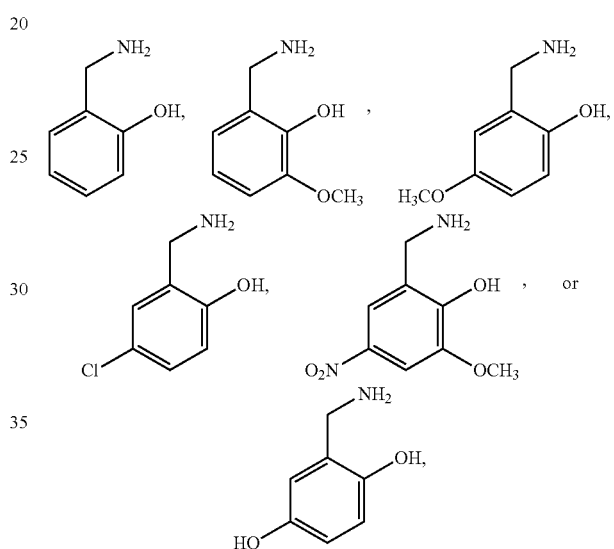

5. The method of claim 1, wherein the compound is of the following formula:

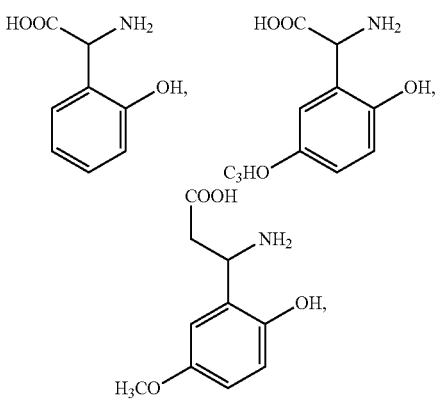

6. A method of surpressing IsoK/NeuroK adduct formation in a patient in need thereof, comprising administering an effective IsoK/NeuroK adduct formation suppressing amount of a phenolic amine compound and/or a salicylamine compound wherein the compound is selected from the formula:

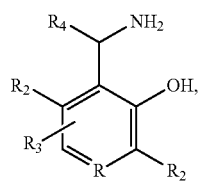

wherein:

R is N or C;

R$_2$ is independently H, substituted or unsubstituted alkyl, alkoxy, alkoxyalkyl, alkylalkoxyalkyl, alkylaminoalkyl;

R$_3$ is H, halogen, alkoxy, hydroxyl, nitro;

R$_4$ is H, substituted or unsubstituted alkyl, carboxyl; or a pharmaceutically acceptable salt thereof.

7. The method of claim 6, wherein the compound is at least one of a pyridoxamine, salicylamine, tyrosine compound.

8. The method of claim 6, wherein the compound is chosen from:

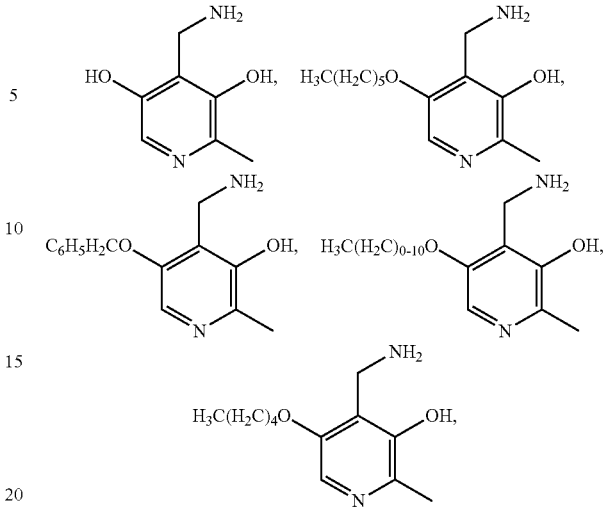

* * * * *